United States Patent
Pegurier et al.

(10) Patent No.: US 12,358,875 B2
(45) Date of Patent: Jul. 15, 2025

(54) N-(PHENYL)-INDOLE-3-SULFONAMIDE DERIVATIVES AND RELATED COMPOUNDS AS GPR17 MODULATORS FOR TREATING CNS DISORDERS SUCH AS MULTIPLE SCLEROSIS

(71) Applicant: UCB Pharma GMBH, Monheim (DE)

(72) Inventors: Cécile Pegurier, Brussels (BE); Silvia Lovera, Brussels (BE); Christa E. Mueller, Bonn (DE); Joerg Hockemeyer, Bonn (DE); Mahmoud Rashed, Cairo (EG); Ali El-Tayeb, Bonn (DE); Yong-Qiang Zhang, Shandong (CN)

(73) Assignee: UCB Pharma GMBH, Monheim (DE)

( * ) Notice: Subject to any disclaimer, the term of this patent is extended or adjusted under 35 U.S.C. 154(b) by 715 days.

(21) Appl. No.: 17/619,631

(22) PCT Filed: Jun. 16, 2020

(86) PCT No.: PCT/EP2020/066560
§ 371 (c)(1),
(2) Date: Dec. 16, 2021

(87) PCT Pub. No.: WO2020/254289
PCT Pub. Date: Dec. 24, 2020

(65) Prior Publication Data
US 2022/0298112 A1 Sep. 22, 2022

(30) Foreign Application Priority Data
Jun. 17, 2019 (EP) .................................. 19180661

(51) Int. Cl.
*C07D 209/30* (2006.01)
*A61P 25/28* (2006.01)
*C07D 401/12* (2006.01)
*C07D 471/04* (2006.01)

(52) U.S. Cl.
CPC ............ *C07D 209/30* (2013.01); *A61P 25/28* (2018.01); *C07D 401/12* (2013.01); *C07D 471/04* (2013.01)

(58) Field of Classification Search
CPC .. C07D 209/30; C07D 401/12; C07D 471/04; A61P 25/28
See application file for complete search history.

(56) References Cited

FOREIGN PATENT DOCUMENTS

| | | |
|---|---|---|
| EP | 02997966 | 3/2016 |
| EP | 02998294 | 3/2016 |
| JP | 2007-508363 | 4/2007 |
| JP | 2008-521831 | 6/2008 |
| WO | WO 2005/040114 | 5/2005 |
| WO | WO-2005040114 A1 * | 5/2005 ........... A61K 31/404 |
| WO | WO 2006/060535 | 6/2006 |
| WO | WO 2018/122232 | 7/2018 |
| WO | WO-2018122232 A1 * | 7/2018 ........... A61K 31/404 |

OTHER PUBLICATIONS

International Search Report mailed on Jul. 16, 2020 for International Application No. PCT/EP2020/066560, 2 pages.

* cited by examiner

*Primary Examiner* — Layla D Berry
*Assistant Examiner* — Sarah Grace Scrivener
(74) *Attorney, Agent, or Firm* — McDonnell Boehnen Hulbert & Berghoff LLP

(57) ABSTRACT

Disclosed are N-(phenyl)-1H-indole-3-sulfonanmide and N-(phenyl)-1H-pyrrolo[2,3-b]pyridine-3-sulfonamide derivatives of formula I substituted at the 1- and 6-positions of the 1H-indole or 1H-pyrrolo[2,3-b]pyridine moiety, as well as structurally related compounds (e.g. the N-pyridin-2-yl and the N-pyridin-3-yl analogues thereof). The present compounds have GPR17 modulating properties which are useful for treating or preventing a variety of CNS and other diseases, in particular for preventing and treating myelinating disorders such as multiple sclerosis.

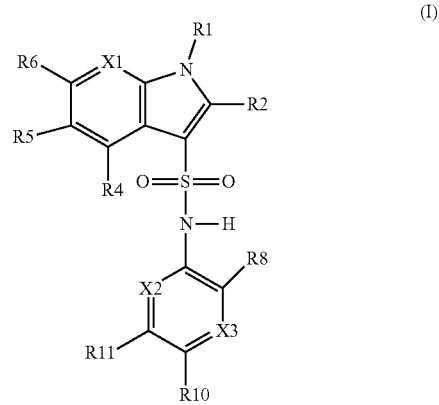

23 Claims, No Drawings

N-(PHENYL)-INDOLE-3-SULFONAMIDE DERIVATIVES AND RELATED COMPOUNDS AS GPR17 MODULATORS FOR TREATING CNS DISORDERS SUCH AS MULTIPLE SCLEROSIS

CROSS-REFERENCE TO RELATED APPLICATIONS

This application is a U.S. national phase of International Application No. PCT/EP2020/066560, filed Jun. 16, 2020, which claims priority from European Patent Application No. EP 19180661.1, filed Jun. 17, 2019, the disclosure of each of which is hereby incorporated by reference in its entirety.

BACKGROUND

G-protein coupled receptors (GPCRs) constitute the largest family of membrane receptors in the cell. They transduce extracellular signals to intracellular effector systems and are involved in a large variety of physiological phenomena, therefore representing the most common targets of pharmaceutical drugs although only a small percentage of GPCRs are targeted by current therapies.

GPCRs respond to a wide range of ligands. Due to the progress in human genome sequencing, for about 25% out of the more than 400 GPCRs (not including the olfactory GPCRs) that have been identified, a defined physiologically relevant ligand is still lacking. These receptors are known as "orphan GPCRs". "Deorphanization" and identification of their in vivo roles is expected to clarify novel regulatory mechanisms and, therefore, to disclose novel drug targets. Whether GPR17 is such an orphan receptor is still a matter of debate. Phylogenetically, GPR17 is closely related to the nucleotide P2Y receptors and the cysteinylleukotriene (CysLT1, CysLT2) receptors, with an amino acid sequence identity of between about 30 and about 35%, respectively.

Multiple-tissue Northern blot and RT-PCR analyses indicate a predominant expression of GPR17 in the central nervous system (CNS) (Ciana et al., 2006, EMBO J 25(19): 4615; Blasius et al., 1998, J Neurochem 70(4): 1357) and additionally in heart and kidney, i.e. organs typically undergoing ischemic damage. Two human GPR17 isoforms have been identified differing only by the length of their N-terminus. The short GPR17 isoform encodes a 339 amino acid-residue protein with typical rhodopsin type-seven transmembrane motifs. The long isoform encodes a receptor with a 28 amino acid longer N-terminus (Blasius et al., 1998). GPR17 is highly conserved among vertebrate species (~90% identity of amino acid sequence to both mouse and rat orthologs).

In the original deorphaning report, GPR17 was identified as a dual receptor for uracil nucleotides and cysteinyl-leukotrienes (cysLTs) LTC4 and LTD4, respectively based on $^{35}$SGTPyS binding and cAMP inhibition assays as well as single cell calcium imaging (Ciana et al., 2006, ibid). Evidence for GPR17 functionality was provided in different cellular backgrounds such as 1321N1, COS7, CHO, and HEK293 cells (Ciana et al., 2006, ibid). Subsequently, an independent study confirmed activation of GPR17 by uracil nucleotides but failed to recapitulate activation by CysLTs (Benned-Jensen and Rosenkilde, 2010, Br J Pharmacol, 159(5): 1092). Yet recent independent reports (Maekawa et al., 2009, PNAS 106(28), 11685; Qi et al., 2013, J Pharmacol Ther 347, 1, 38; Hennen et al., 2013, Sci Signal 6, 298) suggested lack of GPR17 responsiveness to both uracil nucleotides and CysLTs across different cellular backgrounds stably expressing GPR17 (1321N1, CHO, HEK293 cells). A novel regulatory role for GPR17 has also been proposed: GPR17—upon coexpression with the CysLT1 receptor-rendered the CysLT1 receptor unresponsive to its endogenous lipid mediators LTC4 and LTD4. Additional investigations are required to probe GPR17 pharmacology and function in more depth.

Drugs modulating the GPR17 activity may have neuroprotective, anti-inflammatory and anti-ischemic effects and may thus be useful for the treatment of cerebral, cardiac and renal ischemia, and stroke (WO 2006/045476), and/or for improving the recovery from these events (Bonfanti et al, Cell Death and Disease, 2017, 8, e2871).

GPR17 modulators are also thought to be involved in food uptake, insulin and leptin responses and are thus claimed to have a role in obesity treatment (WO 2011/113032).

Moreover, there is strong evidence that GPR17 is involved in myelination processes and that negative GPR17 modulators (antagonists or inverse agonists) can be valuable drugs for the treatment or alleviation of myelination disorders such as multiple sclerosis or spinal cord injury (Chen et al, Nature neuroscience 2009, 12(11):1398-1406; Ceruti et al; Brain: a journal of neurology 2009 132(Pt 8):2206-18; Hennen et al, Sci Signal, 6, 2013, 298; Simon et al J Biol Chem 291, 2016, 705; Fumagalli et al, Neuropharmacology 104, 2016, 82). More recently, two groups showed that adult GPR17−/− knock-out mice had faster remyelination than littermate wild-type after LPC induced demyelination in the spinal cord (Lu et al., Nature Scientific Reports, 2018, 8:4502) or in the corpus callosum (Ou et al., J. Neurosci., 2016, 36(41):10560). In contrast, activation of GPR17 has been shown to inhibit oligodendrocyte precursor cells (OPCs) maturation thus preventing effective myelination (Simon et al, supra). This again confirmed a potential crucial role of GPR17 in the remyelination process and as promising drug target in demyelinating diseases. The identification of potent and selective GPR17 modulators would thus be of significant relevance in the treatment of myelination disorders.

Several serious myelination diseases are known to be caused by disturbances in myelination, either by a loss of myelin (usually called demyelination), and/or by a failure of the body to properly form myelin (sometimes called dysmyelination). The myelination diseases may be idiopathic or secondary to certain trigger events like e.g. traumatic brain injury or viral infection. Myelination diseases may primarily affect the central nervous system (CNS) but may also concern the peripheral nervous system. Myelination diseases include, inter alia, multiple sclerosis, neuromyelitis optica (also known as Devic's disease), leucodystrophies, Guillain-Barré syndrome, and many other diseases as described in more detail further below (see also e.g. Love, J Clin Pathol, 59, 2006, 1151, Fumagalli et al, supra). Neurodegenerative diseases such as Alzheimer's Disease, Huntington's Disease, Parkinson's Disease, amyotropic lateral sclerosis (ALS) and multiple system atrophy (MSA) have been also strongly associated with decreased myelination recently (see e.g. Ettle et al, Mol Neurobiol 53, 2016, 3046; Jellinger and Welling, Movement Disorders, 31, 2016; 1767; Kang et al, Nature Neurosci 6, 2013, 571; Bartzokis, Neurochem Res (2007) 32:1655).

Multiple Sclerosis (MS) is a chronic progressive disorder. It is an inflammatory autoimmune disease-causing oligodendrocyte damage, demyelination and ultimately axonal loss, thus leading to a broad spectrum of signs and symptoms of a severe neurological disease, like e.g. fatigue, dizziness, mobility and walking issues, speech and swallowing difficulties, pain and others. MS takes several forms, with new symptoms either occurring in isolated attacks (relapsing forms) or building up over time (progressive forms). While certain symptoms may disappear completely between isolated attacks, severe neurological problems often remain, especially as the disease advances to a more progressive form. According to the Multiple Sclerosis Association of America, approximately 400,000 individuals have been diagnosed with MS in the United States and as many as 2.5 million worldwide, with an estimated 10,000 new cases diagnosed in the United States annually. Multiple sclerosis is two to three times more common in women than in men.

There is no known causal treatment or cure for multiple sclerosis, or many other myelination diseases. Treatments are usually symptomatic and try to improve function after an attack and prevent new attacks, by addressing the inflammatory component of the disease. Such immunomodulatory drugs are usually only modestly effective, in particular if the disease is progressed, but can have side effects and be poorly tolerated. Moreover, most of the available drugs, like β-interferons, glatiramer acetate, or therapeutic antibodies are only available in injectable form and/or only address the inflammatory component of the disease but not demyelination directly. Other drugs, like corticosteroids, show rather unspecific anti-inflammatory and immune-suppressive effects thus potentially leading to chronic side effects, such as manifested in Cushing's syndrome, for example.

A strong need therefore exists for a safe and effective drug for the treatment of myelination diseases, like MS, preferably for a drug that is suitable for oral administration. Ideally such a drug would reverse the demyelination process by decreasing demyelination and/or by promoting remyelination of the impacted neurons. A chemical compound which effectively decreases the GPR17 receptor activity could fulfil these requirements. However, only few chemical compounds are known that effectively modulate GPR17 activity.

WO 2005/103291 suggests the endogenous molecules 5 amino levulinic acid (5-ALA) and porphobilinogen (PBG) as activating ligands for GPR17, discloses analgesic effects of a GPR17 agonist and proposes the use of GPR17 agonists for treating neuropathic pain and as tools in GPR17 screening assays. However, the reported affinity of 5-ALA and PBG is quite low and the amounts needed in the assays are significant, namely in the three digit micromolar range for 5-ALA or even in the mM range for PBG, which make both compounds not well suited for use in routine screening assays or even for therapy. Moreover, PBG is a chemically unstable, reactive compound which rapidly decomposes after exposure to air and light, making it impractical to handle on a routine basis. Hence, these compounds do not offer a promising starting point to develop therapeutically effective negative GPR17 modulators.

Montelukast and pranlukast were originally developed as leukotriene receptor antagonists and were recently found to act on the GPR17 receptor as well (Ciana et al, EMBO J. 2006, 25, 4615-4627). However, subsequent results in a functional assay were contradictory for montekulast (Hennen et al, 2013, ibid), while pharmacological inhibition of GPR17 with pranlukast promotes differentiation of primary mouse (Hennen et al., 2013, ibid) and rat (Ou et al., J. Neurosci. 36, 2016, 10560-10573) oligodendrocytes. Pranlukast even phenocopies the effect of GPR17 depression in a lysolecithin model of focal demyelination because both GPR17 knock-out and pranlukast-treated wild-type mice show an earlier onset of remyelination (Ou, ibid). These results strongly support the hypothesis that GPR17 inhibitors offer potential for the treatment of human demyelinating diseases.

However, the affinity of montekulast and prankulast to GPR17 is only in the high micromolar range (Köse et al, ACS Med. Chem. Lett. 2014, 5, 326-330). Given the high protein binding of both compounds and their poor brain penetration, it is unlikely that they could reach high enough free concentrations to bind to GPR17 receptors in amounts suitable for human therapy. In addition, results obtained in vivo with these compounds are difficult to interpret due to their confounding high affinity for CYSLT1 receptors. Cross-reactions to other receptors further complicates using them for targeting GPR17.

U.S. Pat. No. 8,623,593 discloses certain indole-2-oxolic acids as GPR17 agonists and their use in screening assays. However, these derivatives are all potent agonists and are not suited to down-regulate GPR17 activity as needed in the treatment of myelination disorders such as MS. Moreover, this class of GPR17 activators does not sufficiently pass the blood-brain barrier due to their easily ionizable oxol groups, and were thus no suitable lead compounds to develop negative GPR17 modulators. See also Baqi et al, Med. Chem. Commun., 2014, 5, 86 and Köse et al, 2014, ibid.

WO 2013/167177 suggests certain phenyltriazole and benzodiazepine compounds as GPR17 antagonists. However, the disclosed compounds were selected solely based on in-silico screening results and no biological data at all was provided. The inventors of the present application were unable to confirm the GPR17 antagonist modulating activity of any of purported ligands proposed by the authors of this former patent application so far.

WO 2018/122232 discloses (Aaza)indole-benzothiophene- and benzofuran-3-sulfonamides as potent GPR17 antagonists. However, all disclosed compounds have an indole moiety with an unsubstituted nitrogen and therefore differ from the compounds of the present application who always bear an N-substitution at the indole group.

Accordingly, the present application provides for potent GPR17 modulators which surprisingly offer additional structural options by allowing the nitrogen in the indole ring to be substituted by a variety of residues with or without polar groups.

DESCRIPTION OF THE INVENTION

The present invention relates to compounds which act as negative modulators of the GPR17 receptor. In a preferred embodiment, the compounds act as negative agonists of the GPR17 receptor, thus inhibiting a constitutionally active GPR17.

The present application relates to compounds having the formula I

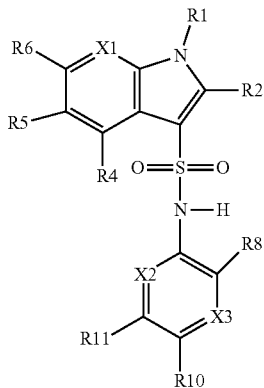

wherein
X1 is N or =C(R7)-,
X2 in N or =C(R12)-,
X3 is N or =C(R9)-,
R1 is selected from $C_{1-6}$ alkyl, $C_{3-5}$cycloalkyl, and $C_{3-5}$heterocycloalkyl, each of which is optionally substituted with one or more substituents selected from halogen, hydroxy, oxo, azido, cyano, carboxy and $C_{1-3}$alkoxy, wherein said ($C_{1-3}$)alkoxy can be unsubstituted or substituted with one or two groups selected from halogen, oxo, hydroxy and carboxy,
R2 is hydrogen or fluoro, preferably hydrogen,
R4 is hydrogen or fluoro, preferably hydrogen,
R5 is hydrogen or halogen, preferably hydrogen,
R6 is selected from halogen, cyano, cyclopropyl, $C_{1-3}$ alkyl and $C_{1-3}$ alkyloxy, wherein any cyclopropyl, alkyl or alkyloxy can be optionally substituted by one or more fluorine atoms,
R7 is selected from hydrogen, halogen, $C_{1-2}$alkyl, fluoro $C_{1-2}$ alkyl, $C_{1-2}$ alkoxy, fluoro $C_{1-2}$ alkoxy, cyclopropyl and cyclopropyloxy,
R8 is selected from hydrogen, fluoro and methoxy, preferably from fluoro and methoxy,
R9 is hydrogen or fluoro, preferably hydrogen,
R10 is selected from halogen, cyano, cyanomethyl, cyclopropyl and $C_{1-3}$ alkyloxy, which is optionally substituted with one or more substituents selected from halogen, $C_{1-3}$ alkyloxy and fluoro($C_{1-3}$)alkyloxy,
R11 is selected from hydrogen, fluoro and methoxy, preferably from fluoro and methoxy,
R12 is hydrogen or fluoro, preferably hydrogen,
and pharmaceutically acceptable salts, solvates, isotopes and cocrystals thereof.

In one preferred embodiment, in the compounds of formula I, X2 and X3 are not both nitrogen at the same time. In one preferred embodiment, X3 is N and X2 is C(R12).

Preferably, in the compounds of the present disclosure, R1 is a $C_{1-5}$ alkyl or $C_{3-4}$cycloalkyl, and even more preferably a $C_{1-4}$ alkyl or $C_{1-3}$alkyl, each of which is optionally substituted with one or more substituents selected from halogen, hydroxy, oxo, azido, cyano, carboxy and $C_{1-3}$alkoxy, wherein said ($C_{1-3}$)alkoxy can be unsubstituted or substituted with one, two or three groups selected from halogen preferably fluoro, oxo, carboxy and hydroxy. In one preferred embodiment, R1 is selected from the group of an unsubstituted methyl substituted $C_{1-4}$ alkyl and substituted $C_{1-3}$ alkyl, wherein said alkyl substituents are preferably one, two, three or four substituents selected from fluoro, chloro, hydroxy, carboxy, hydroxy($C_{1-2}$)alkoxy, fluoro($C_{1-2}$)alkoxy and fluorohydroxyethoxy.

In another preferred embodiment, R1 is $C_{1-3}$ alkyl which is unsubstituted or substituted with one or more substituents which are independently selected from fluoro, hydroxy, carboxy and $C_{1-2}$ alkoxy, wherein the $C_{1-2}$ alkoxy can be unsubstituted or substituted by one or more substituents selected from fluoro, carboxy and hydroxy, wherein the alkoxy substituent is preferably hydroxy.

In another preferred embodiment, R1 is unsubstituted methyl or $C_{1-3}$ alkyl, the latter of which is unsubstituted or substituted with one or more substituents which are independently selected from fluoro, hydroxy and $C_{1-2}$ alkoxy, wherein the $C_{1-2}$ alkoxy can be further substituted by one or more substituents selected from fluoro and hydroxy.

In another preferred embodiment, R1 is $C_{1-3}$ alkyl, which is optionally substituted with one to four substituents selected from fluoro, hydroxy, carboxy, hydroxymethoxy and hydroxyethoxy.

In another preferred embodiment, R1 is selected from the group of hydroxyethyl, hydroxypropyl, carboxymethyl, fluorohydroxypropyl, fluoroethyl, methyl and hydroxyethoxyethyl In another preferred embodiment, R1 is selected from the group of monohydroxyethyl, monohydroxypropyl, dihydroxypropyl, monocarboxymethyl, fluoromonohydroxypropyl, fluoroethyl, methyl and hydroxyethoxyethyl.

In a preferred embodiment, R2 and R4 are both hydrogen. In another preferred embodiment, R2, R4 and R5 are all hydrogen.

In one preferred embodiment R6 is selected from halogen, methyl, cyclopropyl, cyano, fluoromethoxy and fluoromethyl. In another preferred embodiment, R6 is selected from fluoro, chloro, bromo, fluoromethyl and fluoromethoxy. In another preferred embodiment,
R6 is halogen, preferably fluoro, chloro or bromo.

In one preferred embodiment, R7 is hydrogen.
One embodiment relates to compounds of formula I, wherein
X1 is N or =C(R7)-,
X2 is N or =C(R12)-,
X3 is N or =C(R9)-,
R1 is $C_{1-3}$ alkyl which is unsubstituted or substituted with one or more substituents which are independently selected from fluoro, oxo, hydroxy, carboxy, $C_{1-2}$ alkoxy, hydroxy($C_{1-2}$) alkoxy and fluoro($C_{1-2}$)alkoxy,
R2 is hydrogen or fluoro, preferably hydrogen
R4 is hydrogen or fluoro, preferably hydrogen
R5 is hydrogen or fluoro, preferably hydrogen
R6 is selected from halogen, cyano, cyclopropyl, methyl and methoxy, wherein any methyl or methoxy can be optionally substituted by one or more fluorine atoms,
R7 is selected from hydrogen, halogen, methyl, fluoro $C_{1-2}$ alkyl, $C_{1-2}$methoxy, fluoro $C_{1-2}$ alkoxy, cyclopropyl and cyclopropyloxy, and is preferably hydrogen,
R8 is selected from hydrogen, fluoro and methoxy, preferably from fluoro and methoxy,
R9 is hydrogen or fluoro, preferably hydrogen,
R10 is selected from halogen, cyano, cyanomethyl, cyclopropyl and $C_{1-3}$ alkyloxy, which is optionally substituted with one to three substituents selected from halogen, $C_{1-3}$ alkyloxy and fluoro($C_{1-3}$)alkyloxy,
R11 is selected from hydrogen, fluoro and methoxy, preferably from fluoro and methoxy,
R12 is hydrogen or fluoro, preferably hydrogen, and pharmaceutically acceptable salts, solvates, isotopes and cocrystals thereof, wherein preferably, X2 and X3 are not both nitrogen at the same time.

One embodiment relates to compounds of formula I, wherein

X1 is N or =C(R7)-,
X2 is N or =C(R12)-,
X3 is N or =C(R9)-,
R1 is $C_{1-3}$ alkyl which is unsubstituted or substituted with one or more substituents which are independently selected from fluoro, hydroxy, carboxy, $C_{1-2}$ alkoxy, hydroxy($C_{1-2}$)alkoxy and fluoro($C_{1-2}$)alkoxy,
R2, R4 and R5 are all hydrogen,
R6 is selected from fluoro, chloro, methyl and methoxy, wherein any methyl or methoxy can be optionally substituted by one or more fluorine atoms,
R7 is selected from hydrogen, fluoro and chloro, and is preferably hydrogen,
R8 is selected from hydrogen, fluoro and methoxy, preferably from fluoro and methoxy,
R9 is hydrogen or fluoro, preferably hydrogen,
R10 is selected from halogen and $C_{1-2}$ alkyloxy, which is optionally substituted with one to three substituents selected from fluoro, $C_{1-2}$ alkyloxy and fluoro($C_{1-2}$) alkyloxy,
R11 is selected from hydrogen, fluoro and methoxy, preferably from fluoro and methoxy,
R12 is hydrogen or fluoro, preferably hydrogen,
and pharmaceutically acceptable salts, solvates, isotopes and cocrystals thereof, wherein preferably, X2 and X3 are not both nitrogen at the same time.

One embodiment relates to compounds of formula I, wherein

X1 is N or =C(R7)-,
X2 is N or =C(R12)-,
X3 is N or =C(R9)-,
R1 is $C_{1-3}$ alkyl which is unsubstituted or substituted with one or more substituents which are independently selected from fluoro, hydroxy, carboxy, $C_{1-2}$ alkoxy, hydroxy($C_{1-2}$)alkoxy and fluoro($C_{1-2}$)alkoxy,
R2, R4 and R5 are all hydrogen,
R6 is selected from fluoro, chloro, and fluoromethyl,
R7 is hydrogen,
R8 is selected from hydrogen, fluoro and methoxy, preferably from fluoro and methoxy,
R9 is hydrogen or fluoro, preferably hydrogen,
R10 is selected from halogen and $C_{1-2}$ alkyloxy, which is optionally substituted with one to three substituents selected from fluoro, methoxy and fluoromethoxy,
R11 is selected from hydrogen, fluoro and methoxy, preferably from fluoro and methoxy,
R12 is hydrogen or fluoro, preferably hydrogen,
and pharmaceutically acceptable salts, solvates, isotopes and cocrystals thereof, wherein preferably, X2 and X3 are not both nitrogen at the same time.

One embodiment of the present disclosure relates to a compound according of formula I, wherein X2 is =C(R12)- and X3 is N, such compounds having Formula Ia,

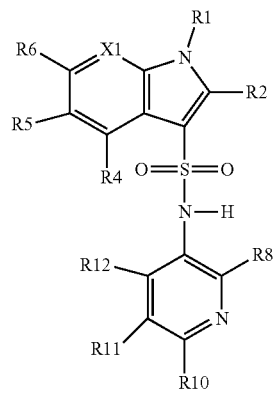

Formula Ia wherein
X1 is N or —C(R7)-,
R1 is a $C_{1-3}$ alkyl or $C_{3-4}$ cycloalkyl, preferably $C_{1-3}$ alkyl, each of which can be optionally substituted with one or more, preferably with one or two substituents selected from halogen, hydroxy, methoxy, oxo, carboxy, azido, cyano, fluoro($C_{1-2}$)alkoxy and hydroxy($C_{1-3}$)alkoxy, and preferably selected from fluoro, chloro, hydroxy, oxo, and hydroxy($C_{1-2}$)alkoxy, wherein, preferably, R1 is $C_{1-3}$ alkyl which is unsubstituted or substituted with one or more substituents which are independently selected from fluoro, hydroxy, carboxy and $C_{1-2}$ alkoxy, wherein the $C_{1-2}$ alkoxy can be unsubstituted or substituted by one or more substituents selected from fluoro, carboxy and hydroxy, preferably from fluoro and hydroxy,
R2, R4 and R5 are all hydrogen.
R6 is selected from halogen, cyclopropyl, cyano, $C_{1-3}$ alkyl and $C_{1-3}$ alkyloxy, wherein any alkyl or alkyloxy can be optionally substituted by one or more fluorine atoms,
R7 is selected from hydrogen, fluoro, chloro, fluoromethyl and fluoromethoxy, and is preferably hydrogen,
R8 is selected from hydrogen, fluoro and methoxy, preferably fluoro or methoxy,
R10 is selected from halogen, cyano and $C_{1-3}$ alkyloxy, which is optionally substituted with one top three substituents selected from halogen, $C_{1-2}$ alkyloxy and fluro($C_{1-2}$)alkyloxy,
R11 is selected from hydrogen, fluoro and methoxy, preferably from fluoro and methoxy
R12 is hydrogen or fluoro, preferably hydrogen
and pharmaceutically acceptable salts, solvates, isotopes and cocrystals thereof.

One embodiment relates to compounds of formula Ia wherein

X1 is N or —C(R7)-
R1 is $C_{1-3}$ alkyl which is unsubstituted or substituted with one or more substituents which are independently selected from fluoro, hydroxy, carboxy, $C_{1-2}$ alkoxy, hydroxy($C_{1-2}$)alkoxy and fluoro($C_{1-2}$)alkoxy,
R2, R4 and R5 are all hydrogen,
R6 is selected from fluoro, chloro, and fluoromethyl,
R7 is hydrogen or fluoro, preferably hydrogen,
R8 is selected from hydrogen, fluoro and methoxy, preferably from fluoro and methoxy,
R10 is selected from halogen and $C_{1-2}$ alkyloxy, which is optionally substituted with one to three substituents selected from fluoro, methoxy and fluoromethoxy, R11 is selected from hydrogen, fluoro and methoxy, and is preferably fluoro,
R12 is hydrogen or fluoro, preferably hydrogen,
and pharmaceutically acceptable salts, solvates, isotopes and cocrystals thereof.

In one preferred embodiment, in the compounds of formula Ia,
X1 is N or =C(R7)-
R1 is $C_{1-3}$ alkyl which is unsubstituted or substituted with one or more substituents which are independently selected from fluoro, hydroxy, carboxy, $C_{1-2}$ alkoxy, hydroxy($C_{1-2}$)alkoxy and fluoro($C_{1-2}$)alkoxy,
R2, R4 and R4 are all hydrogen,
R6 is chloro or difluoromethyl, preferably chloro,
R7 is hydrogen,
R8 is fluoro or methoxy, preferably methoxy,
R10 is selected from fluoro, chloro, bromo, fluoromethoxy, fluoroethoxy, methoxyethoxy and fluoromethoxyethoxy,
R11 is fluoro, and
R12 is fluoro or hydrogen, preferably hydrogen.

One embodiment relates to a compound according to formula I, wherein X2 is —C(R12)- and X3 is =C(R9)-, such compounds having Formula Ib

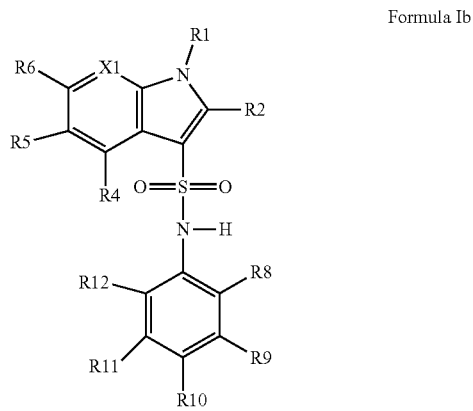

Formula Ib wherein
X1 is N or —C(R7)-,
R1 is a $C_{1-3}$ alkyl or cyclo($C_{3-4}$)alkyl, preferably $C_{1-3}$ alkyl, each of which can be optionally substituted with one or more, preferably with one or two substituents selected from halogen, hydroxy, methoxy, oxo, carboxy, azido, cyano and hydroxy($C_{1-3}$)alkoxy, and preferably selected from fluoro, chloro, hydroxy, carboxy, and hydroxy($C_{1-2}$)alkoxy, wherein, preferably, R1 is $C_{1-3}$ alkyl which is unsubstituted or substituted with one or more substituents which are independently selected from fluoro, hydroxy, carboxy and $C_{1-2}$ alkoxy, wherein the $C_{1-2}$ alkoxy can be unsubstituted or substituted by one or more substituents selected from carboxy and, preferably, fluoro and hydroxy,
R2, R4 and R5 are all hydrogen,
R6 is selected from halogen, cyclopropyl, cyano, $C_{1-3}$ alkyl and $C_{1-3}$ alkyloxy, wherein any alkyl or alkyloxy can be optionally substituted by one or more fluorine atoms
R7 is selected from hydrogen, fluoro, chloro, fluoromethyl, and fluoromethoxy, and is preferably hydrogen,
R8 is selected from hydrogen, fluoro and methoxy, preferably from fluoro and methoxy,
R9 is hydrogen or fluoro, preferably hydrogen,
R10 is selected from halogen and $C_{1-3}$ alkyloxy, which is optionally substituted with one to three substituents selected from halogen, $C_{1-2}$ alkyloxy and fluoro($C_{1-2}$)alkyloxy
R11 is selected from hydrogen, fluoro and methoxy, preferably from fluoro and methoxy
R12 is hydrogen or fluoro, preferably hydrogen,
and pharmaceutically acceptable salts, solvates, isotopes and cocrystals thereof.

One embodiment relates to compounds of Formula Ic, wherein
X1 is N or =C(R7)-,
R1 is $C_{1-3}$ alkyl which is unsubstituted or substituted with one or more substituents which are independently selected from fluoro, hydroxy, carboxy, $C_{1-2}$ alkoxy, hydroxy($C_{1-2}$)alkoxy and fluoro($C_{1-2}$)alkoxy,
R2, R4 and R5 are all hydrogen,
R6 is selected from fluoro, chloro, and fluoromethyl,
R7 is hydrogen,
R8 is selected from hydrogen, fluoro and methoxy, preferably from fluoro and methoxy,
R9 is hydrogen or fluoro, preferably hydrogen,
R10 is selected from halogen and $C_{1-2}$ alkyloxy, which is optionally substituted with one to three substituents selected from fluoro, methoxy and fluoromethoxy,
R11 is selected from hydrogen, fluoro and methoxy, and is preferably fluoro,
R12 is hydrogen or fluoro, preferably hydrogen,
and pharmaceutically acceptable salts, solvates, isotopes and cocrystals thereof.

One embodiment relates to compounds of Formula Ic, wherein
X1 is N or =C(R7)-,
R1 is $C_{1-3}$ alkyl which is unsubstituted or substituted with one or more substituents which are independently selected from fluoro, hydroxy, carboxy, $C_{1-2}$ alkoxy, hydroxy($C_{1-2}$)alkoxy and fluoro($C_{1-2}$)alkoxy,
R2, R4 and R5 are all hydrogen,
R6 is selected from fluoro, chloro, and fluoromethyl, and is preferably chloro,
R7 is hydrogen,
R8 is selected from hydrogen, fluoro and methoxy, preferably from fluoro and methoxy,
R9 is hydrogen or fluoro, preferably hydrogen,
R10 is selected from halogen and $C_{1-2}$ alkyloxy, which is optionally substituted with one to three substituents selected from fluoro, methoxy and fluoromethoxy,
R11 is selected from hydrogen, fluoro and methoxy, preferably fluoro,
R12 is hydrogen or fluoro, preferably hydrogen,
and pharmaceutically acceptable salts, solvates, isotopes and cocrystals thereof.

One embodiment relates to a compound according to formula I, wherein R2 is N and X3 is =C(R9)-, such compounds having Formula Ic Formula Ic

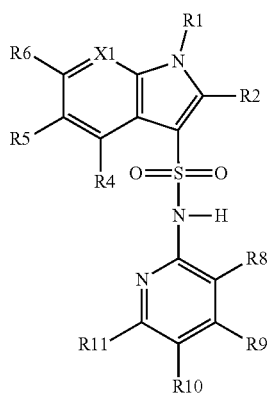

wherein
X1 is N or —C(R7)-,
R1 is $C_{1-3}$ alkyl or cyclo($C_{3-4}$)alkyl, preferably $C_{1-3}$ alkyl, each of which can be optionally substituted with one or more, preferably with one or two substituents selected from halogen, hydroxy, methoxy, oxo, carboxy, azido, cyano and hydroxy($C_{1-3}$)alkoxy, and preferably selected from fluoro, chloro, hydroxy, oxo, and hydroxy($C_{1-2}$)alkoxy, wherein, preferably, R1 is $C_{1-3}$ alkyl which is unsubstituted or substituted with one or more substituents which are independently selected from fluoro, hydroxy, carboxy and $C_{1-2}$ alkoxy, wherein the $C_{1-2}$ alkoxy can be unsubstituted or substituted by one or more substituents selected from carboxy and, preferably, fluoro and hydroxy,
R2, R4 and R5 are all hydrogen,
R6 is selected from halogen, cyano, cyclopropyl, $C_{1-3}$ alkyl and $C_{1-3}$ alkyloxy, wherein any alkyl or alkyloxy can be optionally substituted by one or more fluorine atoms
R7 is selected from hydrogen, fluoro, chloro, fluoromethyl, and fluoromethoxy,
R8 is selected from hydrogen, fluoro and methoxy, preferably from fluoro and methoxy
R9 is hydrogen or fluoro, preferably hydrogen
R10 is selected from halogen, cyano and $C_{1-3}$ alkyloxy, which is optionally substituted with one to three substituents selected from halogen, $C_{1-2}$ alkyloxy and fluoro($C_{1-2}$)alkyloxy, and
R11 is selected from hydrogen, fluoro and methoxy, preferably from fluoro and methoxy,
and pharmaceutically acceptable salts, solvates, isotopes and cocrystals thereof.

One embodiment relates to compounds of formula Ic, wherein
X1 is N or =C(R7)-,
R1 is $C_{1-3}$ alkyl which is unsubstituted or substituted with one or more substituents which are independently selected from fluoro, carboxy, hydroxy, $C_{1-2}$ alkoxy, hydroxy($C_{1-2}$)alkoxy and fluoro($C_{1-2}$)alkoxy,
R2, R4 and R5 are all hydrogen,
R6 is selected from fluoro, chloro, and fluoromethyl,
R7 is hydrogen,
R8 is selected from hydrogen, fluoro and methoxy, preferably from fluoro and methoxy,
R9 is hydrogen or fluoro, preferably hydrogen,
R10 is selected from halogen and $C_{1-2}$ alkyloxy, which is optionally substituted with one to three substituents selected from fluoro, methoxy and fluoromethoxy,
R11 is selected from hydrogen, fluoro and methoxy, preferably from fluoro and methoxy,
and pharmaceutically acceptable salts, solvates, isotopes and cocrystals thereof.

One embodiment relates to a compound according to anyone of Formula I, Ia, Ib or Ic as described hereinbefore, wherein R1 is $C_{1-3}$ alkyl, which is optionally substituted with one or two substituents selected from hydroxy, carboxy, fluoro, fluoromethoxy, fluoroethoxy, hydroxymethoxy and hydroxyethoxy One embodiment relates to a compound according to anyone of Formula I, Ia, Ib or Ic as described hereinbefore, wherein R1 is $C_{1-3}$ alkyl, which is optionally substituted with one or two substituents selected from hydroxy, carboxy, fluoro, hydroxymethoxy and hydroxyethoxy.

One embodiment relates to a compound according to anyone of Formula I, Ia, Ib or Ic as described hereinbefore, wherein R1 is selected from methyl, carboxymethyl, hydroxymethyl, carboxyethyl, hydroxyethyl, hydroxypropyl, fluoromethyl, fluoroethyl, fluoropropyl, fluorohydroxyethyl, fluorohydroxypropyl, and hydroxy($C_{1-2}$)alkoxy($C_{1-2}$) alkyl.

In one embodiment, R1 is preferably selected from monohydroxyethyl, dihydroxypropyl, fluoroethyl and mono-, di-, or trifluoromonohydroxypropyl.

One embodiment relates to a compound according to anyone of Formula I, Ia, Ib or Ic as described hereinbefore, wherein R6 is selected from fluoro, chloro, bromo, cyano, methyl, methoxy, fluoromethyl and fluoromethoxy, cyclopropyl, and isopropyl. In one preferred embodiment, R6 is chloro. In another preferred embodiment, R6 is fluoromethyl.

One embodiment relates to a compound according to anyone of Formula I, Ia, Ib or Ic as described hereinbefore, wherein R10 is selected from fluoro, chloro, bromo, fluoromethoxy, fluoroethoxy, fluoromethoxyethoxy, fluoroethoxymethoxy and fluoroethoxyethoxy. Preferably, R10 is selected from bromo, chloro, difluoromethoxy and difluoroethoxy.

One embodiment relates to a compound according to anyone of Formula I, Ia, Ib or Ic as described hereinbefore, wherein R7 is hydrogen.

One preferred embodiment relates to a compound according to anyone of Formula I, Ia, Ib or Ic as described hereinbefore, wherein R2, R4, R5 and R7 are all hydrogen.

One embodiment relates to a compound according to Formula I, wherein X is N thus having formula II Formula II

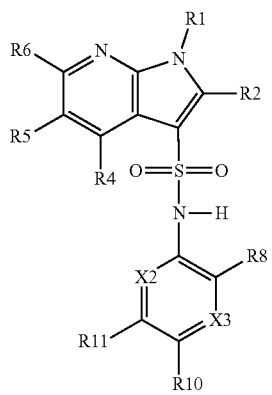

wherein R1, R2, R4, R5, R6, R10, R11, X2, and X3 are as described for the compounds of formula I (including those of subformula Ia, Ib or Ic) above, and wherein preferably, X2 and X3 are not both nitrogen.

In one embodiment, in the compounds of formula II,

X2 is N or =C(R12)-

X3 is N or =C(R9)-

R1 is $C_{1-3}$ alkyl which is unsubstituted or substituted with one or more substituents which are independently selected from fluoro, hydroxy, carboxy, $C_{1-2}$ alkoxy, hydroxy($C_{1-2}$) alkoxy and fluoro($C_{1-2}$)alkoxy, R2, R4 and R5 are all hydrogen, R6 is selected from halogen, methyl, cyclopropyl, cyano, fluoromethoxy and fluoromethyl and preferably from fluoro, chloro, and fluoromethyl, R8 is selected from hydrogen, fluoro and methoxy, preferably from fluoro and methoxy, R9 is hydrogen or fluoro, preferably hydrogen, R10 is selected from halogen and $C_{1-2}$ alkyloxy, which is optionally substituted with one to three substituents selected from fluoro, methoxy and fluoromethoxy, R11 is selected from hydrogen, fluoro and methoxy, preferably from fluoro and methoxy, R12 is hydrogen or fluoro, preferably hydrogen, and pharmaceutically acceptable salts, solvates, isotopes and cocrystals thereof, wherein preferably, X2 and X3 are not both nitrogen.

In one embodiment, the compounds have Formula IIa, IIb or IIc, respectively.

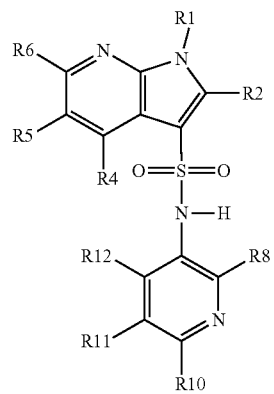

Formula IIa

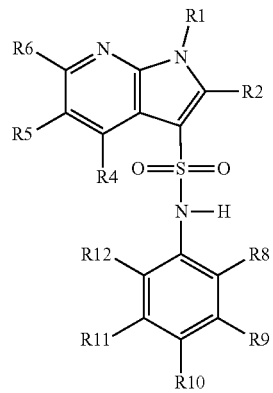

Formula IIb

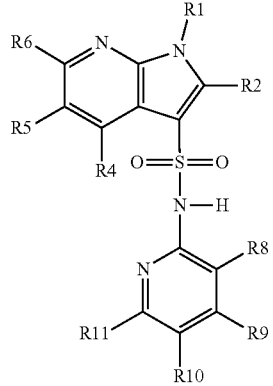

Formula IIc wherein R1, R2, R4, R5, R6, R9, R10, R11, and R12 are as described for the compounds of formula I (including those of subformula Ia, Ib or Ic) above.

One embodiment relates to compounds of formula IIA, Ib or IIc, wherein

R1 is $C_{1-3}$ alkyl which is unsubstituted or substituted with one or more substituents which are independently selected from fluoro, hydroxy, carboxy and $C_{1-2}$ alkoxy, wherein the $C_{1-2}$ alkoxy can be unsubstituted or substituted by one or more substituents selected from carboxy and, preferably, fluoro and hydroxy, R2, R4 and R5 are all hydrogen, R6 is selected from halogen, methyl, cyclopropyl, cyano, fluoromethoxy and fluoromethyl and preferably from fluoro, chloro, bromo and fluoromethyl, R8 is selected from hydrogen, fluoro and methoxy, preferably from fluoro and methoxy, R9 is hydrogen or fluoro, preferably hydrogen, R10 is selected from halogen and $C_{1-2}$ alkyloxy, which is optionally substituted with one to three substituents selected from fluoro, methoxy and fluoromethoxy, wherein R10 is preferably selected from fluoro, chloro, bromo, fluoromethoxy and fluoroethoxy R11 is selected from hydrogen, fluoro and methoxy, preferably from fluoro and methoxy, R12 is hydrogen or fluoro, preferably hydrogen, and pharmaceutically acceptable salts, solvates, isotopes and cocrystals thereof One embodiment relates to compounds of formula IIA, Ib or IIc, wherein R1 is $C_{1-3}$ alkyl which is unsubstituted or substituted with one or more substituents which are independently selected from fluoro, hydroxy, carboxy and $C_{1-2}$ alkoxy, wherein the $C_{1-2}$ alkoxy can be unsubstituted or substituted by one or more substituents selected from carboxy and, preferably, fluoro and hydroxy, R2, R4 and R5 are all hydrogen, R6 is selected from fluoro, chloro, and fluoromethyl, preferably from chloro and fluoromethyl, R8 is selected from hydrogen, fluoro and methoxy, preferably from fluoro and methoxy, R9 is hydrogen or fluoro, preferably hydrogen, R10 is selected from halogen and $C_{1-2}$ alkyloxy, which is optionally substituted with one to three substituents selected from fluoro, methoxy and fluoromethoxy, wherein R10 is preferably selected from fluoro, chloro, bromo, fluoromethoxy and fluoroethoxy R11 is selected from hydrogen, fluoro and methoxy, preferably from fluoro and methoxy, R12 is hydrogen or fluoro, preferably hydrogen,
and pharmaceutically acceptable salts, solvates, isotopes and cocrystals thereof.

One embodiment relates to a compound according to Formula I, wherein X is —C(R7)-, such compounds having formula III

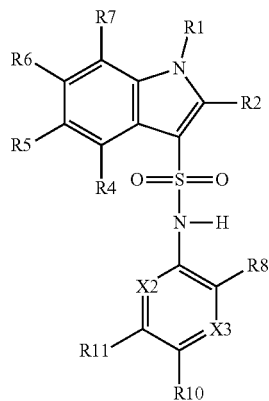

Formula III wherein R1, R2, R4, R5, R6, R10, R11, X2, and X3 are as described for the compounds of formula I, wherein preferably, X2 and X3 are not both nitrogen.

One embodiment relates to compounds or Formula III, wherein

X2 is N or =C(R12)-,

X3 is N or =C(R9)-,

R1 is C$_{1-3}$ alkyl which is unsubstituted or substituted with one or more substituents which are independently selected from fluoro, hydroxy, carboxy and C$_{1-2}$ alkoxy, wherein the C$_{1-2}$ alkoxy can be unsubstituted or substituted by one or more substituents selected from carboxy and, preferably, fluoro and hydroxy, R2, R4 and R5 are all hydrogen, R6 is selected from halogen, methyl, cyclopropyl, cyano, fluoromethoxy and fluoromethyl and preferably from fluoro, chloro, bromo and fluoromethyl, R7 is hydrogen, fluoro or chloro, preferably hydrogen, R8 is selected from hydrogen, fluoro and methoxy, preferably from fluoro and methoxy, R9 is hydrogen or fluoro, preferably hydrogen, R10 is selected from halogen and C$_{1-2}$ alkyloxy, which is optionally substituted with one to three substituents selected from fluoro, methoxy and fluoromethoxy, R11 is selected from hydrogen, fluoro and methoxy, preferably from fluoro and methoxy, R12 is hydrogen or fluoro, preferably hydrogen, and pharmaceutically acceptable salts, solvates, isotopes and cocrystals thereof, wherein preferably, X2 and X3 are not both nitrogen at the same time.

One embodiment relates to compounds or Formula III, wherein

X2 is N or =C(R12)-,

X3 is N or =C(R9)-,

R1 is C$_{1-3}$ alkyl which is unsubstituted or substituted with one or more substituents which are independently selected from fluoro, hydroxy, carboxy and C$_{1-2}$ alkoxy, wherein the C$_{1-2}$ alkoxy can be unsubstituted or substituted by one or more substituents selected from carboxy and, preferably, fluoro and hydroxy, R2, R4 and R5 are all hydrogen, R6 is selected from fluoro, chloro, and fluoromethyl, R7 is hydrogen, fluoro or chloro, preferably hydrogen, R8 is selected from hydrogen, fluoro and methoxy, preferably from fluoro and methoxy, R9 is hydrogen or fluoro, preferably hydrogen, R10 is selected from halogen and C$_{1-2}$ alkyloxy, which is optionally substituted with one to three substituents selected from fluoro, methoxy and fluoromethoxy, R11 is selected from hydrogen, fluoro and methoxy, preferably from fluoro and methoxy, R12 is hydrogen or fluoro, preferably hydrogen, and pharmaceutically acceptable salts, solvates, isotopes and cocrystals thereof, wherein preferably, X2 and X3 are not both nitrogen at the same time.

One embodiment relates to compounds having Formula IIIa, IIIb or IIIc, respectively.

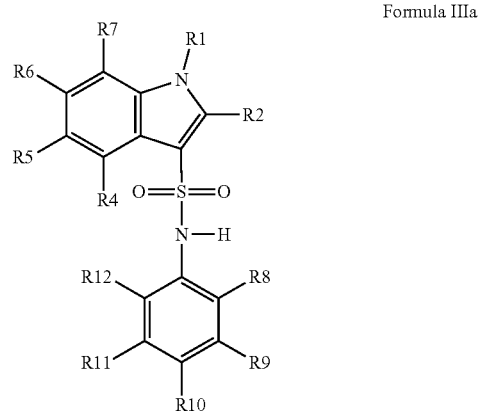

Formula IIIa

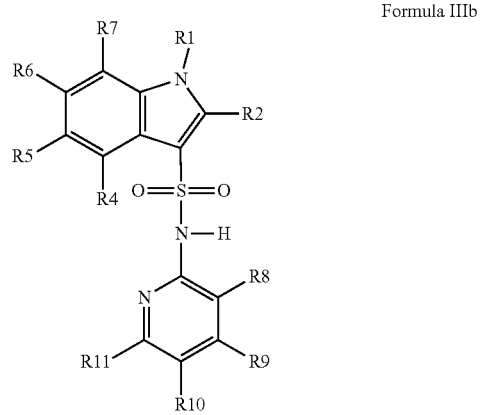

Formula IIIb

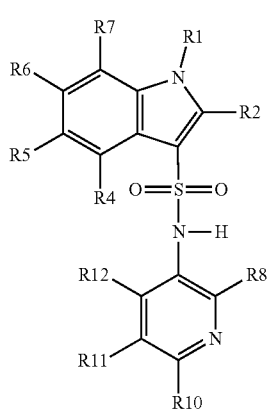

Formula IIIc

R1, R2, R4, R5, R6, R10, R11, R9 and R12 are as described above.

One embodiment relates to compounds having formula IIIa, IIIb or IIIc, wherein
- R1 is $C_{1-3}$ alkyl which is unsubstituted or substituted with one or more substituents which are independently selected from fluoro, hydroxy, carboxy and $C_{1-2}$ alkoxy, wherein the $C_{1-2}$ alkoxy can be unsubstituted or substituted by one or more substituents selected from carboxy and, preferably, fluoro and hydroxy,
- R2, R4 and R5 are all hydrogen,
- R6 is selected from halogen, methyl, cyclopropyl, cyano, fluoromethoxy and fluoromethyl and preferably from fluoro, chloro, bromo and fluoromethyl,
- R7 is hydrogen, fluoro or chloro, preferably hydrogen,
- R8 is selected from hydrogen, fluoro and methoxy, preferably from fluoro and methoxy,
- R9 is hydrogen or fluoro, preferably hydrogen,
- R10 is selected from halogen and $C_{1-2}$ alkyloxy, which is optionally substituted with one to three substituents selected from fluoro, methoxy and fluoromethoxy, wherein R10 is preferably selected from fluoro, chloro, bromo, fluoromethoxy and fluoroethoxy
- R11 is selected from hydrogen, fluoro and methoxy, preferably from fluoro and methoxy,
- R12 is hydrogen or fluoro, preferably hydrogen,
and pharmaceutically acceptable salts, solvates, isotopes and cocrystals thereof.

One embodiment relates to compounds having formula IIIA, IIIb or IIIc, wherein
- R1 is $C_{1-3}$ alkyl which is unsubstituted or substituted with one or more substituents which are independently selected from fluoro, hydroxy, carboxy and $C_{1-2}$ alkoxy, wherein the $C_{1-2}$ alkoxy can be unsubstituted or substituted by one or more substituents selected from carboxy and, preferably, fluoro and hydroxy,
- R2, R4 and R5 are all hydrogen,
- R6 is selected from fluoro, chloro, and fluoromethyl,
- R7 is hydrogen, fluoro or chloro, preferably hydrogen,
- R8 is selected from hydrogen, fluoro and methoxy, preferably from fluoro and methoxy,
- R9 is hydrogen or fluoro, preferably hydrogen,
- R10 is selected from halogen and $C_{1-2}$ alkyloxy, which is optionally substituted with one to three substituents selected from fluoro, methoxy and fluoromethoxy, wherein R10 is preferably selected from fluoro, chloro, bromo, fluoromethoxy and fluoroethoxy
- R11 is selected from hydrogen, fluoro and methoxy, preferably from fluoro and methoxy,
- R12 is hydrogen or fluoro, preferably hydrogen,
and pharmaceutically acceptable salts, solvates, isotopes and cocrystals thereof.

One preferred embodiment relates to the compounds disclosed herein, wherein
- R1 is selected from $C_{1-3}$ alkyl and $(C_{1-2})$alkoxy$(C_{1-2})$ alkyl, each of which is optionally substituted with one to four substituents selected from hydroxy and fluoro,
- R2, R4, R5, R7, if R7 is present, R9 and R12 are all hydrogen,
- R6 is selected from fluoro, chloro, bromo, fluoromethoxy and fluoromethyl, and is preferably chloro or bromo,
- R8 is selected from fluoro and methoxy,
- R10 is selected from halogen and fluro$(C_{1-3})$alkoxy,
- R11 is fluoro or methoxy,
and pharmaceutically acceptable salts, solvates, isotopes and cocrystals thereof, One preferred embodiment relates to a compound selected from the group of
N-(4-bromo-2,5-difluorophenyl)-6-chloro-1-(2-fluoro-3-hydroxypropyl)pyrrolo[2,3-b]pyridine-3-sulfonamide
N-(4-bromo-2,5-difluorophenyl)-6-chloro-1-(2-fluoro-3-hydroxypropyl)indole-3-sulfonamide
6-chloro-N-(6-chloro-5-fluoro-2-methoxypyridin-3-yl)-1-(3-fluoro-2-hydroxypropyl)indole-3-sulfonamide
N-(4-bromo-2,5-difluorophenyl)-6-chloro-1-(3,3,3-trifluoro-2-hydroxypropyl)indole-3-sulfonamide
6-chloro-N-(6-chloro-5-fluoro-2-methoxypyridin-3-yl)-1-(2,2-difluoroethyl)indole-3-sulfonamide
6-chloro-N-(6-chloro-5-fluoro-2-methoxypyridin-3-yl)-1-(2,3-dihydroxypropyl)indole-3-sulfonamide
6-chloro-N-(6-chloro-5-fluoro-2-methoxypyridin-3-yl)-1-methylindole-3-sulfonamide
N-(4-bromo-2,5-difluorophenyl)-6-chloro-1-(3-fluoro-2-hydroxypropyl)indole-3-sulfonamide
6-chloro-N-[4-(difluoromethoxy)-2,5-difluorophenyl]-1-(2,3-dihydroxypropyl)indole-3-sulfonamide
N-(4-bromo-2,5-difluorophenyl)-6-chloro-1-(2-hydroxypropyl)indole-3-sulfonamide
N-(4-bromo-2,5-difluorophenyl)-6-chloro-1-methylpyrrolo[2,3-b]pyridine-3-sulfonamide 6-chloro-N-[4-(difluoromethoxy)-2,5-difluorophenyl]-1-methylpyrrolo[2,3-b]pyridine-3-sulfonamide
N-(4-bromo-2,5-difluorophenyl)-6-chloro-1-(2,3-dihydroxypropyl)pyrrolo[2,3-b]pyridine-3-sulfonamide
N-(4-bromo-2,5-difluorophenyl)-6-chloro-1-(2-hydroxyethyl)pyrrolo[2,3-b]pyridine-3-sulfonamide
N-(4-bromo-2,5-difluorophenyl)-6-chloro-1-[2-(2-hydroxyethoxy)ethyl]indole-3-sulfonamide
6-chloro-N-[6-(difluoromethoxy)-5-fluoro-2-methoxypyridin-3-yl]-1-(2-hydroxyethyl)pyrrolo[2,3-b]pyridine-3-sulfonamide
6-chloro-N-[4-(difluoromethoxy)-2,5-difluorophenyl]-1-(2-fluoroethyl)indole-3-sulfonamide
N-(4-bromo-2,5-difluorophenyl)-6-chloro-1-(2,3-dihydroxypropyl)indole-3-sulfonamide
6-chloro-N-[4-(difluoromethoxy)-2,5-difluorophenyl]-1-methylindole-3-sulfonamide
6-chloro-N-[4-(difluoromethoxy)-2,5-difluorophenyl]-1-(2-hydroxyethyl)indole-3-sulfonamide
N-(4-bromo-2,5-difluorophenyl)-6-chloro-1-methylindole-3-sulfonamide
2-[3-[(4-bromo-2,5-difluorophenyl)sulfamoyl]-6-chloroindol-1-yl]acetic acid, and N-(4-bromo-2,5-difluorophenyl)-6-chloro-1-(2-hydroxyethyl)indole-3-sulfonamide.

Another embodiment relates to any "Example Compound" 1-1 to 1-36 as specifically disclosed herein.

Another preferred embodiment relates to compounds having a structure of Formula I, Ia, Ib, Ic, II, IIa, IIb, IIc, III, IIIa, IIIb or IIIc or a compound specifically disclosed herein and comprising at least one $^{18}F$ isotope, preferably in the position of a fluorine atom as indicated in one of the compounds disclosed herein. By way of non-limiting example, in the compound 6-chloro-N-(6-chloro-2,5-difluoropyridin-3-yl)-1H-indole-3-sulfonamide, disclosed herein, at least one of the two fluorines may be represented by a $^{18}F$ isotope.

This applies likewise to other fluorine containing compounds described herein. These $^{18}F$ containing compounds can preferably be used as PET tracers.

Another preferred embodiment relates to compounds having a structure of Formula Formula I, Ia, Ib, Ic, II, IIa, IIb, IIc, III, IIIa, IIIb or IIIc or a compound specifically disclosed herein and comprising at least one $^{11}C$ isotope, preferably in the position of a carbon atom as indicated herein. These $^{11}C$ containing compounds can preferably be used as PET tracers.

Another preferred embodiment relates to compounds having a structure of Formula Formula I, Ia, Ib, Ic, II, IIa, IIb, IIc, III, IIIa, IIIb or IIIc or a compound specifically disclosed herein and comprising at least one $^{123}I$, $^{125}I$ or $^{131}I$ isotope, preferably in the position of a iodine atom as indicated herein. By way of non-limiting example, in the compound 6-chloro-N-(6-iodopyridin-3-yl)-1H-indole-3-sulfonamide, disclosed herein, the iodine may be represented by a $^{123}I$, $^{125}I$ or $^{131}I$ isotope. $^{123}I$, $^{125}I$ or $^{131}I$ containing compounds can preferably be used as SPECT tracers.

Therapeutic and Diagnostic Application

In one aspect, the invention relates to anyone of the compounds described herein, for use in therapy or diagnosis, particularly in the therapy of animals, in particular humans.

Because of their GPR17 modulating properties, the compounds of the present invention can be used as medicine, and may be used for the treatment and/or prevention of various diseases of the CNS system.

One embodiment of the present disclosure is thus a compound as described herein for use as a medicine, in particular for use as a medicine for the treatment and/or prevention of a GPR17-associated disease.

A GPR17 associated disease or disorder is disease which is associated with a dysfunction of the GPR17 signaling system such as, for example, an overexpression and/or overactivity of GPR17 receptors. Without wished to be bound by any theory, the activity of GPR17 may be increased, extended or otherwise altered in certain tissues, for example in oligodendrocyte progenitor cells (OPCs) or during maturation of oligondendrocytes, potentially due to activating endogeneous stimuli such as, for example, inflammation factors. High activity of GPR17 may prevent the differentiation of oligodendrocytes and an efficient myelination, thus promoting the emergence or further development of a myelination disease (see Chen et al, supra). Negative GPR17 modulators may thus promote myelination by decreasing or turning off GPR17 activity and by supporting OPC maturation into myelin-producing oligondendrocytes (see e.g. Simon et al, supra).

In one preferred aspect, the invention relates to anyone of the compounds described herein, for diagnosis or for use in the prevention or treatment of a disorder or syndrome selected from and/or associated with a myelination disorder, in particular a demyelination disorder, such as of the central nervous system. In one embodiment, the compounds of the present invention are for use in promoting, stimulating and/or accelerating remyelination in an animal in need thereof. In one embodiment, the remyelination associated with the administration of a compound of the present invention will prevent or treat a demyelination disease such as, but not limited to, multiple sclerosis.

Compounds of the present invention can also be useful in the treatment or prevention of a disorder or syndrome associated with brain tissue damage, a cerebrovascular disorder, and certain neurodegenerative diseases.

Neurodegenerative disorders have been recently associated strongly with a loss of myelination. Accordingly, it is believed that preserved oligodendroglial and myelin functionality is a crucial prerequisite for the prevention of axonal and neuronal degeneration (see e.g. Ettle et al, supra). Negative GPR17 modulators may thus represent an excellent treatment option for any neurodegenerative disease associated with demyelination and/or impacted myelination such as e.g. ALS, MSA, Alzheimer's disease, Huntington Disease or Parkinson's Disease.

In a particular preferred aspect, the compounds of the present invention can thus be used in the prevention and/or treatment of a peripheral or central myelination disorder, in particular of a myelination disorder of the central nervous system. In one aspect, the compounds of the present invention are use in the treatment and/or prevention and/or diagnosis of a myelination disorder by oral administration. In a preferred embodiment, the myelination disorder to be treated with the compounds of the present invention is a demyelination disorder.

Examples of such myelination disorders to be treated and/or prevented by the presently disclosed compounds are, in particular, multiple sclerosis (MS) including its various subforms,
neuromyelitis optica (also known as Devic's disease),
chronic relapsing inflammatory optic neuritis, acute disseminated encephalomyelitis,
acute haemorrhagic leucoencephalitis (AHL),
periventricular leukomalacia
demyelination due to viral infections, e.g. by HIV or progressive multifocal leucoencephalopathy,
central pontine and extrapontine myelinolysis,
demyelination due to traumatic brain tissue damage, including compression-induced demyelination, e.g. by tumors
demyelination in response to hypoxia, stroke or ischaemia or other cardiovascular diseases,
demyelination due to exposure to carbon dioxide, cyanide, or other CNS toxins
Schilder's disease,
Balo concentric sclerosis,
Perinatal encephalopathy, and
Neurodegenerative Diseases including, in particular,
Amyotrophic lateral sclerosis (ALS).
Alzheimer's disease (AD).
Multiple system atrophy
Parkinson's Disease
Spinocerebellar ataxia (SCA), also known as spinocerebellar atrophy
Huntington's Disease
psychiatric disorders such as schizophrenia and bipolar disorder (see e.g. Fields, Trends Neurosci 31, 2008, 361; Tkachev et al, Lancet 362, 2003, 798).
peripheral myelination diseases such as leukodystrophies, peripheral demyelinating neuropathies, Dejerine-Sottas syndrome or Charcot-Marie-Tooth disease The treatment or prevention of a CNS disease such as a demyelination disease, also includes the treatment of the signs and symptoms associated with such a disease.

For example, the use of the compounds of the present invention for the treatment and/or prevention of MS also includes the treatment and/or prevention of the signs and symptoms associated with MS such as negative effects on optic nerves (vision loss, double vision), dorsal columns (loss of sensation), corticospinal tract (spastic weakness), cerebellar pathways (incoordination, dysarthria, vertigo, cognitive impairment), medial longitudinal fasciculus (double vision on lateral gaze), spinal trigeminal tract (face numbness or pain), muscle weakness (impaired swallowing, control of the bladder or gut, spasms), or psychological effects associated with the underlying disease such as depression, anxiety or other mood disorders, general weakness or sleeplessness.

Hence, the compounds of the present invention are for use in treating signs and symptoms of a myelination disease, in particular a demyelination disease such as multiple sclerosis; such signs and symptoms of MS include but are not limited to the group of vision loss, vision impairment, double vision, loss or impairment of sensation, weakness such as spastic weakness, motor incoordination, vertigo, cognitive impairment, face numbness, face pain, impaired swallowing, impaired speech, impaired control of bladder and/or gut, spasms, depression, anxiety, mood disorders, sleeplessness, and fatigue.

In one preferred embodiment, the compounds of the present invention are for use in treating multiple sclerosis. MS is a heterogeneous myelination disease and can manifest itself in a variety of different forms and stages, including but not limited to Relapsing-Remitting MS, Secondary-Progressive MS, Primary Progressive MS, Progressive Relapsing MS, each depending on activity and disease progression. Hence, in one embodiment, the compounds of the present invention are for use in treating multiple sclerosis in its various stages and forms, as described herein.

In one aspect, the compounds of the present invention are for use in the treatment/or prevention of Neuromyelitis optica (also known as Devic's disease or Devic's syndrome). Neuromyelitis optica is a complex disorder characterized by inflammation and demyelination of the optic nerve and the spinal cord. Many of the associated symptoms are similar to MS and include muscle weakness, in particular of the limbs, reduced sensation and loss of bladder control.

In one aspect, the compounds of the present invention are for use in prevention and/or treating ALS. ALS has been associated recently with oligodendrocyte degeneration and increased demyelination, suggesting ALS as a target disease for negative GPR17 modulators (Kang et al, supra; Fumagalli et al, Neuropharmacology 104, 2016, 82).

In one aspect, the compounds of the present invention are for use in prevention and/or treating Huntington Disease. Huntington is well described to be associated with impacted myelination, (Bartzokis et al, supra; Huang et al, Neuron 85, 2015, 1212).

In one aspect, the compounds of the present invention are for use in prevention and/or treating multiple system atrophy. MSA was associated strongly with demelination recently (Ettle supra, Jellinger supra) suggesting remyelination strategies to treat or prevent MSA.

In one aspect, the compounds of the present invention are for use in prevention and/or treating Alzheimer's Disease. AD has been recently observed to be associated with increased cell death of oligodendronecytes and focal demyelination and to represent a pathological process in AD (Mitew et al, Acta Neuropathol 119, 2010, 567), One aspect of the present invention relates to a method of treatment of anyone of the diseases or disorders described herein, in particular of a myelination disease such as MS, Neuromyeltis optica, ALS, Chorea Huntington, Alzheimer's Disease or others, by administering to a subject in need thereof, including a human patient, a therapeutically effective amount of a compound of the present invention.

In another aspect, the compound of the present invention may be used in the prevention and treatment of a spinal cord injury, perinatal encephalopathy, stroke, ischemia, or a cerebrovascular disorder.

In one aspect, the invention relates to a method for the prevention and/or treatment of a syndrome or disorder associated with a myelination disorder, or with a disorder or syndrome associated with a brain tissue damage, which comprises administering to a patient in need thereof a therapeutically effective amount of a compound as described herein. A patient in need of such a treatment can be any patient who suffered brain tissue damage such as by mechanical, chemical, viral, or other trauma.

In one aspect, the invention relates to a method for the prevention and/or treatment of a syndrome or disorder associated with a myelination disorder, or with a disorder or syndrome associated with stroke or other brain ischemia, which comprises administering to a patient in need thereof a therapeutically effective amount of a compound as described herein. A patient in need thereof may be any patient that recently experienced a cerebral ischemia/stroke which may have been caused, for example, by the occlusion of a cerebral artery either by an embolus or by local thrombosis.

GPR17 has been also associated with food uptake, insulin control and obesity recently. According to various reports, negative modulators of GPR17 may be helpful for controlling food uptake and for treating obesity (see e.g. Ren et al, Diabetes 64, 2015; 3670.) Hence, one embodiment of the present invention relates to the use of the compounds herein for the prevention and/or treatment of obesity, and methods of treating obesity.

Moreover, the compounds of the present invention may be used for the treatment of prevention of tissues where GPR17 is expressed, such as e.g. heart, lung or kidney. In one embodiment, the compounds of the present invention can be used to treat or prevent ischaemic disorders of the kidney and/or the heart.

GPR17 has been also associated with pulmonary inflammation and asthma such as, for example, induced by house dust mite (Maekawa, J Immunol 2010, 185(3), 1846-1854). Hence, the compounds of the present invention may be used for the treatment of asthma or other pulmonary inflammation.

The treatment according to the present invention may comprise the administration of one of the presently disclosed compounds as "stand alone" treatment of a CNS disease, in particular of a myelination disease or disorder such as MS or ALS. Alternatively, a compound disclosed herein may be administered together with other useful drugs in a combination therapy.

In a non-limiting example, a compound according to the present invention is combined with another medicament for treating a myelination disease, such as MS, having a different mode of action, such as e.g. an anti-inflammatory or immunosuppressive drug. Such compounds include but are not limited to: (i) corticosteroids such as prednisone, methylprednison or dexamethasone, (ii) beta interferons such as interferon beta-1a, interferon beta-1b or peginterferon beta- 1a, (iii) anti-CD20 antibodies such as ocrelizumab rituximab and ofatumumab, (iv) glatiramer salts such as glatiramer acetate, (v) dimethyl fumarate, (vi) fingolimod and other sphingosine-1-phosphate receptor modulators such as ponesimod, siponimod, ozanimod or laquinimod, (vii) dihydro-orotate dehydrogenase inhibitors such as teriflunomide or leflunomide, (viii) anti-integrin alpha4 antibodies such as natalizumab, (ix) anti CD52 antibodies such as alemtuzumab, (x) mitoxantrone, (xi) anti Lingo1 antibodies such as opicinumab, or (xii) other immunomodulatory therapies such as masitinib.

Likewise, a compound of the present invention can be combined with an analgesic drug if a painful myelination condition is to be treated. Also, a compound of the present disclosure may be used in combination with an antidepressant to co-treat psychological effects associated with the underlying myelination disease to be treated.

In combination therapies the two or more active principles may be provided via the same Formulation or as a "kit of parts", i.e. in separate galenic units. Also, the two or more active principles, including the compounds of the present invention, may be administered to the patient at the same time or subsequently, e.g. in an interval therapy. The additional drug may be administered by the same mode or a different mode of administration. For example, the GPR17 modulator of the present invention may be administered orally, while the second medicament may be administered by subcutaneous injection.

In one aspect, the compounds of the present invention may be used for the diagnosis and/or monitoring of a GPR17-related disease, as further described herein, in particular of a demyelinating disease, as disclosed herein, preferably in the diagnosis and monitoring of multiple sclerosis.

In one aspect, the compounds of the present invention can be used to diagnose and/or monitor the expression, distribution and/or activation of the GPR17 receptor either in-vivo, e.g. directly in a subject, such as using molecular imaging techniques, or in-vitro, such as e.g. by examining any samples such as body fluids or tissues taken from a subject. Any such determination of the GPR17 activity, expression and/or distribution may be used to predict, diagnose and/or monitor (a) the status and progression of a GPR17-associated disease as described herein, in particular a myelination disease including but not limited to, for example, multiple sclerosis, and (b) the efficacy and/or applicability and/or proper dosing of a treatment associated with any such GPR17-associated disease.

In one aspect, the compounds of the present invention may be used as PET or SPECT tracers, as further disclosed herein, in order to perform in-vivo diagnosis and/or disease monitoring. By this, the expression, activation and/or distribution of a GPR17 receptor may be directly measured in a subject, e.g. by imaging of a human patient after the administration of a GPR17 PET or SPECT tracer of the present invention. This may facilitate a proper diagnosis of the disease, can help to determine applicable treatment options and/or may be used to monitor disease progression and/or to monitor or predict the success of a medical intervention, including the selection and proper administration and/or dosing of a therapeutic drug.

In one embodiment, the PET or SPECT tracers of the present invention may be used in conjunction with a therapeutic drug, i.e. as a Companion Diagnostic, in order to monitor and/or predict the efficacy and/or safety of said therapeutic drug in a particular subject, or to estimate a drug's proper dosage.

One embodiment relates to a PET or SPECT tracer of the present invention for use as a Companion Drug in conjunction with a therapeutic drug. The therapeutic drug to be used with the PET or SPECT tracer of the present invention may be selected from the group of (a) an unlabeled compound of the present invention, (b) a GPR17 modulating compound which is different from the compounds of the present invention and (c) a drug for the treatment of a myelination disease, including but not limited to a drug for use in multiple sclerosis treatment, which is not a GPR17 modulator, as further described herein.

One embodiment relates to a kit comprising (a) as a first component, a PET or SPECT tracer of the present invention, in particular a PET or PET tracer based on a compound having a structure according to anyone of Formula I, Ia, Ib, Ic, II, IIa, IIb, IIc, III, IIIa, IIIb and IIIc, as further defined herein, or having a structure of any one of the compounds disclosed herein, but having incorporated at least one radionuclide which is suitable for PET or SPECT imaging, preferably a radionuclide selected from $^{18}$F, $^{11}$Cl, $^{123}$I, $^{125}$I and $^{131}$I, (b) as a second component, a therapeutic drug selected from among
   i. a compound of the present invention having a structure according to anyone of Formula I, Ia, Ib, Ic, II, IIa, IIb, IIc, III, IIIa, IIIb and IIIc, as further defined herein, or having a structure of anyone of the individual compounds disclosed herein, and having no radionuclide incorporated,
   ii. a GPR17 modulating compound which is different from the compounds of the present invention as defined in (i), and
   iii. a drug for the treatment of a myelination disease, including but not limited to a drug for use in multiple sclerosis treatment, but having no GPR17 modulating activity; such compounds are known to a person skilled in the art including those examples further described above.

Alternatively, the compounds of the present invention may be used in an in-vitro diagnostic assay, for example for the examination of suitable body fluids of a subject such as e.g. blood, plasma, urine, saliva, or cerebrospinal fluid for any level of GPR17 expression, activity and/or distribution.

One embodiment relates to a method of treating a GPR17 associated disease, in particular a myelination disease including but not limited to multiple sclerosis, wherein said method includes the steps of (a) determining the expression, activity and/or distribution of the GPR17 receptor of a subject, (b) comparing the expression, activity and/or distribution of the GPR17 receptor in said subject with the expression, activity and/or distribution of the GPR17 receptor in one or more healthy subjects or a population, (c) determining the need for medical treatment or prophylaxis of said subject based on a deviation of expression, activity and/or distribution of GPR17 of said subject from healthy subjects or a population and (d) treating the subject with the deviation of expression, activity and/or distribution of the GPR17 receptor by administering a therapeutic drug to said individual, which drug is suitable for the treatment of GPR17 associated diseases or disorders, in particular by administering a GPR17 modulator, preferably by administering one of more of the compounds of the present invention. In one embodiment, the determination (a) of the GPR17 expression, activity and/or distribution will be conducted using one of the compounds of the present invention, in particular with a PET or SPECT tracer, or by an in vitro examination of body fluids or tissue of said subject using a PET or SPECT tracer of the present invention.

In one preferred aspect, the invention relates to a pharmaceutical composition comprising a compound as described herein, and a pharmaceutical acceptable carrier.

For the administration as a medicinal drug, the compounds may be used in pharmaceutical composition comprising a compound of the present disclosure, and a pharmaceutically acceptable carrier, as further defined herein. Such a pharmaceutical composition can be adapted for example for oral, intravenous, intramuscular, subcutaneous, nasal, rectal, intracranial, ophthalmic, buccal or transdermal administration and may comprise pharmaceutically acceptable carriers, adjuvants, diluents, stabilizers and the like.

For instance, the compounds of the present invention may be dissolved in oils, propylene glycol or other solvents which are commonly used to produce an injection. Suitable examples of the carriers include, but not limited to, physiological saline, polyethylene glycol, ethanol, vegetable oils, isopropyl myristate, etc. The compounds of the present invention may be formulated into injections by dissolving, suspending or emulsifying in water-soluble solvent such as saline and 5% dextrose, or in water-insoluble solvents such as vegetable oils, synthetic fatty acid glyceride, higher fatty acid esters and propylene glycol. The formulations of the invention may include any of conventional additives such as dissolving agents, isotonic agents, suspending agents, emulsifiers, stabilizers and preservatives.

In one embodiment, the compounds of the present invention may be administered orally, e.g. in the form of a tablet, a capsule, a drage', a powder, a granulate, or in form of a liquid or a semi-solid, including e.g. syrups, suspensions, emulsions or solutions, by way of non-limiting example.

Oral formulations may contain, without limitation, sustained release agents, disintegrants, fillers, lubricants, stabilizers, antioxidants, flavours, dispersion agents, electrolytes, buffers, dyes, or conservation agents. Suitable excipients and formulations are known to those skilled in the art and are disclosed in standard monographs, such as Remington ("The science and practice of pharmacy", Lippincott, Williams & Wilkins, 2000) or disclosed in other sources well known to persons skilled in the art.

A tablet can, for example, be prepared by mixing at least one compound of the present invention with at least one non-toxic pharmaceutically acceptable excipient, such as e.g. binder, filler/diluents, disintegrant agents, plastisizer, and the like, and an optional solvent (aqueous or non aqueous), and by subsequent processing the mixture to a tablet by a process including but not limited to dry compression, dry granulation, wet granulation, spray drying, or melt extrusion. A tablet can either be uncoated, or coated by known techniques to either mask the bad taste of an unpleasant tasting drug, or delay disintegration and absorption of the active ingredient in the gastrointestinal tract.

A tablet may provide an immediate release or sustained release of the compounds of the present invention.

Typical sustained release agents are for example those that swell upon contact with water such as polyvinylpyrrolidone, hydroxyethylcellulose, hydroxypropylcellulose, other cellulose ethers, starch, pregelatinised starch, polymethacrylate, polyvinylacetate, microcrystalline cellulose, dextrans, and mixtures of these. Non-limiting examples of disintegrants include pregelatinised starch, sodium starch glycolate, microcrystalline cellulose, oxomethylcellulose sodium (CMC-Na), cross-linked CMC-Na, and low-substituted hydroxypropylcellulose, as well as mixtures thereof. Suitable fillers and binders include without limitation microcrystalline cellulose, powdered cellulose, lactose (anhydrous or monohydrate), compressible sugar, starch (e.g. corn starch or potato starch), pregelatinised starch, fructose, sucrose, dextrose, dextrans, other sugars such as mannitol, maltitol, sorbitol, lactitol and saccharose, siliconised microcrystalline cellulose, calcium hydrogen phosphate, calcium hydrogen phosphate dihydrate, dicalciumphosphate dihydrate, tricalciumphophate, calcium lactate or mixtures thereof. Lubricants, antiadherents and/or glidants include stearic acid, magnesium stearate, calcium stearate, sodium lauryl sulphate, hydrogenated vegetable oil, hydrogenated castor oil, sodium stearyl fumarate, macrogols, glycerol dibehenate, talc, corn starch, silicon dioxide, and the like, including mixtures.

The compound of the present invention may also be formulated for parenteral administration by injection, e.g. by bolus injection or infusion. The compositions for injection may be provided ready to use and may take such forms as suspensions, solutions, or emulsions in oily or aqueous vehicles, and may contain excipients such as suspending, stabilising, preserving and/or dispersing agents. Alternatively, the active ingredient may be in powder form for constitution with a suitable vehicle, e.g. sterile pyrogen-free water or saline, before use.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

In one embodiment, the compounds maybe administered transdermally. This mode of administration prevents the so-called $1^{st}$ pass effect of oral administration and moreover allows providing more constant plasma levels which is of particular advantage in some instances. The design of transdermal forms such as ointments or creams or other transdermal systems such as e.g. patches or electrophoretic devices is generally known from the art, see e.g. Venkatraman and Gale, Biomaterials 1998, Vol 19, p 1119; Prausnitz and Langer, Nat Biotechnology 2008, Vol 26.11 p 1261; WO 2001/47503; WO2009/000262; WO99/49852; WO 07/094876.

The preferable dose level of the compounds according to the present invention depends upon a variety of factors including the condition and body weight of the patient, severity of the particular disease, dosage form, and route and period of administration, but may appropriately be chosen by those skilled in the art. In various embodiments, the compounds are administered in an amount ranging from 0.001 to 10 mg/kg of body weight per day, or from 0.03 to 1 mg/kg of body weight per day. Individual doses may range from about 0.1 to 1000 mg of active ingredient per day, from about 0.2 to 750 mg/day, from about 0.3 to 500 mg/day, from 0.5 to 300 mg/day, or from 1 to 100 mg/day. Doses may be administered once a day, or several times a day with each divided portions.

Another aspect of the present invention is a Kit comprising a medicine or a pharmaceutical composition as described herein, and instructions for its use.

Definitions

Any reference to a compound according to the present invention also includes pharmaceutically acceptable salts, solvates, isotopes and co-crystals of such compounds unless expressly indicated otherwise.

The term "pharmaceutically acceptable salts" relates to any salts that the compounds may form and which are suitable for administration to subjects, in particular human subjects, according to the present invention. Such salts include but are not limited to acid addition salts, formed either with inorganic acids such as hydrochloric acid, hydrobromic acid, sulfuric acid, nitric acid, phosphoric acid, and the like, or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]oct-2-ene-1-6arboxyic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid. Other salts include 2,2-dichloroacetate, adipate, alginate, ascorbate, aspartate, 2-acetamidobenzoate, caproate, caprate, camphorate, cyclamate, laurylsulfate, edisilate, esylate, isethionate, formate, galactarate, gentisate, gluceptate, glucuronate, oxoglutarate, hippurate, lactobionate, napadisilate, xinafoate, nicotinate, oleate, orotate, oxalate, palmitate, embonate, pidolate, p-aminosalicylate, sebacate, tannate, rhodanide, undecylenate, and the like; or salts formed when an acidic proton present in the parent compound is replaced, such as with ammonia, arginine, benethamine, benzathine, calcium, choline, deanol, diethanolamine, diethylamine, ethanolamine, ethylendiamine, meglumine, glycine, hydrabamine, imidazole, lysine, magnesium, hydroxyethylmorpholine, piperazine, potassium, epolamine, sodium, trolamine, tromethamine or zinc.

The present invention includes within its scope solvates of the compounds as defined herein. "Solvates" are crystals formed by an active compound and a second component (solvent) which, in isolated form, is liquid at room temperature. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds herein may be formed with water, in which case they will be hydrates.

The present invention also includes co-crystals within its scope. The term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity. Examples of co-crystal formers, which may be present in the co-crystal alongside the active pharmaceutical ingredient, include L-ascorbic acid, citric acid, glutaric acid, cinnamic acid, mandelic acid, urea and nicotinamide.

The invention also includes all suitable isotopic variations of a compound of the invention. An "isotopic variation", or shortly "isotope" of a compound of the invention is defined as one in which at least one atom is replaced by an atom having the same atomic number but an atomic mass different from the atomic mass usually found in nature with the most abundant isotope(s) being preferred. Examples of isotopes that can be incorporated into compounds of the invention include isotopes of hydrogen, carbon, nitrogen, oxygen, sulphur, fluorine and chlorine such as $^2$H, $^3$H, $^{11}$C, $^{13}$C, $^{14}$C, $^{15}$N, $^{17}$O, $^{18}$O $^{35}$S, $^{18}$F, and $^{36}$Cl, respectively. Certain isotopic variations of the invention, for example, those in which a radioactive isotope such as $^3$H or $^{14}$C is incorporated, are useful in drug and/or substrate tissue distribution studies. Tritiated, i.e., $^3$H, and carbon-14, i.e., $^{14}$C, isotopes are particularly preferred for their ease of preparation and detectability. Further, substitution with isotopes such as deuterium, i.e., $^2$H, may afford certain therapeutic advantages resulting from greater metabolic stability, for example, increased in vivo half-life, reduced dosage requirements and hence may be preferred in some circumstances. Isotopic variations of the compounds of the invention can generally be prepared by conventional procedures using appropriate isotopic variations of suitable reagents.

Also part of the invention are those compounds wherein at least one atom has been replaced by a radioactive isotope (radioisotope) of the same or a different atom that can be used in vivo imaging techniques such as single-photon emission computed tomography (SPECT) or positron emission tomography (PET).

Examples for such isotopic variations of GPR17 modulators usable in SPECT studies (such compounds herein "SPECT tracers") are compounds wherein a $^{99m}$Tc, $^{111}$In, $^{82}$Rb, $^{137}$Cs, $^{123}$I, $^{125}$I, $^{131}$I, $^{67}$Ga, $^{192}$Ir or $^{201}$Tl, and preferably 123I, $^{99m}$Tc or $^{111}$In have been introduced. For example, in order for the compounds of the present invention to be used as SPECT tracers, an $^{123}$I isotope may be introduced into a GPR17 modulator as disclosed herein. By way of a non-limiting example, in order for a compound to be used as SPECT tracer, a radionuclide selected from $^{123}$I, $^{125}$I and $^{131}$I may be introduced into a compound of the present invention. In one embodiment, a SPECT tracer of the present invention may be based on the structure of a halogen-containing GPR17 modulator disclosed herein, wherein one of the radionuclides $^{123}$I, $^{125}$I and $^{131}$I has been introduced into the position of a halogen, preferably, a iodine atom.

Accordingly, the term "SPECT tracer of the present invention", relates to compounds as described in the present patent application and having a structure according to anyone of Formula I, Ia, Ib, Ic, II, IIa, IIb, IIc, III, IIIa, IIIb and IIIc as further defined herein, or as otherwise individually disclosed herein, wherein at least one radioisotope has been introduced which is suitable for SPECT imaging. This includes but is not limited to $^{99m}$Tc, $^{111}$In, $^{82}$Rb, $^{137}$Cs, $^{123}$I, $^{125}$I, $^{131}$I, $^{67}$Ga, $^{192}$Ir or $^{201}$Tl. Preferred isotopes used in the SPECT tracers of the present invention are $^{123}$I, $^{99m}$Tc or $^{111}$In, in particular $^{123}$I.

Examples for GPR17 modulator derivatives usable in PET applications (herein "PET tracers") are compounds wherein $^{11}$C, $^{13}$N, $^{15}$O, $^{18}$F, $^{76}$Br, $^{124}$I, $^{82}$Rb or $^{68}$Ga have been introduced. For example, in order for a compound to be used as a PET tracer, an $^{18}$F isotope may be introduced into a compound of the present invention. In one embodiment, a PET tracer may be based on the structure of a fluorine-containing GPR17 modulator disclosed herein, wherein the respective radionuclide $^{18}$F has been introduced into the position of the fluorine atom. This likewise applies to the introduction of at least one $^{11}$C, $^{13}$N $^{15}$O, $^{76}$Br or $^{124}$I instead of an "unlabelled" carbon, nitrogen, oxygen, bromine, or iodine atom, respectively (see e.g. Pimlott and Sutherland, Chem Soc Rev 2011, 40, 149; van der Born et al, Chem Soc Rev 2017, 46, 4709).

Accordingly, the term "PET tracer of the present invention", relates to compounds as described in the present patent application and having a structure according to any-one of Formula I, Ia, Ib, Ic, II, IIa, IIb, IIc, III, IIIa, IIIb and IIIc as further defined herein, or as otherwise individually disclosed herein, wherein at least one radioisotope has been introduced which is suitable for PET imaging. This includes but is not limited to $^{11}$C, $^{13}$N $^{15}$O, $^{18}$F, $^{76}$Br or $^{124}$I. Preferred PET nucleotides for use in the compounds of the present invention are $^{11}$C, $^{13}$N, $^{15}$O, $^{18}$F, in particular $^{18}$F.

The present invention includes within its scope prodrugs of the compounds of the present invention. In general, such prodrugs will be functional derivatives of the compounds described herein which are readily convertible in vivo, e.g. by endogenous enzymes in the gut or the blood, into the required GPR17 modulating compounds described herein. Conventional procedures for the selection and preparation of suitable prodrug derivatives are described, for example, in Design of Prodrugs, ed. H. Bundgaard, Elsevier, 1985.

Depending on its substitution pattern, the compounds of the present invention may or may not have one or more optical stereocenters, and may or may not exist as different enantiomers or diastereomers. Any such enantiomers, diastereomers or other optical isomers are encompassed by the scope of the invention.

The compound of the present invention may also exist in different crystal forms, i.e. as polymorphs, all of which are encompassed by the present invention.

The compounds of the present invention may be included in a pharmaceutical composition which may also include a pharmaceutically acceptable carrier.

"Pharmaceutically acceptable carrier" refers to a diluent, adjuvant, excipient, or carrier, or other ingredient with which a compound of the invention is administered and which a person of skilled in the art would understand to be pharmaceutically acceptable.

The compounds of the present invention are useful in the prevention and/or treatment of certain diseases or disorders in animals, in particular in humans, as described herein.

"Preventing" or "prevention" refers to a reduction in risk of acquiring a disease or disorder (i.e., causing at least one of the clinical symptoms of the disease not to develop in a subject, in particular a human subject, that may be exposed to or predisposed to the disease but does not yet experience or display symptoms of the disease).

"Treating" or "treatment" of any disease or disorder includes, in one embodiment, to improve the disease or disorder (i.e., arresting or reducing the development of the disease or at least reducing one of the clinical symptoms of the disease). In another embodiment "treating" or "treatment" refers to improve at least one physical parameter, which may or may not be discernible by the subject, in particular a human subject, but which is based on or associated with the disease or disorder to be treated. In yet another embodiment, "treating" or "treatment" refers to modulating or alleviating the disease or disorder, either physically (e.g. stabilization of a discernible on non-discernible symptom), physiologically (e.g. stabilization of a physiological parameter), or both. In yet another embodiment, "treating" or "treatment" refers to delaying the onset or progression of the disease or disorder. Accordingly, "treating" or "treatment" includes any causal treatment of the underlying disease or disorder (i.e. disease modification), as well as any treatment of signs and symptoms of the disease or disorder (whether with or without disease modification), as well as any alleviation or amelioration of the disease or disorder, or its signs and symptoms.

"Diagnosis", "diagnoses" or "diagnosing" of a disease or disorder include, in one embodiment, the identification and measurement of signs and symptoms which are associated with said disease. "Diagnosis", "diagnoses" or "diagnosing" include but are not limited to the detection and/or measurement of decreased, increased, or otherwise incorrectly (e.g. as to time or place) expressed, activated, or distributed GPR17 receptors as indicator of a GPR17-related disease or disorder, as compared to healthy subjects. In one example, GPR17 ligands may be used in the form of PET or SPECT tracers for such a diagnosis, including a diagnosis for a myelination disease.

The terms "disease(s)" and "disorder(s)" are used largely interchangeably herein.

"Monitoring" refers to the observation of a disease, condition or at least one medical parameter over a certain period of time. "Monitoring" also includes the observations of the effects of a therapeutic drug with the assistance of a "Companion Drug".

"Companion Diagnostic" as used herein refers to a compound that can be used in conjunction to a therapeutic drug with the aim to determine the applicability (e.g. in terms of safety and efficacy) of said therapeutic drug to a specific patient. The use of a "Companion Diagnostic" may include diagnostic and monitoring steps.

The term "animal(s)" and "subject(s)" includes humans. The terms "human," "patient" and "human subject" are typically used interchangeably herein, unless clearly indicated.

The invention also relates to methods of treating an animal disease or disorder, as described in more detail herein, in particular a human disease or disorder, which includes the administration of the compounds of the present invention in therapeutically effective amounts. "Therapeutically effective amount" means the amount of a compound that, when administered to a subject, in particular a human subject, for treating a disease, is sufficient to effect such treatment for the disease. The "therapeutically effective amount" can vary depending on the compound, the disease and its severity, and the condition, age, weight, gender etc. of the subject, in particular a human subject, to be treated.

The term "multiple sclerosis" as used herein refers to the disease as classified in Section G35 of the ICD-10-CM diagnosis code of the 2018 American edition.

The term "GPR17 modulators" as used herein are meant to describe compounds that are capable of modulating the activity of the GPR17 receptor, in particular compounds that are capable of decreasing the GPR17 activity. Such "negative GPR17 modulators" include GPR17 antagonists which are capable of blocking the effects of GPR17 agonists, as well as GPR17 inverse agonists which are also capable of inhibiting constitutional active GPR17 receptors or receptor variants. Preferred GPR17 modulators of the present invention are inverse GPR17 agonists.

"Halogen" includes fluorine, chlorine, bromine, and iodine atoms.

"Cyano" refers to the group —C≡N.

"Azido" refers to the group —N=N=N.

"Oxo" refers to the group —C(=O)OH

"Oxo" refers to the group —C(=O)—

Whenever numbers appear in subscript following a "C", these numbers (whether in brackets or not) refer to the range of carbon atoms comprised by the respective group directly following the numbers. For example, "$C_{1-3}$" and "$(C_{1-3})$" both refer to a group, as further specified herein, which comprises between 1 and 3 C-Atoms.

"Alkyl" includes saturated aliphatic hydrocarbyl groups. The hydrocarbon chain may be either straight-chained or branched. Examples of "alkyl" include those with 1-5 carbon atoms ("$C_{1-5}$ alkyl"), 1-4 carbon atoms ("$C_{1-4}$ alkyl"), 1-3 carbon atoms ("$C_{1-3}$ alkyl"), or 1-2 carbon atoms ("$C_{1-2}$ alkyl"). This term is exemplified by groups such as methyl, ethyl, n-propyl, isopropyl, n-butyl, sec-butyl, isobutyl, tert-butyl, t-amyl, and the like. Any numbers of C atoms in alkyls or other groups may be indicated herein in brackets or without brackets.

"Alkyloxy" and "alkoxy", as used interchangeably herein (together alk(yl)oxy), include the group —OR wherein R is "alkyl" as defined and exemplified further herein. Particular alk(yl)oxy groups include, by way of example, meth(yl)oxy, eth(yl)oxy, n-prop(yl)oxy, isoprop(yl)oxy, n-but(yl)oxy, tert-but(yl)oxy, sec-but(yl)oxy, isobut(yl)oxy, and the like.

The term "fluoroalkyl" as used refers to an "alkyl" as described herein, which is substituted with one or more fluorine atoms. Representative examples of fluoro($C_{1-3}$) alkyl groups include, but are not limited to —$CF_3$, —$CHF_2$, —$CHFCHF_2$ and —$CH_2CF_3$. A particularly preferred fluoroalkyl group is difluoromethyl —$CHF_2$.

The terms "fluoroalkyloxy" or "fluoroalkoxy" as interchangeably used herein refer to an "alk(yl)oxy" as described herein, which is substituted with one or more fluorine atoms. Representative examples of fluoro($C_{1-3}$)alk(yl)oxy groups include, but are not limited to —$OCF_3$, —$OCHF_2$, —$OCHFCH_2F$ and —$OCH_2CF_3$.

The term "fluoromethoxy" as used herein refers to a methoxy group which is substituted with one to three fluorine atoms. The term "monofluoromethoxy" refers to a methoxy group which is substituted with one fluoro atom. The term "difluoromethoxy" as used herein refers to a methoxy group which is substituted with two fluorine atoms. The term "trifluoromethoxy" refers to a methoxy group which is substituted with three fluorine atoms.

The term "fluoroethoxy" as used herein refers to an ethoxy group which is substituted with one to three fluorine atoms. The term "monofluoroethoxy" as used herein refers to an ethoxy group which is substituted with one fluorine atom. A particularly preferred monofluoroethoxy is the group —$OCH_2CH_2F$. The term "difluoroethoxy" as used herein refers to an ethoxy group which is substituted with two fluorine atoms. A particularly preferred difluoroethoxy is the group —$OCH_2CHF_2$. The term "trifluoroethoxy" refers to an ethoxy group which is substituted with three fluorine atoms. A preferred trifluoroethoxy group is the group —$OCH_2CF_3$.

The term "fluoromethoxyethoxy" refers to a terminal fluoromethoxy group as further defined herein which is attached to an ethoxy group. A preferred "fluoromethoxyethoxy" is difluoromethoxyethoxy, which is represented by —$OCH_2CH_2OCHF_2$.

The term "hydroxyalkyl" as used refers to an "alkyl" (e.g. a methyl, ethyl or propyl group) as described herein, which is substituted with one or more hydroxy groups. Representative examples of hydroxy($C_{1-3}$)alkyl groups include, but are not limited to —$CH_2CH_2OH$ (monohydroxyethyl) —$CH_2CH_2CH_2OH$ (monohydroxypropyl), and —$CH_2CH(OH)CH_2OH$ (dihydroxypropyl).

The term "hydroxyalk(yl)oxy" as used refers to an "alk(yl)oxy" as described herein, which is substituted with one or more hydroxy groups. Representative examples of hydroxy($C_{1-3}$)alkyl groups include, but are not limited to —$OCH_2CH_2OH$ (monohydroxyethoxy) and —$OCH_2CH_2CH_2OH$ (monohydroxypropyloxy).

The term "fluorohydroxyalkyl" or "fluorohydroxyalkoxy" as used herein refers to an alkyl or alkoxy group, respectively, as defined herein, with the amount of C-atoms as specified, which are substituted with at least one hydroxy group and at least one fluoroatom. Preferred examples are groups which are substituted with one hydroxy and one to three fluoro atoms such as trifluoromonohydroxypropyl (such as e.g. $CH_2CH(OH)CF_3$) monofluoromonohydroxypropyl (such as e.g. —$CH_2CHFCH_2OH$ or —$CH_2CH(OH)CH_2F$) and the like.

The term "cycloalkyl" as used herein refers to a monovalent group derived from a saturated hydrocarbon, which may be unsubstituted or substituted with one or more substituents as further indicated herein. The "cycloalkyl" is comprised of at least three up to, for example, 5 ring forming carbon atoms ("$C_{3-5}$ cycloalkyl"), or 4 ring forming atoms ("$C_{3-4}$ cycloalkyl"). Suitable cycloalkyl groups include cyclopropyl, cyclobutyl, and cyclopentyl.

The term "heterocycloalkyl" as used herein refers to saturated ring containing at least two ring forming carbon atoms and at least one ring forming heteroatom preferably selected from oxygen, sulphur and nitrogen, wherein each ring which may be unsubstituted or further substituted with one or more substituents as described herein. The term "$C_{3-5}$ heterocycloalkyl" refers to a heterocycoalkyl comprising between three to five ring forming atoms. Suitable heterocycloalkyl groups include epoxide, oxetanyl, azetidinyl, tetrahydrofuranyl, dioxolanyl, pyrrolidinyl, oxazolidinyl, thiazolidinyl, isothiazolidinyl and imidazolidinyl. Preferred heterocycloalkyls are those containing one oxygen atom such as oxetanyl or tetrahydrofuranyl.

EXPERIMENTAL SECTION

Experimental Part

A. Chemistry

The compounds of the present invention and their synthetic routes are described in more details below.

A-I General Methods of Making the Compounds

The compounds of Formula I according to the invention can be prepared analogously to conventional methods as understood by the person skilled in the art of synthetic organic chemistry.

Any reference to the synthesis of compounds of general Formula I herein likewise apply to the applicable compounds of the subgeneric Formula II, III, and the specific Example compounds disclosed herein.

According to one embodiment, some compounds of general Formula I may be prepared by reaction of a sulfonyl chloride of Formula XII with an aniline of Formula X according to the equation:

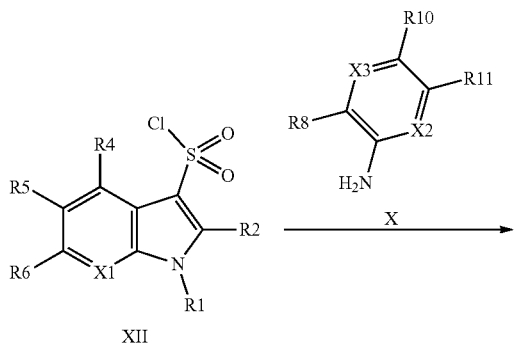

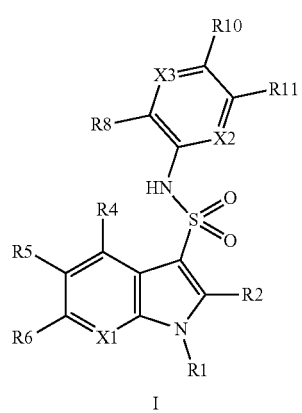

This reaction may be performed in the presence of a base such as pyridine used as solvent at room temperature or under heating at a temperature preferably ranging from 50 to 100° C. The use of a catalytic amount of a base such as DMAP can also be beneficial.

Compounds of Formula XII may be prepared by sulfonylchlorination of a compound of Formula XI according to the equation:

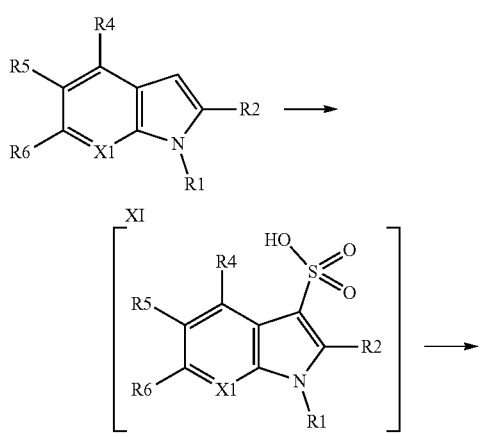

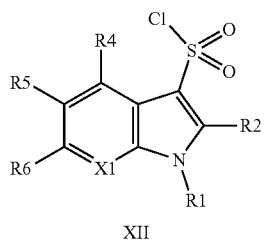

This reaction may be performed in the presence of a sulfonylchlorinating agent such as chlorosulfonic acid in a polar solvent such as acetonitrile at room temperature.

Alternatively, this reaction may be performed in the presence of a sulfonylating agent such as sulfur trioxide/DMF complex in a solvent such as dichloromethane at room temperature. The non-isolated sulfonic acid intermediate could be sequentially reacted with a chlorinating agent such as thionyle chloride at room temperature.

Compounds of Formula XI may be prepared by the alkylation of compounds of Formula IX by nucleophilic substitution with an akylating agent such as a iodo or a trifluoromethanesulfonate derivative in the presence of a base such as sodium hydride in a solvent like DMF at low or room temperature.

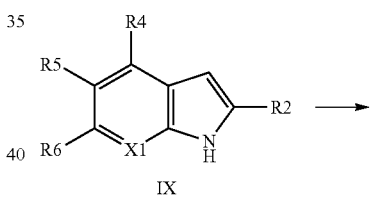

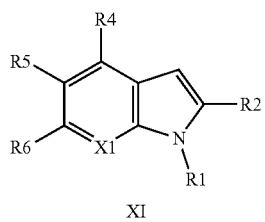

Alternatively, this reaction may be performed by Michael addition of compounds IX on an activated vinyl such as an acrylate in the presence of a base such as sodium hydride in a solvent like DMF at room temperature.

According to one embodiment, some compounds of general Formula I may be prepared by alkylation of compounds of Formula XIII-P1 wherein P1 is a protecting group such as a methoxymethyl according to the equation:

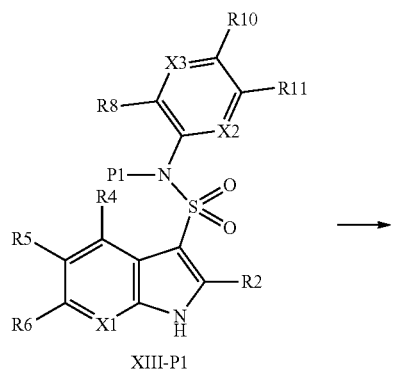

XIII-P1

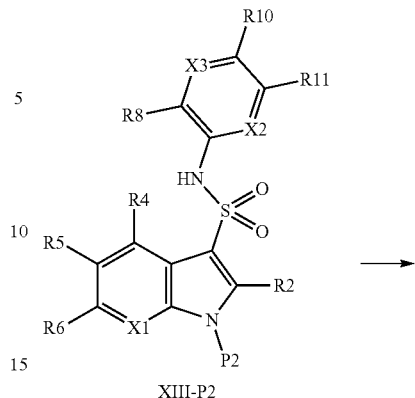

XIII-P2

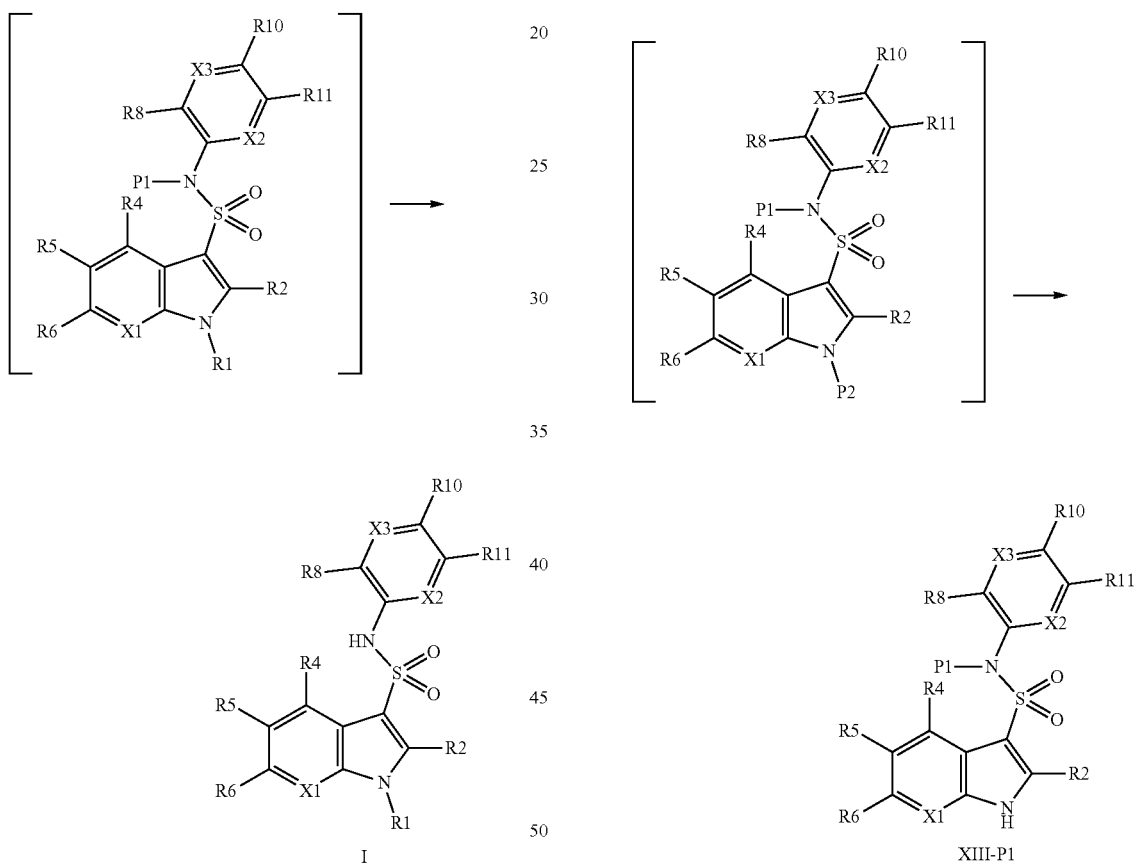

This reaction may be done in the presence of a base like potassium hydroxide in a polar solvent such as DMSO followed by the addition of an alkylating agent such as a iodo derivative under heating at temperature ranging from 50 to 120° C. The deprotection may be performed subsequently in acidic conditions such as concentrated hydrochloric acid in a solvent like methanol.

Compounds of Formula XIII-P1 wherein P1 is a protecting group such as a methoxymethyl may be prepared by a sequence of protection and deprotection of a compound of Formula XIII-P2 wherein P2 is a protecting group such as phenylsulfonyl (PhSO$_2$) according to the equation:

This reaction may be performed by the reaction of compounds XIII-P2 wherein P2 is a protecting group such as phenylsulfonyl with chloromethyl ether or similar reagent in the presence of a base like DIPEA in a solvent such as DCM at room temperature. The following deprotection of the P2 group can be done in the presence of tetrabutylammonium fluoride in a solvent such as THF under heating at a temperature preferably ranging from 60 to 90° C.

Compounds of Formula XIII-P2 wherein P2 is a protecting group such as phenylsulfonyl may be prepared by reaction of a sulfonyl chloride of Formula XII-P2 with an aniline of Formula X. This reaction may be performed in the presence of a base such as pyridine used as solvent at room temperature.

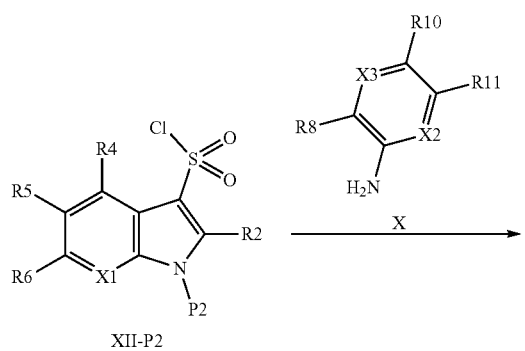

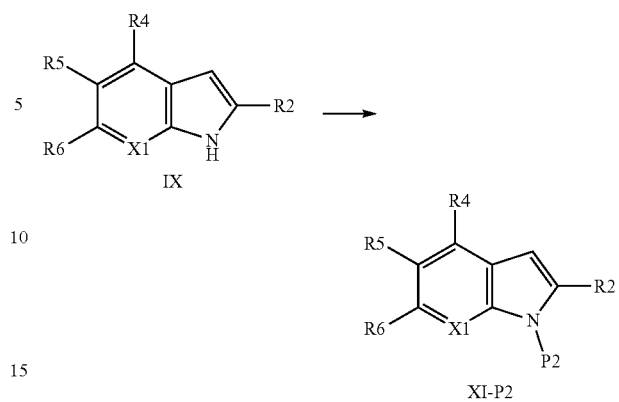

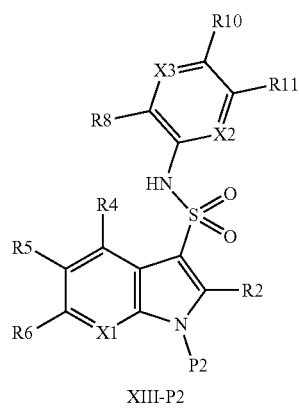

Compounds of Formula XII-P2 wherein P2 is a protecting group such as phenylsulfonyl may be prepared by chlorosulfonylation of a compound of Formula XI-P2 according to the equation:

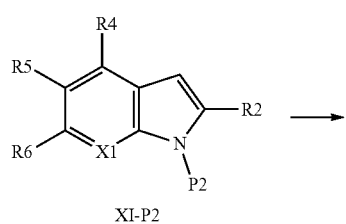

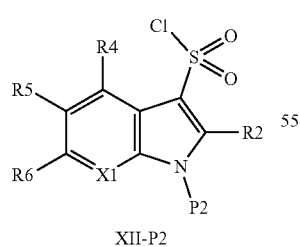

This reaction may be performed in the presence of chlorosulfonic acid in a polar solvent such as acetonitrile at room temperature.

Compounds of Formula XI-P2 wherein P2 is a protecting group such as phenylsulfonyl may be prepared by protection of a compound of Formula IX according to the equation:

This reaction may be performed by reacting compounds IX with benzenesulfonyle chloride or similar reagent in the presence of a base like sodium hydroxide or sodium iodide in a solvent such as DCM or DMF or according to any method known to the person skilled in the art.

Anilines of Formula X are commercially available or may be prepared according to any method known to the person skilled in the art or using procedures described in literature. Alternatively, some anilines of Formula X may be prepared by reduction of a compound VIII according to the equation:

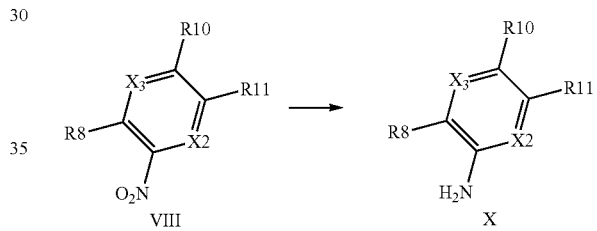

This reaction may be performed using any reducing agent such as iron in the presence of an acid such as acetic acid or hydrogen in the presence of a catalytic amount of palladium on charcoal in a polar solvent such as ethyl acetate or methanol or according to any method known to the person skilled in the art.

Compounds of Formula VIII are commercially available or may be prepared according to literature procedures or or any other methods known to the person skilled in the art.

Compounds of Formula IX are commercially available or may be prepared by suitable methods well known by the person skilled in the art.

A-II. Abbreviations/Recurrent Reagents

Ac: acetyl
ACN: Acetonitrile
AcOH: Acetic acid
Brine: Saturated aqueous sodium chloride solution
Boc: tert-butoxycarbonyl
nBu: n-butyl
tBu: tert-butyl
conc.: concentrated
Cy: Cyclohexyl
d: days
DCM: Dichloromethane
DIPEA: Diisopropylethylamine
DMAP: 4-dimethylaminopyridine DMF: N,N-Dimethylformamide
DMSO: Dimethylsulfoxide
ES+: Electrospray Positive Ionization
ES−: Electrospray Negative Ionization
ESI: Electrospray Ionization
EtOAc: Ethyl acetate
h: hours
LCMS: Liquid Chromatography Mass Spectrometry
Me: Methyl
MeOH: Methanol
min.: minutes
mw: microwave oven
NMR: Nuclear magnetic resonance
rt: room temperature
TBAHSA: Tetrabutylammonium hydrogen sulfate
TBAF: Tetrabutylammonium fluoride
TFAA: Trifluoroacetic anhydride
THF: Tetrahydrofuran
TLC: Thin Layer Chromatography A-III. Analytical Methods Commercial solvents and reagents were generally used without further purification, including anhydrous solvents when appropriate (generally Sure-Sea™ products from Aldrich Chemical Company or AcroSeal™ from ACROS Organics). In general reactions were followed by thin layer chromatography or Liquid Chromatography Mass Spectrometry analyses.

Mass spectrometric measurements in LCMS mode are performed using different methods and instruments as follows:

Basic LCMS Method 1:

Mass spectrometry (MS) spectra were recorded on an LCMS-2010EV mass spectrometer (Shimadzu) with electrospray ionization (ESI) coupled to an HPLC modular Prominence (Shimadzu) using Xbridge C18-2.1×30 mm, 2.5 μm (Waters) column. A volume of 3 μL of sample solution with a concentration of approx. 1 mg/mL was injected. The mobile phase for basic conditions was a mixture of A) 5 mM ammonium formate +0.1% ammonia in water B) 5% mobile phase A+0.1% ammonia in acetonitrile. The gradient used was as follows-5:95(B/A) to 95:5(B/A) in 4 min and hold 95:5(B/A) for next 1 min.

Neutral LCMS Method 2:

Mass spectrometry (MS) spectra were recorded on an LCMS instrument (Applied Biosystems API 2000 LC/MS/MS, HPLC Agilent 1100) using the following procedure: dissolving of the compounds at a concentration of 1.0 mg mL-1 in ACN (Solvent A) or water (containing 2 mM ammonium acetate):MeOH 90:10 (Solvent B), and if necessary sonicated until completely dissolved. Then, 10 μL of the solution was injected into a Phenomenex Luna C18 HPLC column (50×2.00 mm, particle size 3 μm) and elution was performed with a gradient of water:ACN (Gradient A) or water:MeOH (Gradient B) from 90:10 to 0:100 within 10 min, starting the gradient after 1 min, followed by elution in pure organic solvent for 10 min at a flow rate of 300 μL min-1. UV absorption was detected from 220 to 400 nm using a diode array detector (DAD).

Crude materials could be purified by normal phase chromatography or recrystallization.

Normal phase chromatography was performed using silica gel columns (100:200 mesh silica gel or cartridges for flash chromatography systems such as Isolera™ Four from Biotage® or Teledyne Isco CombiFlash®).

NMR spectra were recorded on different instruments:
a Varian 400 MHz NMR spectrometer with acquisition time (at)=2.0 sec, relaxation delay (d1)=2.0 sec and line broadening (Ib)=0.5 Hz.
a Bruker Avance III 600 MHz NMR spectrometer Chemical shifts are referenced to signals deriving from residual protons of the deuterated solvents (DMSO-$d_6$ or $CDCl_3$). Chemical shifts are given in parts per million (ppm) and coupling constants (J) in Hertz (Hz). Spin multiplicities are given as broad (br), singlet (s), doublet (d), triplet (t), quartet (q) and multiplet (m).

Products were generally dried under vacuum before final analyses and submission to biological testing.

A-IV: Example Compounds and Synthesis

The names of the following compounds are IUPAC names generated by Biovia Draw Version 16.1 for Intermediates of Formula X, XI, XII and by Pipeline Pilot 2018 using OpenEye oemetachem version 1.4.5 for Example compounds of Formula I.

INTERMEDIATES

When commercially available, starting materials are identified by their CAS Register Numbers.

A. Synthesis of Intermediates of Formula X

A.1. Synthesis of
6-chloro-5-fluoro-2-methoxy-pyridin-3-amine X-1

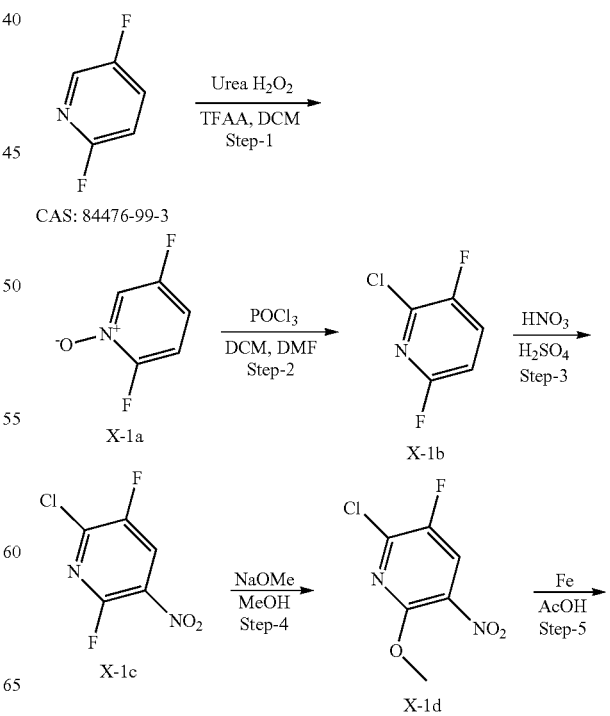

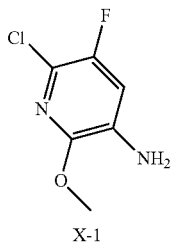

X-1

Step-1: Synthesis of 2,5-difluoro-1-oxido-pyridin-1-ium X-1a

To a solution of 2,5-difluoropyridine (3.00 g, 26.1 mmol) in DCM (120 mL) was added Urea hydrogen peroxide (7.36 g, 78.2 mmol) and the reaction mixture was stirred at room temperature for 10 min. The reaction mixture was cooled at 0° C. followed by drop wise addition of trifluoroacetic anhydride (12 mL). The reaction mixture was stirred at room temperature for 4 h. Progress of the reaction was monitored by TLC. After completion, the reaction mixture was diluted with aqueous NaHCO₃ (120 mL) and extracted with DCM (3×80 mL). The organic layer was separated, dried over anhydrous Na₂SO₄ and concentrated under vacuum to afford 2,5-difluoro-1-oxido-pyridin-1-ium X-1a (1.00 g) as an off-white solid.

This compound was used as such for the next reaction without further purification.

Yield: 29%.

¹H NMR (400 MHz, DMSO-d₆) δ 7.39-7.47 (m, 1H), 7.50 (m, 1H), 8.48-8.57 (m, 1H).

Step-2: Synthesis of 2-chloro-3,6-difluoro-pyridine X-1b

To a solution of 2,5-difluoro-1-oxido-pyridin-1-ium X-1a (0.95 g, 7.25 mmol) in DCM (30 mL) was added POCl₃ (1.33 mL, 14.5 mmol) drop wise at 0° C. The reaction mixture was stirred at same temperature for 5 min followed by addition of DMF (0.60 mL). The reaction mixture was stirred at room temperature for 6 h. Progress of the reaction was monitored by TLC. After completion, the reaction mixture was quenched with saturated NaHCO₃ (50 mL) solution and extracted with EtOAc (2×50 mL). The organic layer was separated, dried over anhydrous Na₂SO₄ and concentrated under vacuum to afford 2-chloro-3,6-difluoro-pyridine X-1b (0.65 g) as a pale brown liquid. This compound was used as such for the next reaction without further purification.

Yield: 60%.

¹H NMR (400 MHz, DMSO-d₆) δ 7.35-7.39 (m, 1H), 8.15-8.23 (m, 1H).

Step-3: Synthesis of 2-chloro-3,6-difluoro-5-nitro-pyridine X-1c

To a solution of 2-chloro-3,6-difluoro-pyridine X-1b (0.60 g, 4.01 mmol) in fuming HNO₃ (4.19 mL, 100 mmol) was added concentrated H₂SO₄ (3.21 mL, 60.2 mmol) drop wise maintaining a temperature below 40° C. The reaction mixture was then heated at 60° C. for 30 min. Progress of the reaction was monitored by TLC. After completion, the reaction mixture was cooled and poured into crushed ice and extracted with DCM (2×50 mL). The organic layer was separated, dried over anhydrous Na₂SO₄ and concentrated under vacuum. The crude obtained was purified by column chromatography (silica, 100-200 mesh, 10% EtOAc in hexane) to afford 2-chloro-3,6-difluoro-5-nitro-pyridine X-1c (0.185 g) as a pale yellow liquid.

Yield: 24%.

¹H NMR (400 MHz, DMSO-d₆) δ 9.10-9.14 (m, 1H).

Step-4: Synthesis of 2-chloro-3-fluoro-6-methoxy-5-nitro-pyridine X-1d

To a solution of 2-chloro-3,6-difluoro-5-nitro-pyridine X-1c (0.67 g, 3.44 mmol) in MeOH (10 mL) was added NaOMe (0.82 mL, 3.79 mmol) drop wise at −40° C. and the reaction mixture was stirred at same temperature for 20 min. Progress of reaction was monitored by TLC. After completion, the reaction mixture was poured into ice cold 1N HCl (10 mL) and extracted with hexane (2×15 mL). The organic layer was separated, dried over anhydrous Na₂SO₄ and concentrated under vacuum to obtain 2-chloro-3-fluoro-6-methoxy-5-nitro-pyridine X-1d (0.40 g) as a yellow solid.

This compound was used as such for next reaction without further purification.

Yield: 56%.

¹H NMR (400 MHz, DMSO-d₆) δ 4.03 (s, 3H), 8.82 (d, J=7.83 Hz, 1H).

Step-5: Synthesis of 6-chloro-5-fluoro-2-methoxy-pyridin-3-amine X-1

To a stirred solution of 2-chloro-3-fluoro-6-methoxy-5-nitro-pyridine X-1d (0.20 g, 0.97 mmol) in acetic acid (4 mL) was added iron (0.22 g, 3.87 mmol) at 0° C. The reaction mixture was stirred at room temperature for 2 h. Progress of reaction was monitored by TLC and LCMS. After completion, reaction mixture was poured in to ice cold saturated NaHCO₃ (25 mL). The reaction mixture was filtered through a pad of celite, washed with EtOAc (2×15 mL) and the aqueous layer was extracted with EtOAc (2×15 mL). The organic layer was separated, dried over anhydrous Na₂SO₄ and concentrated under vacuum. The crude obtained was purified by column chromatography (silica, 100-200 mesh, 4% EtOAc in hexane) to afford 6-chloro-5-fluoro-2-methoxy-pyridin-3-amine X-1 (0.11 g, 63%) as an off white solid.

Yield: 63%.

Basic LCMS Method 1 (ES⁺): 177 (M+H)⁺, 98% purity.

¹H NMR (400 MHz, DMSO-d₆) b 3.84 (s, 3H), 5.49 (brs, 2H), 6.90 (d, J=9.78 Hz, 1H).

A.2. Synthesis of 6-(difluoromethoxy)-5-fluoro-2-methoxy-pyridin-3-amine X-2

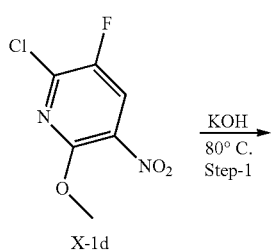

Step-1: Synthesis of 3-fluoro-6-methoxy-5-nitro-pyridin-2-ol X-2a

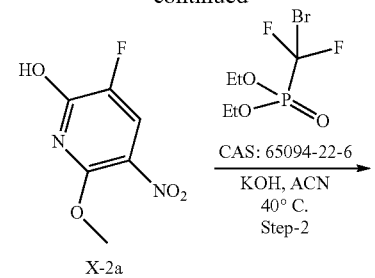

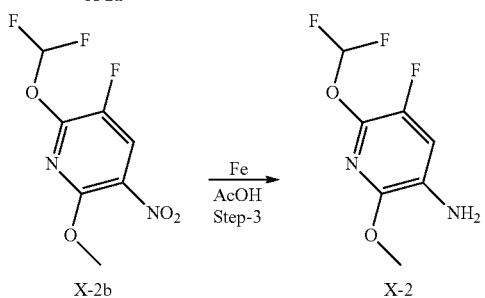

To a solution of 2-chloro-3-fluoro-6-methoxy-5-nitro-pyridine X-1d (0.90 g, 4.36 mmol) in H$_2$O (6 mL) was added KOH (0.61 g, 10.9 mmol) and the reaction mixture was heated at 80° C. for 16 h. Progress of reaction was monitored by TLC. After completion, the reaction mixture was diluted with H$_2$O (100 mL) and extracted with EtOAc (3×80 mL). The organic layer was separated, dried over anhydrous Na$_2$SO4 and concentrated under vacuum to afford 3-fluoro-6-methoxy-5-nitro-pyridin-2-ol X-2a (0.30 g crude) as a pale yellow solid.

This compound was used as such for the next reaction without further purification.

$^1$H NMR (400 MHz, DMSO-d$_6$) b 3.99 (s, 3H), 8.42 (d, J=9.60 Hz, 1H), 12.12 (s, 1H).

Step-2: Synthesis of 2-(difluoromethoxy)-3-fluoro-6-methoxy-5-nitro-pyridine X-2b To a solution of 3-fluoro-6-methoxy-5-nitro-pyridin-2-ol X-2a (0.29 g, 1.54 mmol) in CH$_3$CN (4 mL) was added KOH (0.87 g, 15.4 mmol) solution in H$_2$O (1 mL) and bromodifluoromethyl diethylphosphonate (2.74 mL, 15.4 mmol) at 40° C. and the reaction mixture was stirred at same temperature for 4 h. Progress of reaction was monitored by TLC. After completion, the reaction mixture was diluted with H$_2$O (50 mL) and extracted with EtOAc (3×40 mL). The organic layer was separated, dried over anhydrous Na$_2$SO$_4$ and concentrated under vacuum. The crude obtained was purified by flash chromatography (2 to 5% EtOAc in hexane) to afford 2-(difluoromethoxy)-3-fluoro-6-methoxy-5-nitro-pyridine X-2b (0.24 g) as a pale yellow liquid.

This compound was used as such for the next reaction without further purification.

Yield: 65%.

$^1$H NMR (400 MHz, DMSO-d$_6$) δ 4.04 (s, 3H), 7.90 (t, J=70.8 Hz, 1H), 8.80 (d, J=9.60 Hz, 1H).

Step-3: Synthesis of 6-(difluoromethoxy)-5-fluoro-2-methoxy-pyridin-3-amine X-2

To a solution of 2-(difluoromethoxy)-3-fluoro-6-methoxy-5-nitro-pyridine X-2b (0.23 g, 0.97 mmol) in CH$_3$COOH (8 mL) was added Fe (0.27 g, 4.83 mmol) slowly at 0° C. and the reaction mixture was stirred at room temperature for 4 h. Progress of reaction was monitored by TLC and LCMS. After completion, the reaction mixture was filtered through a pad of celite, washed with EtOAc (80 mL) and filtrate was concentrated under vacuum. The residue was poured in to aqueous saturated NaHCO$_3$ (80 mL) solution and extracted with EtOAc (2×70 mL). The organic layer was separated, dried over anhydrous Na$_2$SO$_4$ and concentrated under vacuum to afford 6-(difluoromethoxy)-5-fluoro-2-methoxy-pyridin-3-amine X-2 (0.18 g) as a brown liquid.

This compound was used as such for the next reaction without further purification.

Yield: 77%.

Basic LCMS Method 1 (ES$^-$): 207 (M–H)$^-$, 85% purity.
$^1$H NMR (400 MHz, DMSO-d$_6$) b 3.84 (s, 3H), 5.18 (brs, 2H), 6.95 (d, J=10.8 Hz, 1H), 7.39 (t, J=74 Hz, 1H).

A.3. Synthesis of 5-chloro-3-fluoro-6-methoxy-pyridin-2-amine X-3

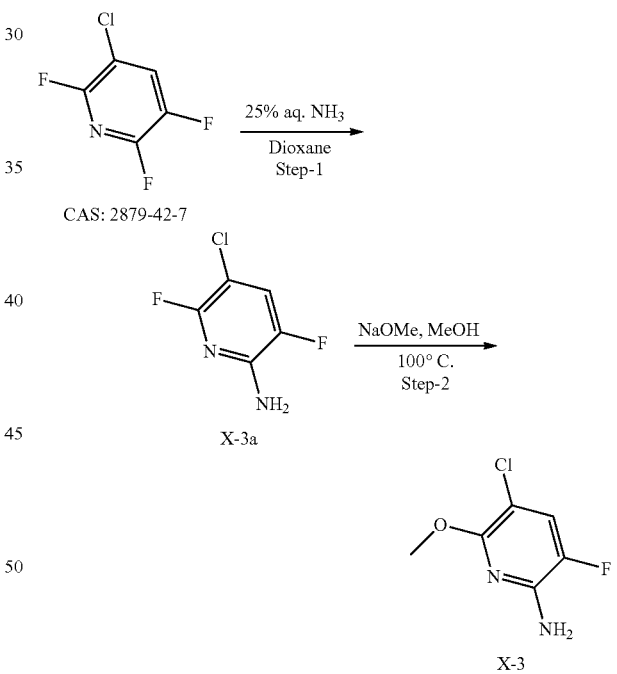

Step-1: Synthesis of 5-chloro-3,6-difluoro-pyridin-2-amine X-3a

To a solution of 3-chloro-2,5,6-trifluoro-pyridine (0.50 g, 2.98 mmol) in Dioxane (10 mL) was added 25% aqueous NH$_3$ (4 mL) and the reaction mixture was heated in steel bumb at 100° C. for 12 h. Progress of the reaction was monitored by TLC and LCMS. After completion, the reaction mixture was diluted with H$_2$O (200 mL) and extracted with EtOAc (400 mL). The organic layer was separated, dried over anhydrous Na$_2$SO$_4$ and concentrated under vacuum to afford 5-chloro-3,6-difluoro-pyridin-2-amine X-3a (0.41 g crude) as a yellow solid.

This compound was used as such for the next reaction without further purification.

¹H NMR (400 MHz, DMSO-d$_6$) δ 6.85 (s, 2H), 7.80-7.85 (m, 1H).

Step-2: Synthesis of
5-chloro-3-fluoro-6-methoxy-pyridin-2-amine X-3

To a solution of 5-chloro-3,6-difluoro-pyridin-2-amine X-14 (0.50 g, 2.97 mmol) in MeOH (25 mL) was added NaOMe (0.48 g, 8.92 mmol) and the reaction mixture was heated at 100° C. for 24 h. Progress of the reaction was monitored by TLC and LCMS. After completion, the reaction mixture was concentrated under vacuum. The residue was diluted with H$_2$O (100 mL) and extracted with DCM (200 mL). The organic layer was separated, dried over anhydrous Na$_2$SO$_4$ and concentrated under vacuum to afford 5-chloro-3-fluoro-6-methoxy-pyridin-2-amine X-3 (0.40 g) as an off-white solid.

This compound was used as such for the next reaction without further purification.

Yield: 72%

¹H NMR (400 MHz, DMSO-d$_6$) b 3.80 (s, 3H) 6.35 (s, 2H) 7.58 (d, J=9.78 Hz, 1H).

B. Synthesis of Intermediates of Formula XI

B.1. Synthesis of 6-chloro-1-methyl-1H-indole XI-1

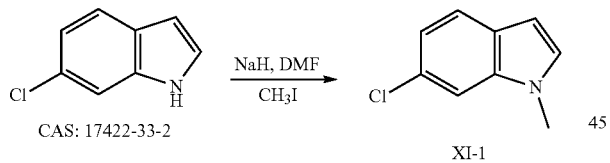

To a solution of 6-chloroindole (0.80 g, 5.29 mmol) in DMF (15 mL) was added NaH (0.25 g, 10.5 mmol) at 0° C. and the reaction mixture was stirred at same temperature for 30 min. Methyliodide (2.40 mL, 6.34 mmol) was added at 0° C. and the reaction mixture was stirred at same temperature for 2 h. Progress of the reaction was monitored by TLC and LCMS. After completion, the reaction mixture was quenched with ice cold H$_2$O (15 mL) and extracted with EtOAc (2×30 mL). The organic layer was separated, washed with brine (20 mL), dried over anhydrous Na$_2$SO$_4$ and concentrated in vacuo. The crude obtained was purified by column chromatography (silica, 100-200 mesh, 30% EtOAc in hexanes) to afford 6-chloro-1-methyl-1H-indole XI-1 (0.60 g) as a white solid.

Yield: 68%.

¹H NMR (400 MHz, CDCl$_3$) δ 3.78 (s, 3H) 6.48 (d, J=2.93 Hz, 1H) 7.06 (d, J=3.42 Hz, 1H) 7.09 (d, J=8.56 Hz, 1H) 7.34 (s, 1H) 7.54 (d, J=8.31 Hz, 1H).

B.2. Synthesis of 6-chloro-1-(2,2-difluoroethyl)pyrrolo[2,3-b]pyridine XI-2

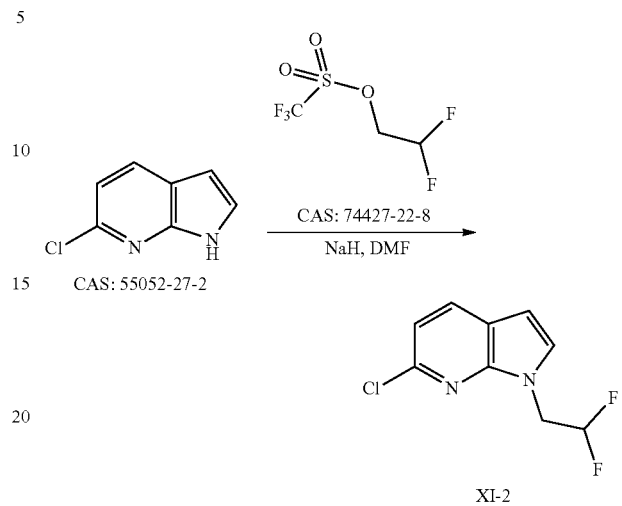

A solution of 6-chloro-7-azaindole (300 mg, 1.97 mmol) in 10 mL of DMF was treated with sodium hydride (66% in paraffin, 500 mg, 13.8 mmol) and stirred for 1 h at room temperature. Subsequently, 2,2-difluoroethyl trifluoromethanesulfonate (0.4 mL, 3.0 mmol) was added at room temperature. After stirring for 16 h, water (100 mL) was added and the resulting precipitate was filtered under reduced pressure, washed with water and dried at 50° C. Subsequently the crude product was purified by column chromatography on silica gel 60 (eluent: pure dichloromethane) leading to 6-chloro-1-(2,2-difluoroethyl)pyrrolo[2,3-b]pyridine XI-2 as colorless crystals.

Yield: 91%.

¹H NMR (600 MHz, CDCl$_3$) δ 7.84 (d, J=8.1 Hz, 1H), 7.21 (d, J=3.6 Hz, 1H), 7.09 (d, J=8.2 Hz, 1H), 6.49 (d, J=3.6 Hz, 1H), 6.07 (tt, 2JH,F=55.5, J=4.2 Hz, 1H), 4.59 (td, 3JH,F=14.0, J=4.3 Hz, 2H).

B.3. Synthesis of methyl 3-(6-chloro-1H-indol-1-yl)-2-fluoropropanoate XI-3

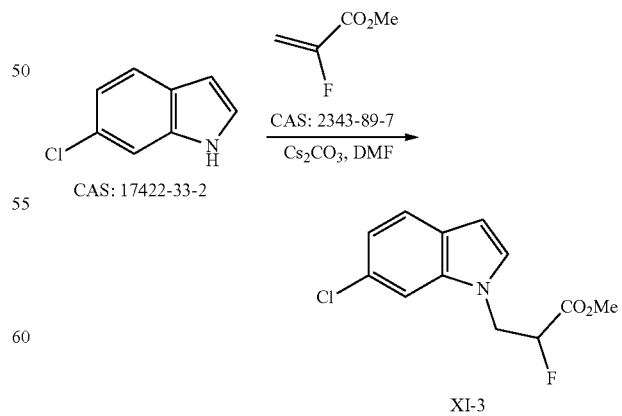

To a solution of 6-chloroindole (1.06 g, 6.99 mmol) and Cs$_2$CO$_3$ (2.73 g, 8.39 mmol) in DMF (10 mL), was added methyl 2-fluoroacrylate (0.8 g, 7.69 mmol) dropwise. Subsequently, the mixture was stirred at room temperature overnight. The reaction was quenched with H₂O (50 mL) and extracted with Et₂O (50 mL). The organic phase was washed with brine and dried over MgSO₄. After removal of the solvent under reduced pressure, the residue was purified by column chromatography on silica gel yielding methyl 3-(6-chloro-1H-indol-1-yl)-2-fluoropropanoate XI-3 (910 mg).

Yield: 51%.

¹H NMR (600 MHz, CDCl₃) δ 7.52 (d, J=8.4 Hz, 1H), 7.37-7.31 (m, 1H), 7.12-7.07 (m, 2H), 6.51 (dd, J=3.2, 0.9 Hz, 1H), 5.20 (ddd, J=48.3, 6.3, 3.0 Hz, 1H), 4.66-4.47 (m, 2H), 3.76 (s, 3H).

B.4. Synthesis of methyl 3-(6-chloro-1H-pyrrolo[2,3-b]pyridin-1-yl)-2-fluoropropanoate XI-4

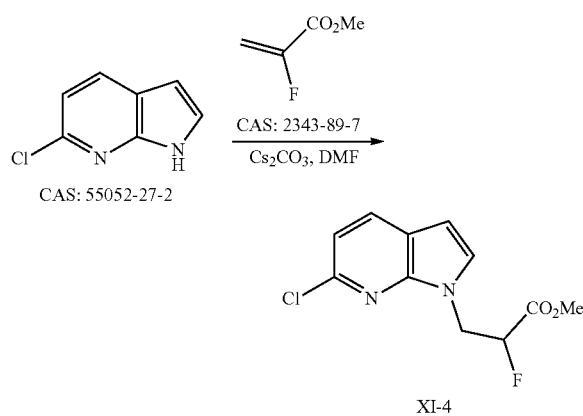

To a solution of 6-chloro-1H-pyrrolo[2,3-b]pyridine (1.07 g, 6.99 mmol) and Cs₂CO₃ (2.73 g, 8.39 mmol) in DMF (10 mL) was added methyl 2-fluoroacrylate (0.8 g, 7.69 mmol) dropwise. The mixture was stirred at room temperature overnight, quenched with H₂O (50 mL) and extracted with Et₂O (50 mL). The organic phase was washed with brine, dried over MgSO₄, filtered and concentrated. The residue was purified by column chromatography on silica gel yielding methyl 3-(6-chloro-1H-pyrrolo[2,3-b]pyridin-1-yl)-2-fluoropropanoate XI-4 (1.36 g).

Yield: 76%.

¹H NMR (600 MHz, CDCl₃) δ 7.84 (d, J=8.1 Hz, 1H), 7.24 (dd, J=3.6, 1.4 Hz, 1H), 7.09 (d, J=8.1 Hz, 1H), 6.49 (d, J=3.6 Hz, 1H), 5.28 (ddd, J=48.4, 6.6, 3.4 Hz, 1H), 4.91-4.54 (m, 2H), 3.78 (s, 3H).

C. Synthesis of Intermediates of Formula XII

C.1. Synthesis of 6-chloro-1-methyl-1H-indole-3-sulfonyl chloride XII-1

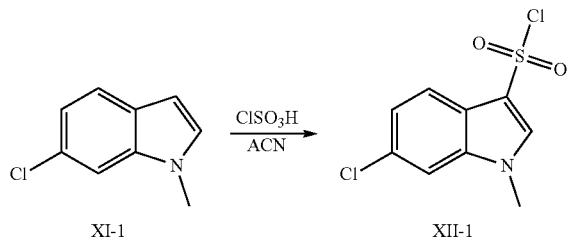

To a solution of 6-chloro-1-methyl-1H-indole XI-1 (0.50 g, 2.85 mmol) in CH₃CN (5 mL) was added ClSO₃H (1 mL) dropwise at 0° C. and the reaction mixture was stirred at room temperature for 2 h. Progress of reaction was monitored by TLC and LCMS. After completion, the reaction mixture was poured in to crushed ice H₂O (60 mL) and extracted with EtOAc (2×40 mL). The organic layer was separated, dried over anhydrous Na₂SO₄ and concentrated in vacuo to afford 6-chloro-1-methyl-1H-indole-3-sulfonyl chloride XII-1 (0.705 g) as a brown solid.

This compound was used as such for next reaction without further purification.

Yield: 78%

Basic LCMS Method 1 (ES⁻): 244 (M−H)⁻ corresponding sulphonic acid, 83% purity.

¹H NMR (400 MHz, DMSO-d₆) δ 7.72 (d, J=8.80 Hz, 1H) 7.52 (d, J=1.96 Hz, 1H) 7.43 (m, 1H) 7.05-7.09 (m, 1H) 3.73 (s, 3H)

C.2. Synthesis of 6-chloro-1-methyl-pyrrolo[2,3-b]pyridine-3-sulfonyl chloride XII-2

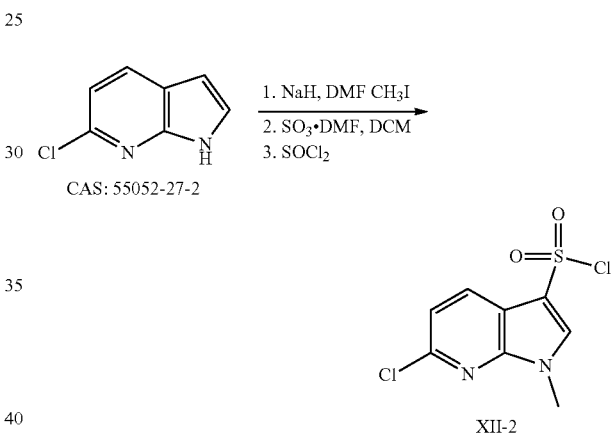

A solution of 6-chloro-7-azaindole (300 mg, 1.97 mmol) in 10 mL of DMF was treated with sodium hydride (66% in paraffin, 500 mg, 13.8 mmol) and stirred for 1 h at room temperature. Subsequently methyl iodide (0.2 mL, 3.2 mmol) was added at room temperature. After stirring for 16 h, water (100 mL) was added and the suspension was extracted with ethyl acetate (3×30 mL). The combined organic extracts were dried over MgSO₄, filtered and concentrated under reduced pressure. The resulting material was only characterized by TLC and directly used for the next step. The crude material (ca. 1.9 mmol) was dissolved in dichloromethane (15 mL) and treated with sulfur trioxide/DMF complex (500 mg, 3.27 mmol). The mixture was stirred at room temperature for 0.5 h. Subsequently thionyl chloride (0.6 mL, 8.34 mmol) was added and the formed suspension was stirred at room temperature for 14 d. The resulting clear solution was controlled by TLC. The mixture was hydrolysed with a saturated aqueous solution of NaHCO₃ (75 mL) and extracted with dichloromethane (3×30 mL). The combined organic extracts were dried over MgSO₄, filtered and concentrated under reduced pressure. The residue was crystallized from dichloromethane/petroleum ether leading to 320 mg of 6-chloro-1-methyl-pyrrolo[2,3-b]pyridine-3-sulfonyl chloride XII-2 as colorless crystals.

C.3. Synthesis of 6-chloro-1-(2,2-difluoroethyl)-1H-pyrrolo[2,3-b]pyridine-3-sulfonyl chloride XII-3

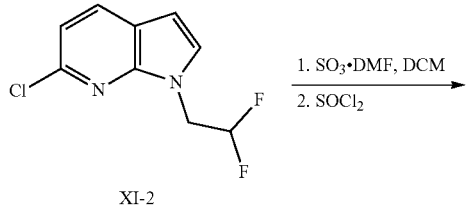

A solution of 6-chloro-1-(2,2-difluoroethyl)pyrrolo[2,3-b]pyridine XI-2 (367 mg, 1.7 mmol) in dichloromethane was treated with sulfur trioxide/DMF complex (500 mg, 3.27 mmol). The mixture was stirred at room temperature for 0.5 h (TLC control showed no further starting material but a complete conversion to the expected sulfonic acid, eluent: pure dichloromethane). Subsequently thionyl chloride (0.6 mL, 8.34 mmol) was added and mixture was stirred at room temperature for 16 h. The reaction was controlled by TLC (one spot for the expected product was observed, eluent: pure dichloromethane). The mixture was hydrolysed with a saturated aqueous solution of NaHCO$_3$ (75 mL) and extracted with dichloromethane (3×30 mL). The combined organic extracts were dried over MgSO$_4$, filtered and concentrated under reduced pressure. The residue was crystallized from petroleum ether leading to 325 mg of 6-chloro-1-(2,2-difluoroethyl)-1H-pyrrolo[2,3-b]pyridine-3-sulfonyl chloride XII-3 as colorless crystals.

Yield: 67%

$^1$H NMR (600 MHz, CDCl$_3$) δ 8.29 (d, J=8.4 Hz, 1H), 8.03 (s, 1H), 7.42 (d, J=8.3 Hz, 1H), 6.17 (tt, J=54.9 Hz, J=3.9 Hz, 1H), 4.71 (td, J=14.0 Hz, J=3.9 Hz, 2H).

C.4. Synthesis of methyl 3-(6-chloro-3-(chlorosulfonyl)-1H-indol-1-yl)-2-fluoropropanoate XII-4

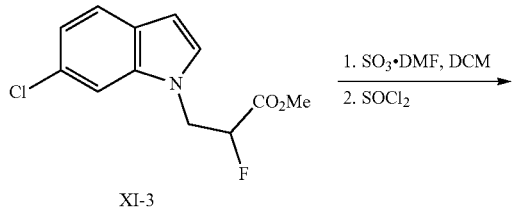

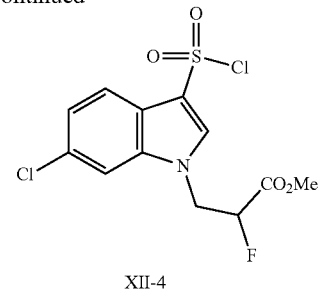

To a solution of methyl 3-(6-chloro-1H-indol-1-yl)-2-fluoropropanoate XI-3 (330 mg, 1.29 mmol) in CH$_2$Cl$_2$ (10 mL) was added SO$_3$.DMF (593 mg, 3.87 mmol). After stirring at room temperature for 48 h, SOCl$_2$ (0.56 mL, 7.7 mmol) was added and the mixture was stirred for another 24 h. Subsequently, the mixture was quenched with H$_2$O (20 mL) and extracted with EtOAc (50 mL). The organic phase was washed with brine, dried over MgSO$_4$ and concentrated under reduced pressure yielding methyl 3-(6-chloro-3-(chlorosulfonyl)-1H-indol-1-yl)-2-fluoropropanoate XII-4 (288 mg) which was directly used for the next step without further purification or characterization.

Yield: 63%

C.5. Synthesis of methyl 3-(6-chloro-3-(chlorosulfonyl)-1H-pyrrolo[2,3-b]pyridin-1-yl)-2-fluoropropanoate XII-5

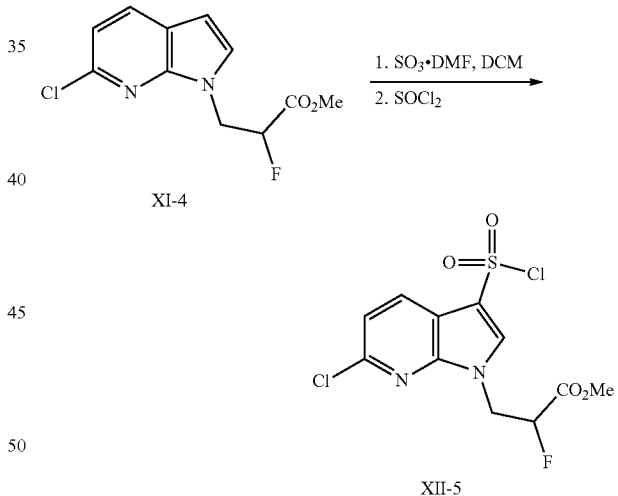

To a solution of methyl 3-(6-chloro-1H-pyrrolo[2,3-b]pyridin-1-yl)-2-fluoropropanoate XI-4 (300 mg, 1.17 mmol) in CH$_2$Cl$_2$ (10 mL) was added SO$_3$.DMF (537 mg, 3.51 mmol). After stirring at room temperature for 48 h, SOCl$_2$ (0.5 mL, 7.02 mmol) was added and the mixture was stirred for another 24 h. Subsequently, the mixture was quenched with H$_2$O (20 mL) and extracted with EtOAc (50 mL). The organic phase was washed with brine, dried over MgSO$_4$, filtered and concentrated under reduced pressure yielding methyl 3-(6-chloro-3-(chlorosulfonyl)-1H-pyrrolo[2,3-b]pyridin-1-yl)-2-fluoropropanoate XII-5 (215 mg) which was directly used for the next step without further purification or characterization.

Yield: 52%

C.6. Synthesis of 1-(benzenesulfonyl)-6-chloro-indole-3-sulfonyl chloride XII-6

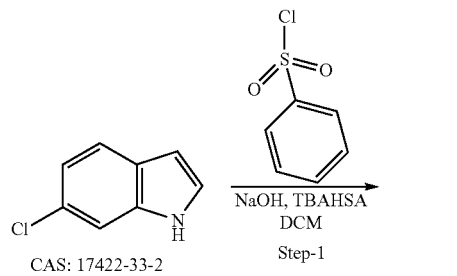

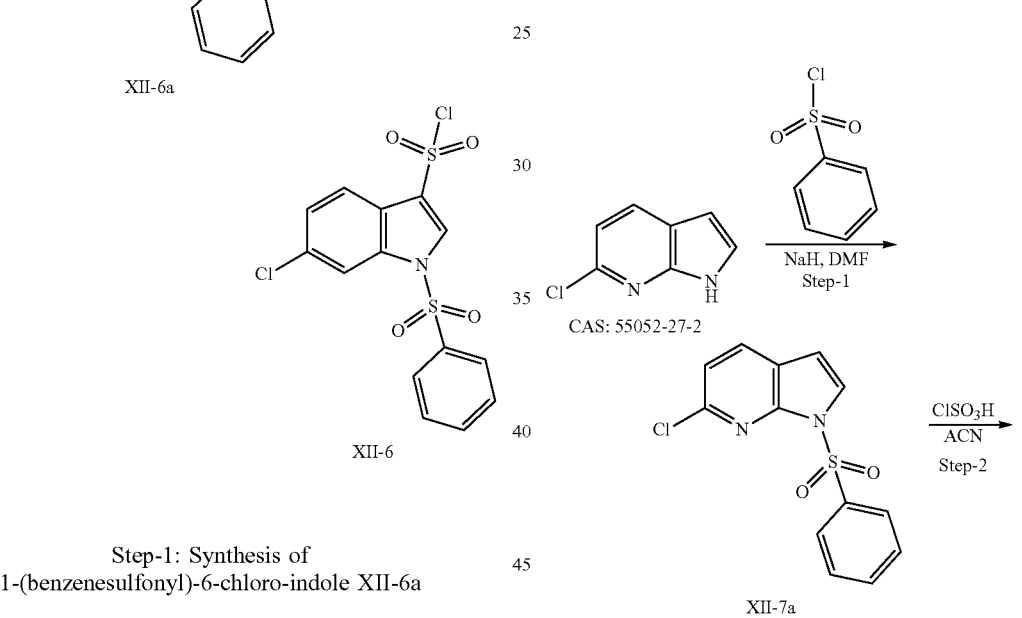

Step-1: Synthesis of 1-(benzenesulfonyl)-6-chloro-indole XII-6a

A suspension of finely powdered sodium hydroxide (24.5 g, 613 mmol) in dichloromethane (300 mL) was stirred in an ice bath and 6-chloroindole (30 g, 197 mmol) was added in one portion followed by tetrabutylammonium hydrogen sulfate (1.75 g, 5.15 mmol). Then benzenesulfonyl chloride (2.2 mL, 218 mmol) was added dropwise over 20 min and the reaction mixture was stirred at 0° C. for 1 h. The ice bath was then removed and the mixture was stirred for a further 1 h at room temperature. When LCMS showed completion of reaction, the reaction mixture was filtered through a celite pad and the latter was washed with DCM, combined filtrate and washings were evaporated to dryness. The product was triturated in ether, filtered, washed with small amount of ether then hexane and dried, the filtrate was concentrated to give a second crop with a total of 50.54 g of 1-(benzenesulfonyl)-6-chloro-indole XII-6a as a light brown solid.

Yield: 88%.

$^1$H NMR (400 MHz, CDCl$_3$) δ 8.04 (dd, J=1.8, 0.9 Hz, 1H), 7.91 (t, J=1.4 Hz, 1H), 7.89 (t, J=1.8 Hz, 1H), 7.67-7.54 (m, 2H), 7.53-7.48 (m, 2H), 7.48-7.42 (m, 1H), 7.23 (dd, J=8.4, 1.9 Hz, 1H), 6.65 (dd, J=3.7, 0.9 Hz, 1H).

Step-2: Synthesis of 1-(benzenesulfonyl)-6-chloro-indole-3-sulfonyl chloride XII-6

A solution of 1-(benzenesulfonyl)-6-chloro-indole XII-6a (50 g, 171.4 mmol) in acetonitrile (500 mL) was stirred in an ice bath and chlorosulfonic acid (100.8 g, 856.8 mmol) was added dropwise over 20 min and the reaction mixture was stirred for 5 days at room temperature. It was then slowly poured with stirring into ice-water (2.2 L) for 20 min, filtered, washed several times with water and dried by suction to give 63.77 g of 1-(benzenesulfonyl)-6-chloro-indole-3-sulfonyl chloride XII-6 as a light brown solid.

Yield: 95%.

$^1$H NMR (400 MHz, CDCl$_3$) δ 8.36 (s, 1H), 8.07 (d, J=1.8 Hz, 1H), 8.04 (t, J=1.3 Hz, 1H), 8.02 (d, J=1.5 Hz, 1H), 7.91 (d, J=8.6 Hz, 1H), 7.79-7.70 (m, 1H), 7.68-7.59 (m, 2H), 7.47 (dd, J=8.6, 1.8 Hz, 1H).

C.7. Synthesis of 1-(benzenesulfonyl)-6-chloro-pyrrolo[2,3-b]pyridine-3-sulfonyl chloride XII-7

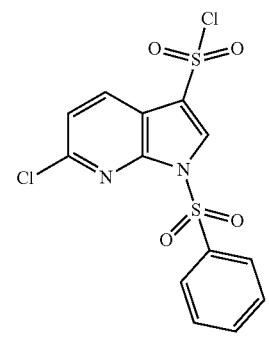

Step-1: Synthesis of 1-(benzenesulfonyl)-6-chloro-pyrrolo[2,3-b]pyridine XII-7a To a solution of 6-chloro-1H-pyrrolo[2,3-b]pyridine (1.37 g, 8.97 mmol) in DMF (100 mL), sodium hydride (60% in paraffin, 1 g, 41 mmol) was added. The solution was stirred for 30 min being allowed to warm up from 0° C. to rt. Subsequently, benzenesulfonic acid chloride (1.5 mL, 11.8 mmol) was added dropwise. The suspension was stirred 3 h at room temperature and hydrolyzed with ice water. The resulting solid was filtered off under reduced pressure, washed thoroughly with water (75 mL) and finally with petroleum ether (15 mL). The resulting material was dried at 60° C. and purified by column chromatography (eluent: pure dichloromethane) yielding 856 mg of 1-(benzenesulfonyl)-6-chloro-pyrrolo[2,3-b]pyridine XII-7a as a brownish solid.

Yield: 32%

Step-2: Synthesis of 1-(benzenesulfonyl)-6-chloro-pyrrolo[2,3-b]pyridine-3-sulfonyl chloride XII-7

The obtained 1-(benzenesulfonyl)-6-chloro-pyrrolo[2,3-b]pyridine XII-7a (150 mg, 0.51 mmol) was dissolved in acetonitrile (5 mL) and treated with chlorosulfonic acid (2 mL, 2.91 mmol) dropwise. The mixture was refluxed for 3 h, cooled to room temperature, hydrolyzed with ice water (50 mL) and neutralized with a saturated solution of sodium hydrogen carbonate. The crude product was extracted with dichloromethane (3 times, 50 mL each). The combined organic extracts were dried over MgSO₄, filtered and concentrated. The resulting material was purified by column chromatography (eluent: pure dichloromethane) yielding 163 mg of 1-(benzenesulfonyl)-6-chloro-pyrrolo[2,3-b]pyridine-3-sulfonyl chloride XII-7 as a yellowish solid.

Yield: 81%

$^1$H NMR (600 MHz, CDCl₃) δ: 8.48 (s, 1H), 8.32 (d, J=7.8 Hz, 2H), 8.18 (d, J=8.3 Hz, 1H), 7.71 (t, J=7.5 Hz, 1H), 7.60 (t, J=7.9 Hz, 2H), 7.41 (d, J=8.4 Hz, 1H).

D. Synthesis of Intermediates of Formula XIII

D.1. Synthesis of N-(4-bromo-2,5-difluoro-phenyl)-6-chloro-N-(methoxymethyl)-1H-indole-3-sulfonamide XIII-1

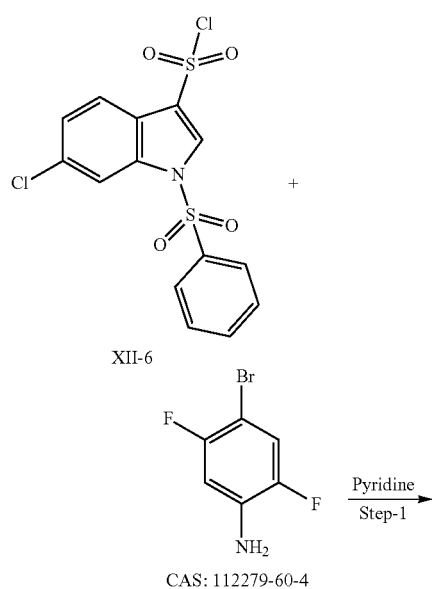

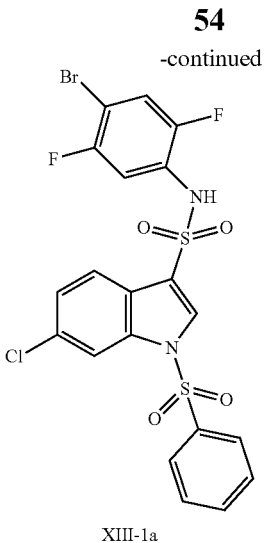

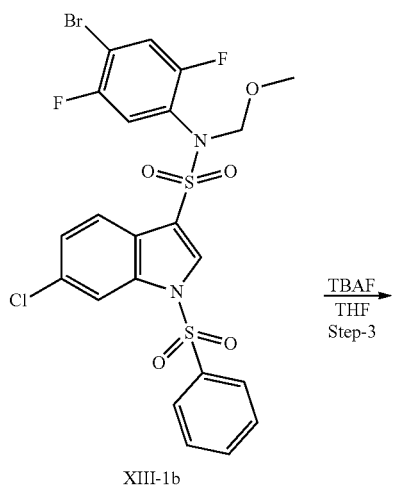

Step-1: Synthesis of N-(4-bromo-2,5-difluorophenyl)-6-chloro-1-(phenylsulfonyl)-1H-indole-3-sulfonamide XIII-1a A mixture of 1-(benzenesulfonyl)-6-chloro-indole-3-sulfonyl chloride XII-6 (1.56 g, 4 mmol) and 4-bromo-2,5-difluoroaniline (998 mg, 4.8 mmol) in pyridine (8 mL) was stirred at room temperature for 2 h. Subsequently, the reaction was quenched by the addition of 1M HCl (30 mL)

and extracted with ethyl acetate (3×50 mL). The combined organic extracts were washed with brine, dried over magnesium sulfate and evaporated to dryness. The residue was purified by column chromatography using petroleum ether:ethyl acetate (85:15) as a solvent to afford 2.2 g of N-(4-bromo-2,5-difluorophenyl)-6-chloro-1-(phenylsulfonyl)-1H-indole-3-sulfonamide XIII-1a as an off-white solid.

Yield: 80%.

$^1$H NMR (600 MHz, DMSO-d$_6$) δ 10.87 (s, 1H), 8.51 (s, 1H), 8.15-8.09 (m, 2H), 7.99 (d, J=1.8 Hz, 1H), 7.84 (d, J=8.5 Hz, 1H), 7.77 (t, J=7.5 Hz, 1H), 7.63-7.59 (m, 2H), 7.56 (dd, J=9.6, 6.3 Hz, 1H), 7.50 (dd, J=8.6, 1.8 Hz, 1H), 7.34 (dd, J=9.5, 6.8 Hz, 1H).

Step-2: Synthesis of N-(4-bromo-2,5-difluorophenyl)-6-chloro-N-(methoxymethyl)-1-(phenylsulfonyl)-1H-indole-3-sulfonamide XIII-1b N-(4-bromo-2,5-difluorophenyl)-6-chloro-1-(phenylsulfonyl)-1H-indole-3-sulfonamide XIII-1a (1.12 g, 2 mmol) and N,N-diisopropylethylamine (DIPEA) (0.4 mL, 2.4 mmol) were dissolved in dry dichloromethane (25 mL). The solution was stirred at rt for 30 min under argon atmosphere, then chloromethyl methyl ether (0.2 mL, 2.4 mmol) was added. After stirring for 16 h at room temperature, the mixture was concentrated under reduced pressure. The residue thus obtained was treated with 1M HCl (30 mL) and extracted with ethyl acetate (3×50 mL). The combined organic extracts were washed with brine, dried over magnesium sulfate and evaporated to dryness. The crude product was purified by column chromatography using petroleum ether:ethyl acetate (80:20) as an eluent to afford 1.2 g N-(4-bromo-2,5-difluorophenyl)-6-chloro-N-(methoxymethyl)-1-(phenylsulfonyl)-1H-indole-3-sulfonamide XIII-1b as a yellowish solid.

Yield: 80%.

$^1$H NMR (600 MHz, DMSO-d$_6$) δ 8.51 (s, 1H), 8.20 (dd, J=8.6, 1.3 Hz, 2H), 8.03 (d, J=1.8 Hz, 1H), 7.83-7.79 (m, 1H), 7.77 (dd, J=9.2, 6.3 Hz, 1H), 7.70-7.64 (m, 2H), 7.52 (d, J=8.6 Hz, 1H), 7.44 (dd, J=8.6, 1.8 Hz, 1H), 7.32 (dd, J=8.8, 6.4 Hz, 1H), 4.99 (s, 2H), 3.24 (s, 3H).

Step-3: Synthesis of N-(4-bromo-2,5-difluorophenyl)-6-chloro-N-(methoxymethyl)-1H-indole-3-sulfonamide XIII-1

N-(4-bromo-2,5-difluorophenyl)-6-chloro-N-(methoxymethyl)-1-(phenylsulfonyl)-1H-indole-3-sulfonamide XIII-1b (910 mg, 1.5 mmol) was dissolved in THF (25 mL), treated with tetra-n-butylammonium fluoride (TBAF, 1.0 M in THF, 7.5 mL, 7.5 mmol) and stirred for 2 h under reflux. The reaction mixture was then quenched with 1M HCl (10 mL) and extracted with ethyl acetate (2×50 mL). The combined organic extracts were dried over magnesium sulfate and evaporated to dryness. The residue was purified by column chromatography using petroleum ether:ethyl acetate (80:20) as a solvent affording 0.69 g of N-(4-bromo-2,5-difluorophenyl)-6-chloro-N-(methoxymethyl)-1H-indole-3-sulfonamide XIII-1 as a colorless solid.

Yield: 79%.

Neutral LCMS Method 2 (ES$^+$): 482/484 (M+18)+, 95% purity.

$^1$H NMR (600 MHz, DMSO-d$_6$) δ 12.28 (s, 1H), 7.99 (s, 1H), 7.81 (dd, J=9.2, 6.3 Hz, 1H), 7.56 (d, J=1.8 Hz, 1H), 7.46 (d, J=8.5 Hz, 1H), 7.24-7.17 (m, 2H), 4.95 (s, 2H), 3.26 (s, 3H).

D.2. Synthesis of N-(4-difluoromethoxy-2,5-difluoro-phenyl)-6-chloro-N-(methoxymethyl)-1H-indole-3-sulfonamide XIII-2

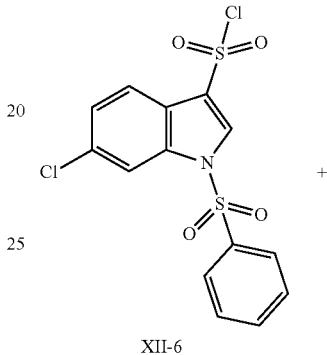

XII-6

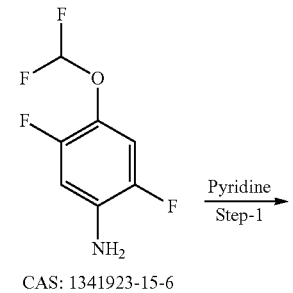

CAS: 1341923-15-6

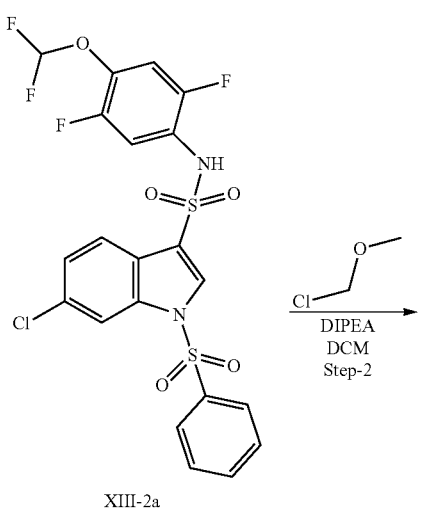

XIII-2a

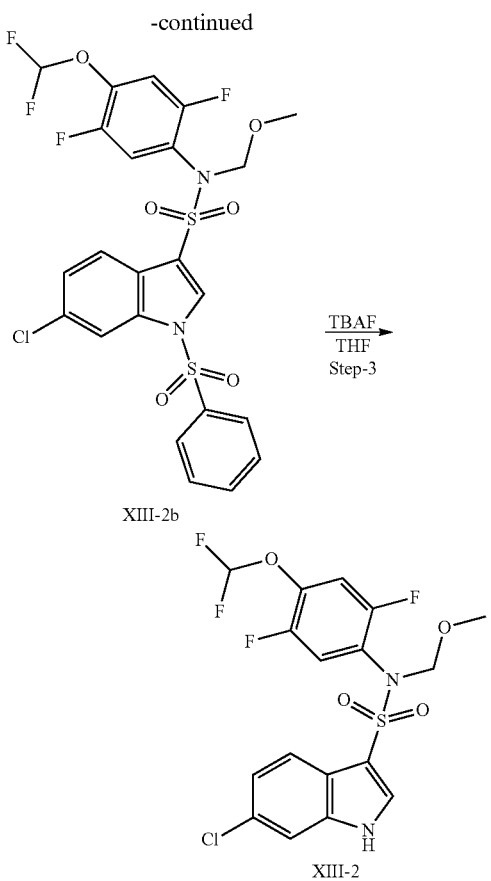

Step-1: Synthesis of 6-chloro-N-(4-(difluoromethoxy)-2,5-difluorophenyl)-1-(phenylsulfonyl)-1H-indole-3-sulfonamide XIII-2a A mixture of 1-(benzenesulfonyl)-6-chloro-indole-3-sulfonyl chloride XII-6 (1.17 g, 3 mmol) and 4-(difluoromethoxy)-2,5-difluoroaniline (703 mg, 3.6 mmol) in pyridine (8 mL) was stirred at room temperature for 2 h. The reaction was then quenched by addition of 30 mL of 1M HCl and extracted three times with ethyl acetate (3×50 mL). The combined organic extracts were washed with brine, dried over magnesium sulfate and evaporated to dryness. The residue was purified by column chromatography using petroleum ether:ethyl acetate (85:15) as a solvent to afford 1.5 g of 6-chloro-N-(4-(difluoromethoxy)-2,5-difluorophenyl)-1-(phenylsulfonyl)-1H-indole-3-sulfonamide XIII-2a as an off-white solid. The compound was directly used for the next step without further characterization.
Yield: 91%.

Step-2: Synthesis of 6-chloro-N-(4-(difluoromethoxy)-2,5-difluorophenyl)-N-(methoxymethyl)-1-(phenylsulfonyl)-1H-indole-3-sulfonamide XIII-2b 6-chloro-N-(4-(difluoromethoxy)-2,5-difluorophenyl)-1-(phenylsulfonyl)-1H-indole-3-sulfonamide XIII-2a (1.38 g, 2.5 mmol) and DIPEA (0.5 mL, 3 mmol) was suspended in 25 mL of dry dichloromethane under an Ar atmosphere. After stirring for 30 min at room temperature, chloromethyl methyl ether (0.25 mL, 3 mmol) was added. The mixture was stirred at room temperature for 16 h. Subsequently, all volatiles were removed under reduced pressure. The residue was treated with 1M HCl (30 mL) and extracted with ethyl acetate (3×50 mL). The combined organic extracts were washed with brine, dried over magnesium sulfate and evaporated to dryness. The crude product was purified by column chromatography using petroleum ether:ethyl acetate (80:20) as an eluent to afford 1.18 g of 6-chloro-N-(4-(difluoromethoxy)-2,5-difluorophenyl)-N-(methoxymethyl)-1-(phenylsulfonyl)-1H-indole-3-sulfonamide XIII-2b as an off-white solid.
Yield: 80%.
The compound was directly used for the next step without further characterization Step-3: Synthesis of N-(4-difluoromethoxy-2,5-difluoro-phenyl)-6-chloro-N-(methoxymethyl)-1H-indole-3-sulfonamide XIII-2

6-chloro-N-(4-(difluoromethoxy)-2,5-difluorophenyl)-N-(methoxymethyl)-1-(phenylsulfonyl)-1H-indole-3-sulfonamide XIII-2b (593 mg, 1 mmol) was dissolved in THF (25 mL), treated with TBAF (1.0 M) in THF (7.5 mL, 7.5 mmol) and stirred for 2 h under reflux. The reaction mixture was quenched with 1M HCl (10 mL) and extracted with ethyl acetate (2×50 mL). The combined organic extracts were dried over magnesium sulfate, filtered and evaporated to dryness. The crude material was purified by column chromatography using petroleum ether:ethyl acetate (80:20) as an eluent affording 0.34 g of N-(4-difluoromethoxy-2,5-difluoro-phenyl)-6-chloro-N-(methoxymethyl)-1H-indole-3-sulfonamide XIII-2 as a colorless solid.
Yield: 76%.
Neutral LCMS Method 2 (ES$^+$): 470 (M+18)+, 82% purity.
$^1$H NMR (600 MHz, DMSO-$d_6$) δ 12.27 (s, 1H), 7.99 (s, 1H), 7.57 (d, J=1.9 Hz, 1H), 7.47-7.40 (m, 2H), 7.25 (dd, J=10.7, 6.9 Hz, 1H), 7.18 (dd, J=8.7, 1.8 Hz, 1H), 4.95 (s, 2H), 3.27 (s, 3H). manque 1H D.3. Synthesis of 6-chloro-N-(6-chloro-5-fluoro-2-methoxypyridin-3-yl)-N-(methoxymethyl)-1H-indole-3-sulfonamide XIII-3

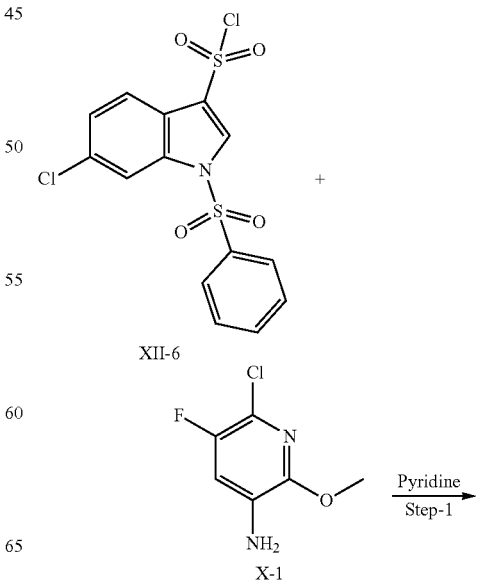

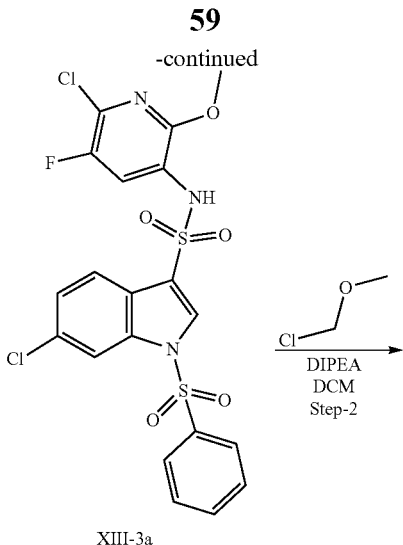

XIII-3a

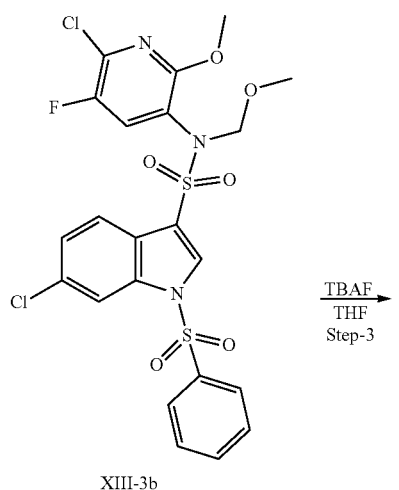

XIII-3b

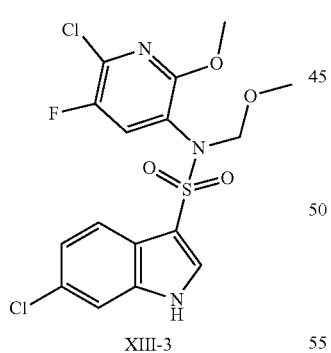

XIII-3

Step-1: Synthesis of 6-chloro-N-(6-chloro-5-fluoro-2-methoxypyridin-3-yl)-1-(phenylsulfonyl)-1H-indole-3-sulfonamide XIII-3a A mixture of 1-(benzenesulfonyl)-6-chloro-indole-3-sulfonyl chloride XII-6 (886 mg, 2.2 mmol) and 6-chloro-5-fluoro-2-methoxy-pyridin-3-amine X-1 (400 mg, 2.2 mmol) in pyridine (5 mL) was stirred at room temperature for 1.5 h. The mixture was quenched by the addition of 1M HCl (30 mL) and extracted with ethyl acetate (3×50 mL). The combined organic extracts were washed with brine, dried over magnesium sulfate and evaporated to dryness. The residue was purified by column chromatography using petroleum ether:ethyl acetate (80:20) as an eluent to afford 0.7 g of 6-chloro-N-(6-chloro-5-fluoro-2-methoxypyridin-3-yl)-1-(phenylsulfonyl)-1H-indole-3-sulfonamide XIII-3a as an off-white solid.

Yield: 60%.

The compound was directly used for the next step without further characterization.

Step-2: Synthesis of 6-chloro-N-(6-chloro-5-fluoro-2-methoxypyridin-3-yl)-N-(methoxymethyl)-1-(phenylsulfonyl)-1H-indole-3-sulfonamide XIII-3b 6-chloro-N-(6-chloro-5-fluoro-2-methoxypyridin-3-yl)-1-(phenylsulfonyl)-1H-indole-3-sulfonamide XIII-3a (700 mg, 1.3 mmol) and DIPEA (0.27 mL, 1.6 mmol) were dissolved in dry dichloromethane (25 mL). After stirring for 30 min at room temperature under Ar atmosphere, chloromethyl methyl ether (0.13 mL, 1.6 mmol, 1.2 equiv) was added. The mixture was stirred at room temperature for 16 h. Subsequently, volatile components were removed under reduced pressure. The residue was treated with 1M HCl (30 mL) and extracted with ethyl acetate (3×50 mL). The combined organic extracts were washed with brine, dried over magnesium sulfate and evaporated to dryness. The crude product was purified by column chromatography using petroleum ether:ethyl acetate (80:20) as an eluent to afford 0.59 g of 6-chloro-N-(6-chloro-5-fluoro-2-methoxypyridin-3-yl)-N-(methoxymethyl)-1-(phenylsulfonyl)-1H-indole-3-sulfonamide XIII-3b as an off-white solid.

Yield: 80%.

The compound was directly used for the next step without further characterization.

Step-3: Synthesis of 6-chloro-N-(6-chloro-5-fluoro-2-methoxypyridin-3-yl)-N-(methoxymethyl)-1H-indole-3-sulfonamide XIII-3

6-chloro-N-(6-chloro-5-fluoro-2-methoxypyridin-3-yl)-N-(methoxymethyl)-1-(phenylsulfonyl)-1H-indole-3-sulfonamide XIII-3b (574 mg, 1 mmol) was dissolved in THF (25 mL), treated with TBAF (1.0 M in THF, 7.5 mL, 7.5 mmol) and stirred for 2 h under reflux. The reaction mixture was then quenched with 1M HCl (10 mL) and extracted with ethyl acetate (2×50 mL). The combined organic extracts were dried over magnesium sulfate, filtered and evaporated to dryness. The crude product was purified by column chromatography using petroleum ether:ethyl acetate (80:20) to afford 0.33 g of 6-chloro-N-(6-chloro-5-fluoro-2-methoxypyridin-3-yl)-N-(methoxymethyl)-1H-indole-3-sulfonamide XIII-3 as a colorless solid.

Yield: 76%.

Neutral LCMS Method 2 (ES$^+$): 434 (M+H)$^+$, 94% purity.

$^1$H NMR (600 MHz, DMSO-$d_6$) δ 12.19 (s, 1H), 7.94 (s, 1H), 7.88 (d, J=8.1 Hz, 1H), 7.55 (d, J=1.9 Hz, 1H), 7.44 (d, J=8.6 Hz, 1H), 7.19 (dd, J=8.6, 1.9 Hz, 1H), 4.93 (s, 2H), 3.28 (s, 3H), 3.24 (s, 3H).

D.4. Synthesis of 6-chloro-N-(6-(difluoromethoxy)-5-fluoro-2-methoxypyridin-3-yl)-N-(methoxymethyl)-1H-pyrrolo[2,3-b]pyridine-3-sulfonamide XIII-4

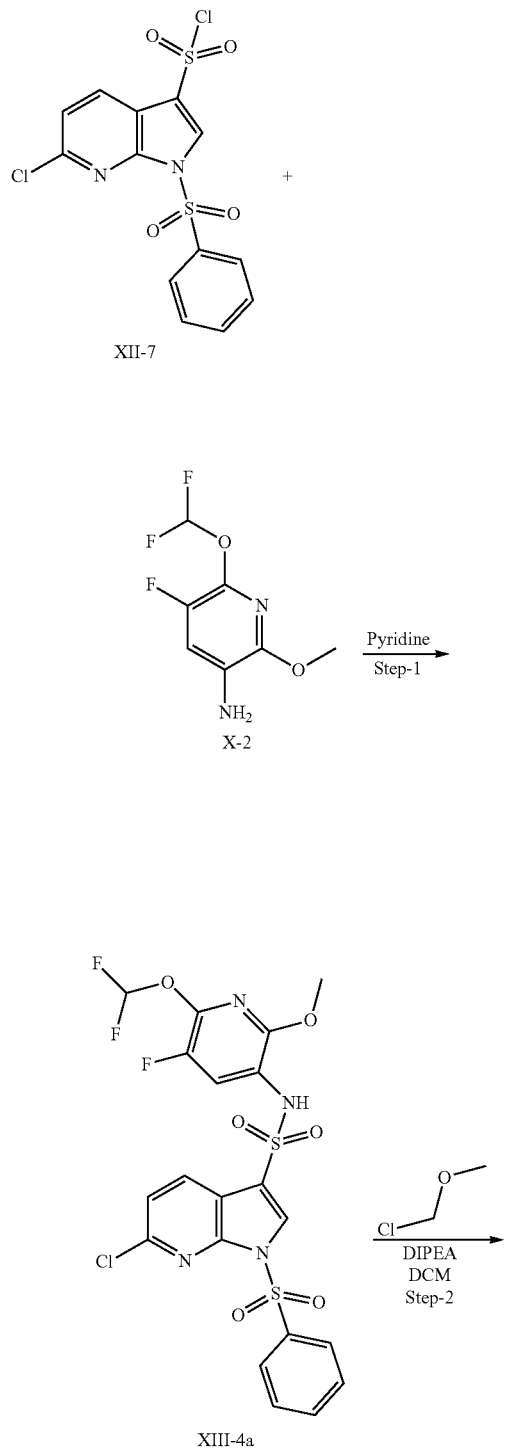

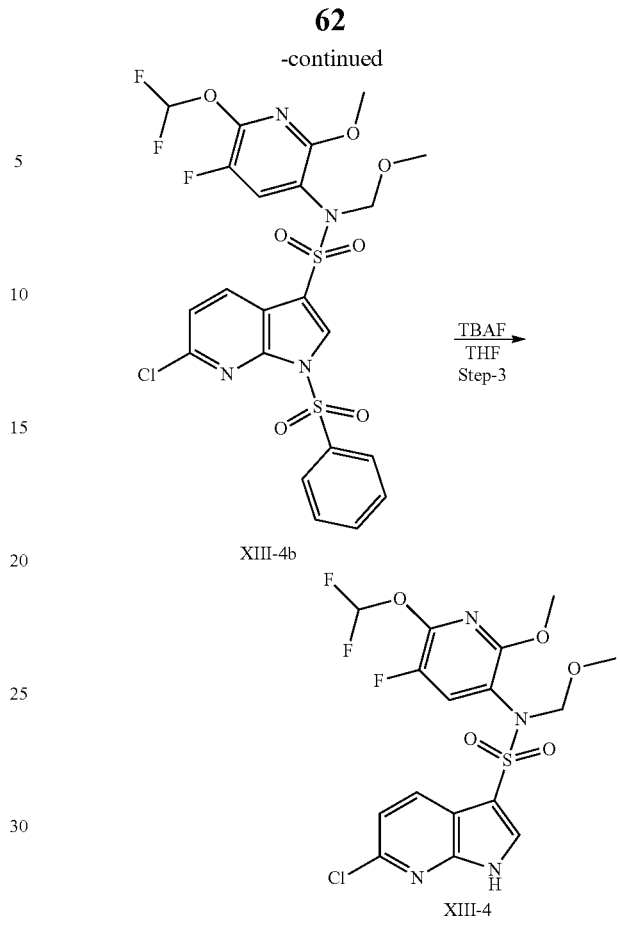

Step-1: Synthesis of 6-chloro-N-(6-(difluoromethoxy)-5-fluoro-2-methoxypyridin-3-yl)-1-(phenylsulfonyl)-1H-pyrrolo[2,3-b]pyridine-3-sulfonamide XIII-4a A mixture of 1-(benzenesulfonyl)-6-chloro-pyrrolo[2,3-b]pyridine-3-sulfonyl chloride XII-7 (438 mg, 1.1 mmol) and 6-(difluoromethoxy)-5-fluoro-2-methoxy-pyridin-3-amine X-2 (272 mg, 1.3 mmol) in pyridine (5 mL) was stirred at room temperature for 3 h. The reaction mixture was then quenched by the addition of 1M HCl (30 mL) and extracted 3 times with ethyl acetate (3×50 mL). The combined organic extracts were washed with brine, dried over magnesium sulfate, filtered and evaporated. The residue was purified by column chromatography using petroleum ether: ethyl acetate (85:15) as a solvent to afford 0.37 g of 6-chloro-N-(6-(difluoromethoxy)-5-fluoro-2-methoxypyridin-3-yl)-1-(phenylsulfonyl)-1H-pyrrolo[2,3-b]pyridine-3-sulfonamide XIII-4a as an off-white powder.

Yield: 61%.

Neutral LCMS Method 2 (ES+): 563 (M+H)+, 76% purity.

Step-2: Synthesis of 6-chloro-N-(6-(difluoromethoxy)-5-fluoro-2-methoxypyridin-3-yl)-N-(methoxymethyl)-1-(phenylsulfonyl)-1H-pyrrolo[2,3-b]pyridine-3-sulfonamide XIII-4b 6-chloro-N-(6-(difluoromethoxy)-5-fluoro-2-methoxypyridin-3-yl)-1-(phenylsulfonyl)-1H-pyrrolo[2,3-b]pyridine-3-sulfonamide XIII-4a (365 mg, 0.65 mmol) and DIPEA (0.13 mL, 0.78 mmol) were dissolved dry dichloromethane (25 mL) under Argon atmosphere. The solution was stirred at room temperature for 30 min, then chloromethyl methyl ether (0.06 mL, 0.78 mmol) was added. After stirring for 18 h at room temperature, volatile components were removed under reduced pressure. The residue was treated 1M HCl (30 mL) and extracted with ethyl acetate (3×50 mL). The combined organic extracts were washed with brine, dried over magnesium sulfate, filtered and evaporated. The residue was purified by column chromatography using petroleum ether:ethyl acetate (80:20) as an eluent to afford 0.30 g of 6-chloro-N-(6-(difluoromethoxy)-5-fluoro-2-methoxypyridin-3-yl)-N-(methoxymethyl)-1-(phenylsulfonyl)-1H-pyrrolo[2,3-b]pyridine-3-sulfonamide XIII-4b as a yellow powder.

Yield: 76%.

The compound was directly used for the next step without further characterization.

Step-3: Synthesis of 6-chloro-N-(6-(difluoromethoxy)-5-fluoro-2-methoxypyridin-3-yl)-N-(methoxymethyl)-1H-pyrrolo[2,3-b]pyridine-3-sulfonamide XIII-4

6-chloro-N-(6-(difluoromethoxy)-5-fluoro-2-methoxypyridin-3-yl)-N-(methoxymethyl)-1-(phenylsulfonyl)-1H-pyrrolo[2,3-b]pyridine-3-sulfonamide XIII-4b (273 mg, 0.45 mmol) was dissolved in THF (25 mL), treated with TBAF 1.0 M in THF (2.25 mL, 2.25 mmol) and stirred for 4 h under reflux. After adding 1M HCl (10 mL), the mixture was extracted with ethyl acetate (2×50 mL). The combined organic extracts were dried over magnesium sulfate, filtered and evaporated to dryness. The residue was purified by column chromatography using petroleum ether:ethyl acetate (80:20) as a solvent to afford 0.98 g of 6-chloro-N-(6-(difluoromethoxy)-5-fluoro-2-methoxypyridin-3-yl)-N-(methoxymethyl)-1H-pyrrolo[2,3-b]pyridine-3-sulfonamide XIII-4 as a white powder.

Yield: 47%.

D.5. Synthesis of N-(5-bromo-6-methoxypyridin-2-yl)-6-chloro-N-(methoxymethyl)-1H-indole-3-sulfonamide XIII-5

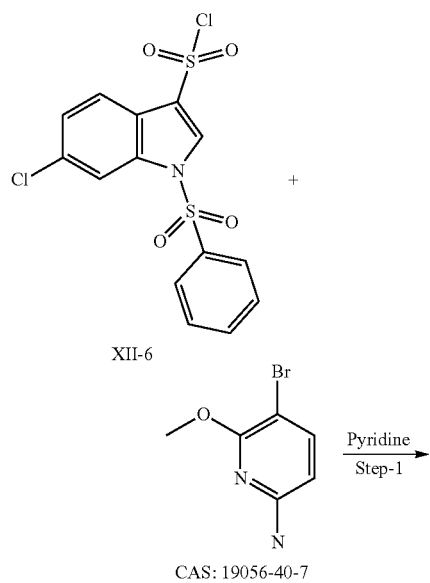

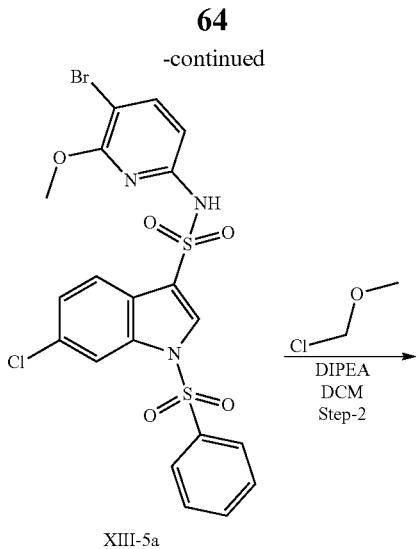

Step-1: Synthesis of N-(5-bromo-6-methoxypyridin-2-yl)-6-chloro-1-(phenylsulfonyl)-1H-indole-3-sulfonamide XIII-5a A mixture of 1-(benzenesulfonyl)-6-chloro-indole-3-sulfonyl chloride XII-6 (390 mg, 1 mmol) and 5-bromo-6-methoxypyridin-2-amine (244 mg, 1.2 mmol) in pyridine (5 mL) was stirred at room temperature for 1 h. Subsequently, the mixture was quenched with 1M HCl (30 mL) and extracted with ethyl acetate (3×50 mL). The combined organic extracts were washed with brine, dried over magnesium sulfate, filtered and evaporated to dryness. The residue was purified by column chromatography using petroleum ether:ethyl acetate (80:20) as a solvent to afford 0.39 g of N-(5-bromo-6-methoxypyridin-2-yl)-6-chloro-1-(phenylsulfonyl)-1H-indole-3-sulfonamide as XIII-5a an off-white solid.

Yield: 70%.

Neutral LCMS Method 2 (ES+): 556/558 (M+H)+, 91% purity.

Step-2: Synthesis of N-(5-bromo-6-methoxypyridin-2-yl)-6-chloro-N-(methoxymethyl)-1-(phenylsulfonyl)-1H-indole-3-sulfonamide XIII-5b N-(5-bromo-6-methoxypyridin-2-yl)-6-chloro-1-(phenylsulfonyl)-1H-indole-3-sulfonamide as XIII-5a (380 mg, 0.68 mmol) and DIPEA (0.1 mL, 0.8 mmol) were dissolved in 25 mL of dry dichloromethane under Ar atmosphere. The solution was stirred at room temperature for 30 min, then chloromethyl methyl ether (0.06 mL, 0.8 mmol, 1.2 equiv) was added. After stirring for additional 18 h at room temperature, volatile components were removed under reduced pressure. The residue thus obtained was treated with 1M HCl (30 mL) and extracted with ethyl acetate (3×50 mL). The combined organic extracts were washed with brine, dried over magnesium sulfate, filtered and evaporated. The residue was purified by column chromatography using petroleum ether:ethyl acetate (85:15) as an eluent affording 0.28 g of N-(5-bromo-6-methoxypyridin-2-yl)-6-chloro-N-(methoxymethyl)-1-(phenylsulfonyl)-1H-indole-3-sulfonamide XIII-5b as an off-white solid.

Yield: 69%.

Neutral LCMS Method 2 (ES+): 600/602 (M+H)+, 90% purity.

$^1$H NMR (600 MHz, DMSO-$d_6$) δ 8.63 (s, 1H), 8.17 (dd, J=8.5, 1.0 Hz, 2H), 8.04 (d, J=8.1 Hz, 1H), 8.00 (d, J=1.8 Hz, 1H), 7.78 (t, J=7.5 Hz, 1H), 7.67-7.61 (m, 2H), 7.44-7.35 (m, 2H), 7.05 (d, J=8.1 Hz, 1H), 5.28 (s, 2H), 3.27 (s, 3H), 3.14 (s, 3H).

Step-3: Synthesis of N-(5-bromo-6-methoxypyridin-2-yl)-6-chloro-N-(methoxymethyl)-1H-indole-3-sulfonamide XIII-5

N-(5-bromo-6-methoxypyridin-2-yl)-6-chloro-N-(methoxymethyl)-1-(phenylsulfonyl)-1H-indole-3-sulfonamide XIII-5b (280 mg, 0.46 mmol) was dissolved in THF (25 mL), treated with TBAF (1.0 M in THF, 2.3 mL, 2.3 mmol) and stirred for 2 h under reflux. The reaction mixture was then quenched with 10 mL of 1M HCl and extracted with ethyl acetate (2×50 mL). The combined organic extracts were dried over magnesium sulfate, filtered and evaporated. The residue was purified by column chromatography using petroleum ether:ethyl acetate (80:20) as a solvent to afford 0.16 g of N-(5-bromo-6-methoxypyridin-2-yl)-6-chloro-N-(methoxymethyl)-1H-indole-3-sulfonamide XIII-5 as a white solid.

Yield: 76%.

The compound was directly used in the next step without further characterization.

D.6. Synthesis of N-(4-bromo-2,5-difluorophenyl)-6-chloro-N-(methoxymethyl)-1H-pyrrolo[2,3-b]pyridine-3-sulfonamide XIII-6

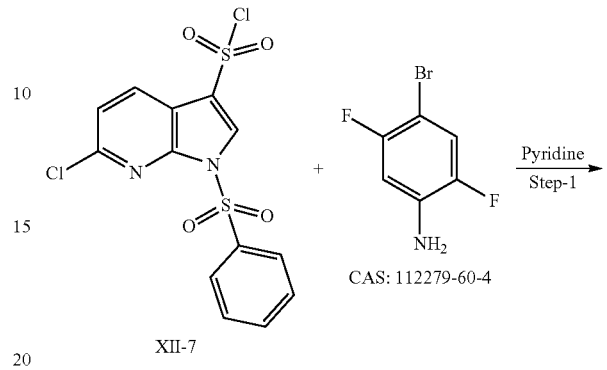

XII-7

CAS: 112279-60-4

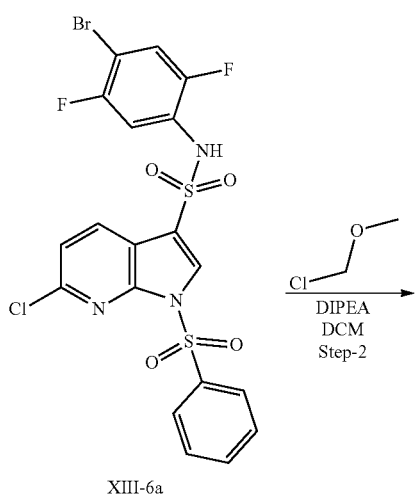

XIII-6a

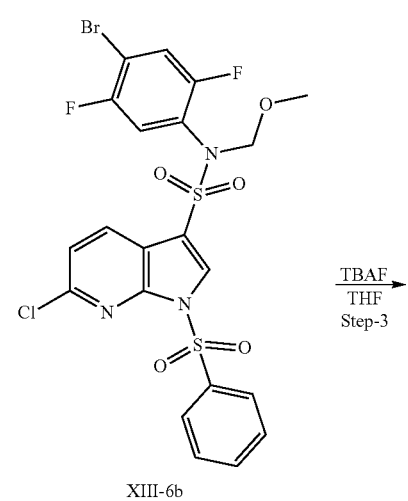

XIII-6b

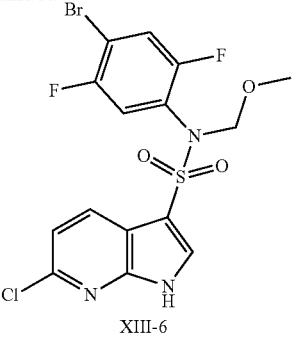

XIII-6

Step-1: Synthesis of N-(4-bromo-2,5-difluorophenyl)-6-chloro-1-(phenylsulfonyl)-1H-pyrrolo[2,3-b]pyridine-3-sulfonamide XIII-6a A mixture of 1-(benzenesulfonyl)-6-chloro-pyrrolo[2,3-b]pyridine-3-sulfonyl chloride XII-7 (390 mg, 1 mmol) and 4-bromo-2,5-difluoroaniline (248 mg, 1.2 mmol) in pyridine (5 mL) was stirred at room temperature for 2 h, subsequently quenched by the addition of 1M HCl (30 mL) and extracted with ethyl acetate (3×50 mL). The combined organic extracts were washed with brine, dried over magnesium sulfate, filtered and evaporated. The residue was purified by column chromatography using petroleum ether:ethyl acetate (85:15) as a solvent to afford 0.54 g of N-(4-bromo-2,5-difluorophenyl)-6-chloro-1-(phenylsulfonyl)-1H-pyrrolo[2,3-b]pyridine-3-sulfonamide XIII-6a as an off-white solid.

Yield: 80%.

Neutral LCMS Method 2 (ES$^+$): 562/564 (M+H)$^+$, 95% purity.

$^1$H NMR (600 MHz, DMSO-d$_6$) δ 10.84 (s, 1H), 8.42 (d, J=1.2 Hz, 1H), 8.20 (dd, J=8.4, 1.2 Hz, 1H), 8.15-8.09 (m, 2H), 7.80 (td, J=7.5, 1.2 Hz, 1H), 7.72-7.54 (m, 4H), 7.37 (dd, J=9.4, 6.8 Hz, 1H).

Step-2: Synthesis of N-(4-bromo-2,5-difluorophenyl)-6-chloro-N-(methoxymethyl)-1-(phenylsulfonyl)-1H-pyrrolo[2,3-b]pyridine-3-sulfonamide XIII-6b N-(4-bromo-2,5-difluorophenyl)-6-chloro-1-(phenylsulfonyl)-1H-pyrrolo[2,3-b]pyridine-3-sulfonamide XIII-6a (400 mg, 0.7 mmol) and DIPEA (0.14 mL, 0.84 mmol) were dissolved in 25 mL of dry dichloromethane under Argon atmosphere. The solution was stirred at room temperature for 30 min, then chloromethyl methyl ether (0.06 mL, 0.84 mmol) was added. After stirring for additional 18 h at room temperature, volatile components were removed under reduced pressure. The residue thus obtained was treated with 1M HCl (30 mL) and extracted with ethyl acetate (3×50 mL). The combined organic extracts were washed with brine, dried over magnesium sulfate, filtered and evaporated. The residue was purified by column chromatography using petroleum ether:ethyl acetate (85:15) as an eluent affording 0.27 g of N-(4-bromo-2,5-difluorophenyl)-6-chloro-N-(methoxymethyl)-1-(phenylsulfonyl)-1H-pyrrolo[2,3-b]pyridine-3-sulfonamide XIII-6b as an off-white solid.

Yield: 65%.

The compound was directly used for the next step without further characterization.

Step-3: Synthesis of N-(4-bromo-2,5-difluorophenyl)-6-chloro-N-(methoxymethyl)-1H-pyrrolo[2,3-b]pyridine-3-sulfonamide XIII-6

N-(4-bromo-2,5-difluorophenyl)-6-chloro-N-(methoxymethyl)-1-(phenylsulfonyl)-1H-pyrrolo[2,3-b]pyridine-3-sulfonamide XIII-6b (250 mg, 0.41 mmol) was dissolved in THF (25 mL), treated with TBAF 1.0 M in THF (2.05 mL, 2.05 mmol) and stirred for 2 h under reflux. The reaction mixture was then quenched with 10 mL of 1M HCl, extracted twice with ethyl acetate (100 mL), dried over magnesium sulfate and evaporated to dryness. The crude residue was purified by column chromatography using petroleum ether:ethyl acetate (80:20) to afford 0.12 g of N-(4-bromo-2,5-difluorophenyl)-6-chloro-N-(methoxymethyl)-1H-pyrrolo[2,3-b]pyridine-3-sulfonamide XIII-6 as a colorless solid.

Yield: 63%.

Neutral LCMS Method 2 (ES$^+$): 466/468 (M+H)$^+$, 94% purity.

The compound was used for the following alkylation step without further characterization.

EXAMPLE COMPOUNDS

E. Synthesis of Compounds of General Formula I

All compounds of the present invention specifically disclosed herein are designated "I-x" wherein any "x" refers to a number identifying the individual compounds. Accordingly, the Example compounds are designated I-1, I-2, I-3 etc. This is irrespective of whether any compound could also be described by any subgeneric Formula herein, e.g. by Formula II, III or IV, and the like.

E.1. Method A. Synthesis of 6-chloro-N-(4-cyano-2-fluorophenyl)-1-methylindole-3-sulfonamide I-1

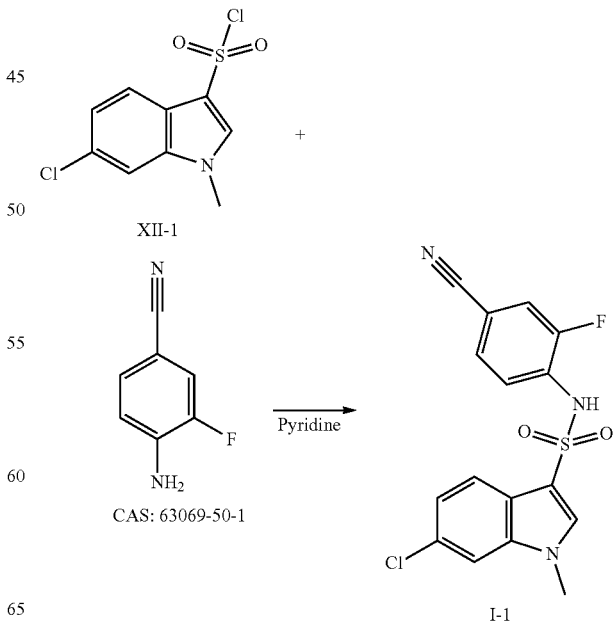

To a solution of 6-chloro-1-methyl-1H-indole-3-sulfonyl chloride XII-1 (0.40 g, 1.52 mmol) in pyridine (15 mL) was added 4-amino-3-fluoro-benzonitrile (0.23 g, 1.67 mmol) and the reaction mixture was heated at 80° C. for 3 h. Progress of the reaction was monitored by TLC and LCMS. After completion, the reaction mixture was concentrated in vacuo. The residue was diluted with $H_2O$ (15 mL) and extracted with EtOAc (2×30 mL). The organic layer was separated, washed with brine (10 mL), dried over anhydrous $Na_2SO_4$ and concentrated in vacuo. The crude obtained was purified by column chromatography (silica, 100-200 mesh, 3% EtOAc in hexane) to afford 6-chloro-N-(4-cyano-2-fluorophenyl)-1-methylindole-3-sulfonamide I-1 (0.05 g) as off-white solid.

Yield: 9%.

Basic LCMS Method 1 (ES$^-$): 362 (M−H)$^-$, 98% purity.

$^1$H NMR (400 MHz, DMSO-d$_6$) b 3.82 (s, 3H) 7.28 (d, J=7.34 Hz, 1H) 7.55-7.60 (m, 2H) 7.72-7.79 (m, 2H) 7.83 (d, J=8.31 Hz, 1H) 8.20 (s, 1H) 10.87 (s, 1H).

The following compounds in Table 1 may be synthesized according to a method analogous to Method A.

TABLE 1

| No | Sulfonyl chlorides XII | Amines X | Conditions, Time | Purification conditions | Yield (%) |
|---|---|---|---|---|---|
| 1-2 | XII-1 | X-3 | 80° C., 16 h | 30-40% EtOAc/Hexane | 53 |
| 1-3 | XII-2 | 112279-60-4 | 80° C., 16 h | DCM + crystallization in DCM/petroleum ether | 69 |
| 1-4 | XII-2 | 1341923-15-6 | 80° C., 16 h | DCM + crystallization in DCM/petroleum ether | 99 |
| 1-5 | XII-3 | 1341923-15-6 | 80° C., 16 h | DCM + crystallization in DCM/petroleum ether | 99 |
| 1-6 | XII-3 | 112279-60-4 | 80° C., 16 h | DCM + crystallization in DCM/petroleum ether | 39 |

6-chloro-N-(5-chloro-3-fluoro-6-methoxypyridin-2-yl)-1-methylindole-3-sulfonamide I-2

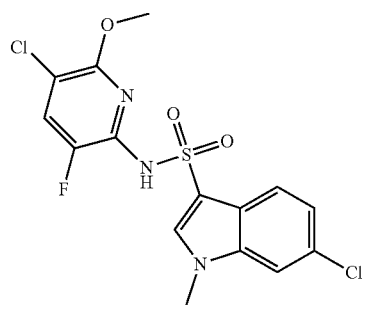 [SMILES: COc1nc(NS(=O)(=O)c2cn(C)c3cc(Cl)ccc23)c(F)cc1Cl]

Basic LCMS Method 1 (ES$^-$): 402 (M−H)$^-$, 100% purity.

$^1$H NMR (400 MHz, DMSO-d$_6$) b 3.65 (s, 3H) 3.85 (s, 3H) 7.25-7.28 (m, 1H) 7.73 (d, J=1.47 Hz, 1H) 7.83-7.87 (m, 1H) 7.92-7.95 (m, 1H) 8.23-8.24 (m, 1H) 11.15 (s, 1H).

N-(4-bromo-2,5-difluorophenyl)-6-chloro-1-methylpyrrolo[2,3-b]pyridine-3-sulfonamide I-3

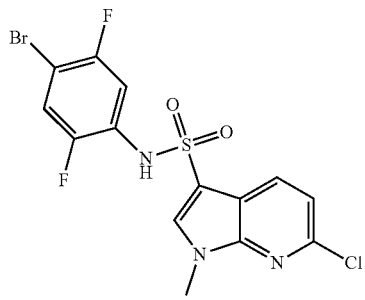 [SMILES: Cn1cc(S(=O)(=O)Nc2cc(F)c(Br)cc2F)c2ccc(Cl)nc21]

Neutral LCMS Method 2 (ES$^+$): 436 (M+H)$^+$, 95% purity.

$^1$H NMR (600 MHz, DMSO-d$_6$) δ 10.55 (s, 1H), 8.28 (s, 1H), 8.19 (d, J=8.3 Hz, 1H), 7.62 (dd, J=9.6, 6.3 Hz, 1H), 7.40 (d, J=8.3 Hz, 1H), 7.33 (dd, J=9.8, 6.8 Hz, 1H), 3.80 (s, 3H).

6-chloro-N-[4-(difluoromethoxy)-2,5-difluorophenyl]-1-methylpyrrolo[2,3-b]pyridine-3-sulfonamide I-4

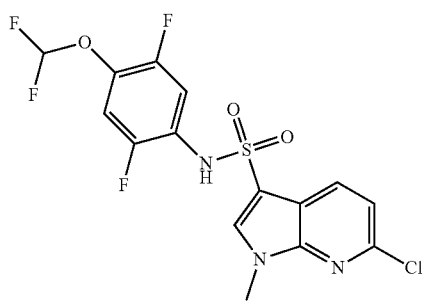 [SMILES: Cn1cc(S(=O)(=O)Nc2cc(F)c(OC(F)F)cc2F)c2ccc(Cl)nc21]

Neutral LCMS Method 2 (ES$^+$): 424 (M+H)$^+$, 98% purity.

$^1$H NMR (600 MHz, DMSO-d$_6$) δ 10.41 (s, 1H), 8.24 (s, 1H), 8.12 (d, J=8.3 Hz, 1H), 7.38 (d, J=8.1 Hz, 1H), 7.36-7.29 (m, 2H), 7.16 (t, J=72.7 Hz, 1H), 3.80 (s, 3H).

6-chloro-1-(2,2-difluoroethyl)-N-[4-(difluoromethoxy)-2,5-difluorophenyl]pyrrolo[2,3-b]pyridine-3-sulfonamide I-5

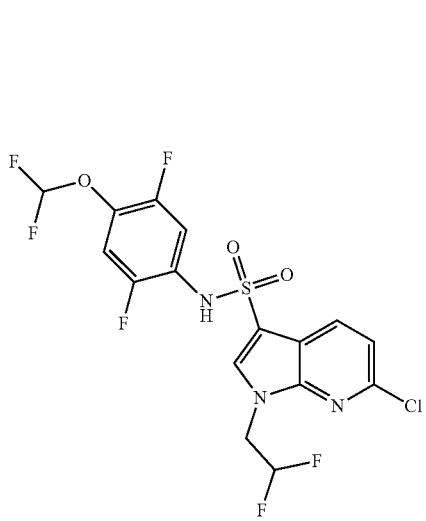 [SMILES: O=S(=O)(Nc1cc(F)c(OC(F)F)cc1F)c1cn(CC(F)F)c2nc(Cl)ccc12]

Neutral LCMS Method 2 (ES+): 474 (M+H)+, 96% purity.

$^1$H NMR (600 MHz, DMSO-d$_6$) δ 10.47 (s, 1H), 8.17 (s, 1H), 8.15 (d, J=8.3 Hz, 1H), 7.44 (d, J=8.3 Hz, 1H), 7.31-7.29 (m, 2H), 7.15 (t, J=72.8 Hz, 1H), 6.39 (tt, J=54.6 Hz, J=3.3 Hz, 1H), 4.74 (td, J=15.7 Hz, 3.3 Hz, 2H).

N-(4-bromo-2,5-difluorophenyl)-6-chloro-1-(2,2-difluoroethyl)pyrrolo[2,3-b]pyridine-3-sulfonamide I-6

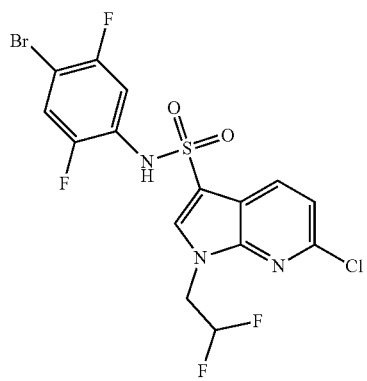 [SMILES: O=S(=O)(Nc1cc(F)c(Br)cc1F)c1cn(CC(F)F)c2nc(Cl)ccc12]

Neutral LCMS Method 2 (ES+): 486 (M+H)+, 98% purity.

$^1$H NMR (600 MHz, DMSO-d$_6$) δ 10.61 (s, 1H), 8.22 (d, J=8.2 Hz, 1H), 8.22 (s, 1H), 7.61 (dd, J=9.7, 6.4 Hz, 1H), 7.46 (d, J=8.3 Hz, 1H), 7.28 (dd, J=9.7, 6.7 Hz, 1H), 6.40 (t, J=54.5 Hz, 1H), 4.74 (t, J=15.3 Hz, 2H).

E.2. Synthesis of N-(4-bromo-2,5-difluorophenyl)-6-chloro-1-(2-fluoro-3-hydroxypropyl)indole-3-sulfonamide I-7

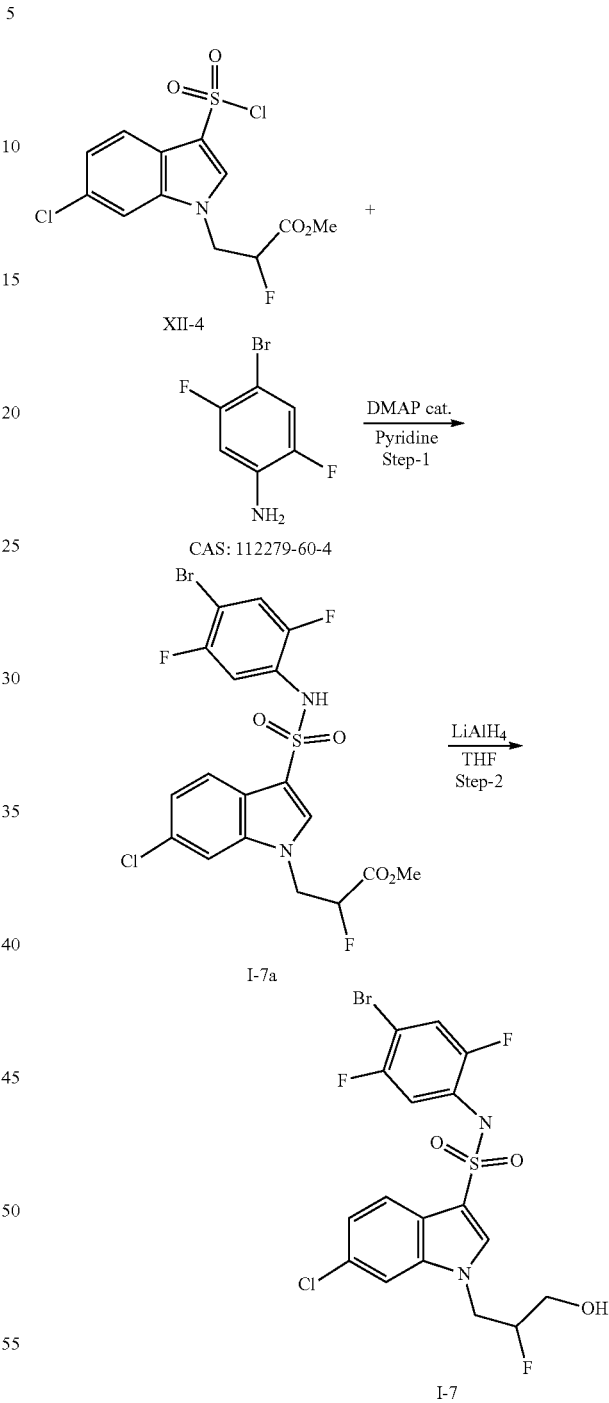

Step-1: Synthesis of methyl 3-[3-[(4-bromo-2,5-difluoro-phenyl)sulfamoyl]-6-chloro-indol-1-yl]-2-fluoro-propanoate I-7a A mixture of methyl 3-(6-chloro-3-(chlorosulfonyl)-1H-indol-1-yl)-2-fluoropropanoate XII-4 (240 mg, 0.68 mmol), pyridine (3.0 mL), DMAP (8.3 mg, 0.068 mmol) and 4-bromo-2,5-difluoroaniline (170 mg, 0.82 mmol) was stirred at 70° C. overnight. After removal of the solvent under reduced pressure, the residue was extracted with EtOAc (50 mL) and washed with brine. The organic phase was dried over MgSO$_4$, filtered and concentrated under reduced pressure affording methyl 3-[3-[(4-bromo-2,5-difluoro-phenyl)sulfamoyl]-6-chloro-indol-1-yl]-2-fluoro-propanoate I-7a (143 mg) which was directly used for the next step without further purification or characterization.

Yield: 40%.

Step-2: Synthesis of N-(4-bromo-2,5-difluorophenyl)-6-chloro-1-(2-fluoro-3-hydroxypropyl)indole-3-sulfonamide I-7

To a solution of methyl 3-[3-[(4-bromo-2,5-difluoro-phenyl)sulfamoyl]-6-chloro-indol-1-yl]-2-fluoro-propanoate I-7a (26 mg, 0.05 mmol) in THF was added LiAlH$_4$ (3.0 mg, 0.6 mmol) at 0° C. The mixture was stirred at 0° C. overnight, quenched with H$_2$O (5.0 mL) and extracted with EtOAc (20 mL). The organic phase was washed with brine, dried over MgSO$_4$, filtered and concentrated under reduced pressure. The residue was purified by column chromatography on silica gel yielding N-(4-bromo-2,5-difluorophenyl)-6-chloro-1-(2-fluoro-3-hydroxypropyl)indole-3-sulfonamide I-7 as colorless crystals (18 mg).

Yield: 72%.

Neutral LCMS Method 2 (ES$^+$): 497 (M+H)$^+$, 96% purity.

$^1$H NMR (600 MHz, DMSO-d$_6$) δ 10.53 (s, 1H), 8.08 (s, 1H), 7.85-7.72 (m, 2H), 7.61 (dd, J=9.6, 6.4 Hz, 1H), 7.33-7.23 (m, 2H), 5.15 (s, 1H), 4.85-4.67 (m, 1H), 4.64-4.42 (m, 2H), 3.54 (dddd, J=55.9, 24.4, 12.4, 4.4 Hz, 2H).

E.3. Synthesis of N-(4-bromo-2,5-difluorophenyl)-6-chloro-1-(2-fluoro-3-hydroxypropyl)pyrrolo[2,3-b]pyridine-3-sulfonamide I-8

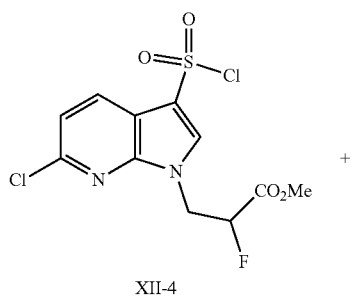

XII-4

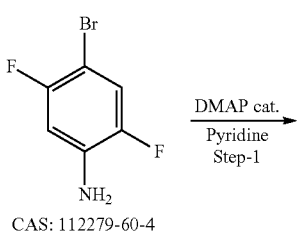

CAS: 112279-60-4

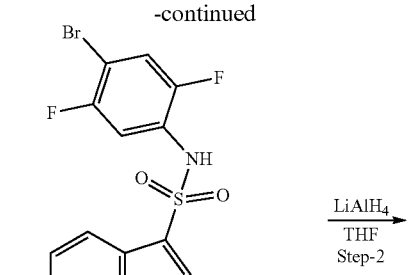

I-8a

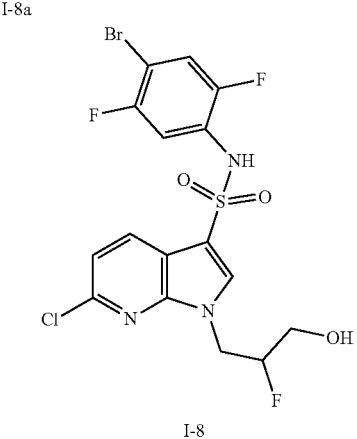

I-8

Step-1: Synthesis of methyl 3-(3-(N-(4-bromo-2,5-difluorophenyl)sulfamoyl)-6-chloro-1H-pyrrolo[2,3-b]pyridin-1-yl)-2-fluoropropanoate I-8a A mixture of methyl 3-(6-chloro-3-(chlorosulfonyl)-1H-pyrrolo[2,3-b]pyridin-1-yl)-2-fluoropropanoate XII-4 (225 mg, 0.64 mmol), pyridine (3.0 mL), DMAP (7.8 mg, 0.064 mmol) and 4-bromo-2,5-difluoroaniline (158 mg, 0.77 mmol) was stirred at 70° C. overnight. After removal of the solvent under reduced pressure, the residue was extracted with EtOAc (50 mL). The organic phase was washed with brine, dried over MgSO$_4$, filtered and concentrated under reduced pressure yielding methyl 3-(3-(N-(4-bromo-2,5-difluorophenyl)sulfamoyl)-6-chloro-1H-pyrrolo[2,3-b]pyridin-1-yl)-2-fluoropropanoate I-8a (189 mg). The crude intermediate was directly used for the next step without further purification or characterization.

Yield: 56%.

Step-2: Synthesis of N-(4-bromo-2,5-difluorophenyl)-6-chloro-1-(2-fluoro-3-hydroxypropyl)pyrrolo[2,3-b]pyridine-3-sulfonamide I-8

To a solution of methyl 3-(3-(N-(4-bromo-2,5-difluorophenyl)sulfamoyl)-6-chloro-1H-pyrrolo[2,3-b]pyridin-1-yl)-2-fluoropropanoate I-8a (43 mg, 0.08 mmol) in THF was added LiAlH$_4$ (4 mg, 0.9 mmol) at 0° C. The mixture was stirred at the same temperature overnight, subsequently quenched with H$_2$O (5.0 mL) and extracted with EtOAc (20 mL). The organic phase was washed with brine, dried over MgSO$_4$, filtered and concentrated under reduced pressure. The residue was purified by column chromatography on silica gel leading to N-(4-bromo-2,5-difluorophenyl)-6-chloro-1-(2-fluoro-3-hydroxypropyl)pyrrolo[2,3-b]pyridine-3-sulfonamide I-8 as colorless crystals (25 mg).

Yield: 62%.

Neutral LCMS Method 2 (ES+): 498 (M+H)+, 92% purity.

$^1$H NMR (600 MHz, DMSO-$d_6$) δ 8.08 (d, J=8.3 Hz, 1H), 7.80 (d, J=1.1 Hz, 1H), 7.46 (dd, J=9.1, 6.9 Hz, 1H), 7.29 (d, J=8.3 Hz, 1H), 7.15 (dd, J=9.2, 6.0 Hz, 1H), 6.84 (d, J=2.8 Hz, 1H), 4.98-4.77 (m, 1H), 4.69-4.50 (m, 2H), 3.71-3.54 (m, 2H), 2.68 (s, 1H).

E.4. Method B. Synthesis of N-(5-bromo-6-methoxypyridin-2-yl)-6-chloro-1-(2-hydroxyethyl)indole-3-sulfonamide I-9

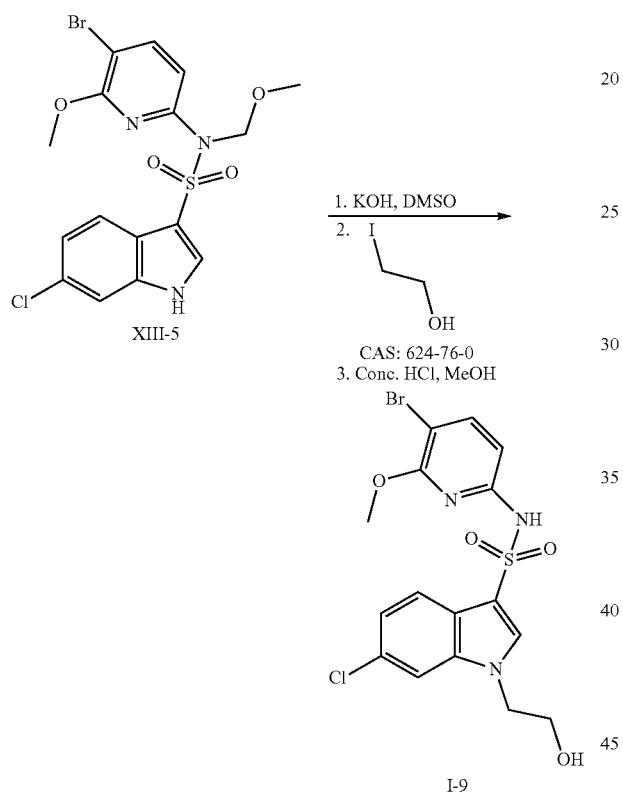

To a solution of N-(5-bromo-6-methoxypyridin-2-yl)-6-chloro-N-(methoxymethyl)-1H-indole-3-sulfonamide XIII-5 (0.16 g, 0.35 mmol) in dry dimethyl sulfoxide (5 mL) at 0° C. was added potassium hydroxide powder (90 mg, 1.57 mmol). The mixture was stirred for 15 min at the 0° C. and treated with 2-iodoethanol (90 mg, 0.52 mmol, 1.5 equiv) dropwise. After heating for 16 h at 60° C., the resulting mixture was poured onto ice water and extracted with ethyl acetate (3×50 mL). The combined organic extracts were washed with brine, dried over MgSO$_4$, filtered and concentrated under vacuum. Subsequently, the residue was dissolved in methanol (15 mL), treated with conc. HCl (5 equiv) and stirred for 16 h. The solvents were removed under reduced pressure and the residue was treated with ethyl acetate (50 mL) and a saturated solution of sodium hydrogen carbonate (50 mL). The organic layer was separated and the aqueous phase was extracted with ethyl acetate two times (2×50 mL). The combined organic extracts were washed with brine, dried over MgSO$_4$, filtered and concentrated under vacuum. Purification was performed by column chromatography on silica gel using mixtures of petroleum ether:ethyl acetate as eluents (gradient, 80:20 to 50:50) to afford 33 mg of N-(5-bromo-6-methoxypyridin-2-yl)-6-chloro-1-(2-hydroxyethyl)indole-3-sulfonamide I-9 as a white solid.

Yield: 21%.

Neutral LCMS Method 2 (ES+): 462 (M+H)+, 100% purity.

The following compounds in Table 2 may be synthesized according methods analogous to Method B.

TABLE 2

| No | Intermediate XIII | Alkylating agent | Temperature, Time (alkylation step) | Yield (%) |
|---|---|---|---|---|
| I-10 | XIII-1 | 624-76-0 | 60° C., 16 h | 49 |
| I-11 | XIII-1 | 105-36-2 | 60° C., 16 h | 52 |
| I-12 | XIII-1 | 74-88-4 | 60° C., 16 h | 65 |
| I-13 | XIII-1 | 624-70-4 | 60° C., 16 h | 44 |
| I-14 | XIII-1 | 627-32-7 | 60° C., 16 h | 28 |
| I-15 | XIII-1 | 107-99-3 | 60° C., 16 h | 15 |
| I-16 | XIII-1 | 628-89-7 | 60° C., 16 h | 42 |
| I-17 | XIII-1 | 78-95-5 | 60° C., 16 h | 43 |
| I-18 | XIII-1 | 127-00-4 | 60° C., 16 h | 48 |
| I-19 | XIII-1 | 453-11-2 | 60° C., 16 h | 30 |
| I-20 | XIII-1 | 148371-95-3 | 60° C., 16 h | 13 |
| I-21 | XIII-2 | 624-76-0 | 60° C., 16 h | 48 |
| I-22 | XIII-2 | 74-88-4 | 60° C., 16 h | 39 |
| I-23 | XIII-2 | 75-03-6 | 60° C., 16 h | 28 |
| I-24 | XIII-2 | 762-51-6 | 60° C., 16 h | 24 |
| I-25 | XIII-2 | 106-94-5 | 60° C., 16 h | 21 |
| I-26 | XIII-2 | 627-42-9 | 60° C., 16 h | 9 |
| I-27 | XIII-2 | 96-24-2 | 100° C., 84 h | 22 |
| I-28 | XIII-1 | 96-24-2 | 100° C., 84 h | 29 |
| I-29 | XIII-6 | 96-24-2 | 100° C., 84 h | 28 |
| I-30 | XIII-6 | 624-76-0 | 60° C., 16 h | 36 |
| I-31 | XIII-3 | 74-88-4 | 60° C., 16 h | 22 |
| I-32 | XIII-3 | 74427-22-8 | 60° C., 16 h | 75 |
| I-33 | XIII-3 | 453-11-2 | 60° C., 16 h | 25 |
| I-34 | XIII-3 | 96-24-2 | 100° C., 84 h | 51 |
| I-35 | XIII-4 | 624-76-0 | 60° C., 16 h | 9 |

N-(4-bromo-2,5-difluorophenyl)-6-chloro-1-(2-hydroxyethyl)indole-3-sulfonamide I-10

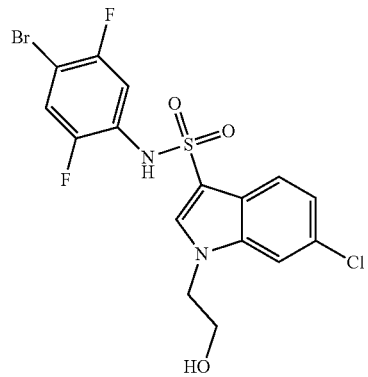 [SMILES: O=S(=O)(Nc1cc(F)c(Br)cc1F)c1cn(CCO)c2cc(Cl)ccc12]

Neutral LCMS Method 2 (ES+): 465/467 (M+H)+, 97% purity.

$^1$H NMR (600 MHz, DMSO-$d_6$) δ 10.49 (s, 1H), 8.06 (s, 1H), 7.78 (d, J=8.6 Hz, 2H), 7.60 (dd, J=9.7, 6.3 Hz, 1H), 7.28 (dd, J=9.9, 6.8 Hz, 1H), 7.24 (dd, J=8.5, 1.9 Hz, 1H), 4.87 (t, J=5.2 Hz, 1H), 4.26 (t, J=5.2 Hz, 2H), 3.66 (q, J=5.2 Hz, 2H).

2-[3-[(4-bromo-2,5-difluorophenyl)sulfamoyl]-6-chloroindol-1-yl]acetic acid I-11

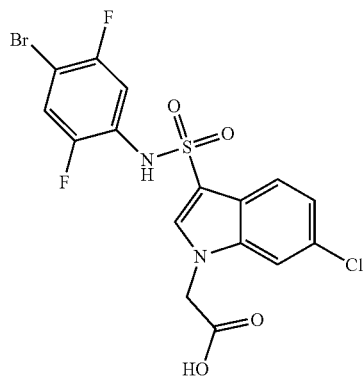 [SMILES: O=C(O)Cn1cc(S(=O)(=O)Nc2cc(F)c(Br)cc2F)c2ccc(Cl)cc21]

Neutral LCMS Method 2 (ES⁺): 479 (M+H)⁺, 96% purity.
$^1$H NMR (600 MHz, DMSO-d$_6$) δ 10.54 (s, 1H), 8.09 (s, 1H), 7.79 (d, J=8.6 Hz, 1H), 7.73 (s, 1H), 7.60 (dd, J=9.6, 6.4 Hz, 1H), 7.30-7.21 (m, 2H), 5.10 (s, 2H).

N-(4-bromo-2,5-difluorophenyl)-6-chloro-1-methyl-indole-3-sulfonamide I-12

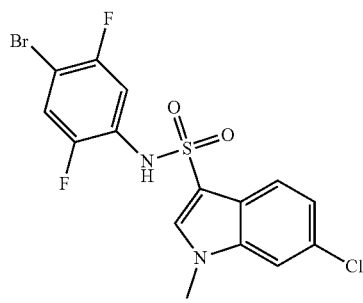

Neutral LCMS Method 2 (ES⁺): 435 (M+H)⁺, 96% purity.
$^1$H NMR (600 MHz, DMSO-d$_6$) δ 10.48 (d, J=10.3 Hz, 1H), 8.09 (s, 1H), 7.78 (d, J=8.6 Hz, 1H), 7.70 (d, J=1.8 Hz, 1H), 7.59 (dd, J=9.7, 6.4 Hz, 1H), 7.31 (dd, J=9.9, 6.9 Hz, 1H), 7.26 (dd, J=8.6, 1.9 Hz, 1H), 3.80 (s, 3H).

N-(4-bromo-2,5-difluorophenyl)-6-chloro-1-(2-chloroethyl)indole-3-sulfonamide I-13

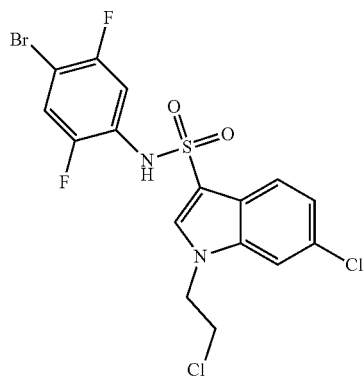

Neutral LCMS Method 2 (ES⁺): 483/485 (M+H)⁺, 96% purity.
$^1$H NMR (600 MHz, DMSO-d$_6$) δ 10.51 (s, 1H), 8.13 (s, 1H), 7.87-7.84 (m, 1H), 7.82 (d, J=8.6 Hz, 1H), 7.57 (dd, J=9.6, 6.4 Hz, 1H), 7.30-7.23 (m, 2H), 4.59 (t, J=5.6 Hz, 2H), 3.95 (t, J=5.6 Hz, 2H).

N-(4-bromo-2,5-difluorophenyl)-6-chloro-1-(3-hydroxypropyl)indole-3-sulfonamide I-14

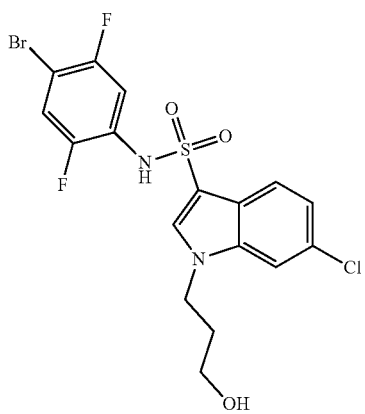 [SMILES: O=S(=O)(Nc1cc(F)c(Br)cc1F)c1cn(CCCO)c2cc(Cl)ccc12]

Neutral LCMS Method 2 (ES⁺): 479/481 (M+H)⁺, 98% purity.
$^1$H NMR (600 MHz, DMSO-d$_6$) δ 10.45 (s, 1H), 8.08 (s, 1H), 7.80-7.73 (m, 2H), 7.58 (dd, J=9.6, 6.4 Hz, 1H), 7.30-7.21 (m, 2H), 4.60 (t, J=5.1 Hz, 1H), 4.26 (t, J=6.8 Hz, 2H), 3.25 (q, J=5.7 Hz, 2H), 1.82 (p, J=6.5 Hz, 2H).

N-(4-bromo-2,5-difluorophenyl)-6-chloro-1-[2-(dimethylamino)ethyl]indole-3-sulfonamide I-15

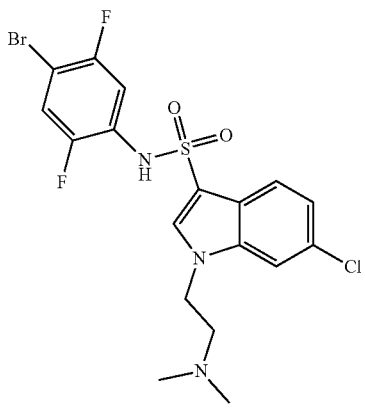 [SMILES: CN(C)CCn1cc(S(=O)(=O)Nc2cc(F)c(Br)cc2F)c2ccc(Cl)cc21]

Neutral LCMS Method 2 (ES⁺): 492/494 (M+H)⁺, 95% purity.
$^1$H NMR (600 MHz, DMSO-d$_6$) δ 8.05 (s, 1H), 7.81-7.77 (m, 2H), 7.55 (dd, J=9.7, 6.4 Hz, 1H), 7.28-7.22 (m, 2H), 4.29 (t, J=6.0 Hz, 2H), 2.58 (t, J=6.0 Hz, 2H), 2.12 (s, 3H), 1.39 (s, 3H), NH not seen.

N-(4-bromo-2,5-difluorophenyl)-6-chloro-1-[2-(2-hydroxyethoxy)ethyl]indole-3-sulfonamide I-16

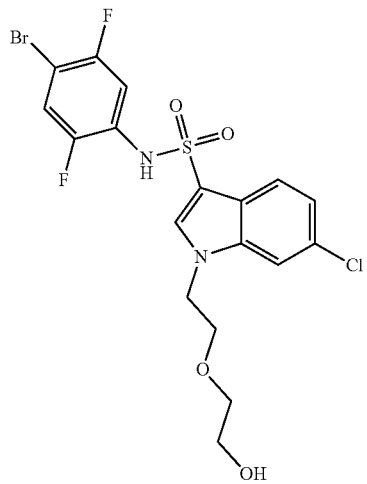 [SMILES: O=S(=O)(Nc1cc(F)c(Br)cc1F)c1cn(CCOCCO)c2cc(Cl)ccc12]

Neutral LCMS Method 2 (ES+): 509/511 (M+H)+, 95% purity.

¹H NMR (600 MHz, DMSO-d$_6$) δ 10.50 (s, 1H), 8.08 (s, 1H), 7.82-7.77 (m, 2H), 7.59 (dd, J=9.6, 6.4 Hz, 1H), 7.31-7.23 (m, 2H), 4.54 (t, J=5.4 Hz, 1H), 4.37 (t, J=5.1 Hz, 2H), 3.68 (t, J=5.1 Hz, 2H), 3.37 (t, J=5.4 Hz, 2H), 3.31 (d, J=4.7 Hz, 2H).

N-(4-bromo-2,5-difluorophenyl)-6-chloro-1-(2-oxopropyl)indole-3-sulfonamide I-17

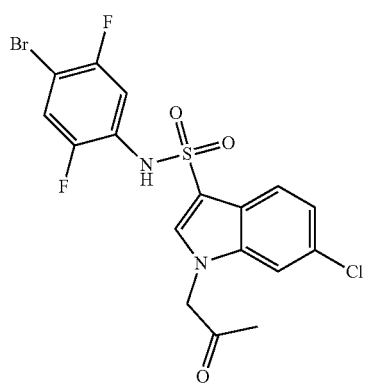 [SMILES: CC(=O)Cn1cc(S(=O)(=O)Nc2cc(F)c(Br)cc2F)c2ccc(Cl)cc21]

Neutral LCMS Method 2 (ES+): 477/479 (M+H)+, 95% purity.

¹H NMR (600 MHz, DMSO-d$_6$) δ 10.53 (s, 1H), 7.94 (s, 1H), 7.78 (d, J=8.6 Hz, 1H), 7.69 (d, J=1.8 Hz, 1H), 7.61 (dd, J=9.6, 6.3 Hz, 1H), 7.28-7.22 (m, 2H), 5.26 (s, 2H), 2.17 (s, 3H).

N-(4-bromo-2,5-difluorophenyl)-6-chloro-1-(2-hydroxypropyl)indole-3-sulfonamide I-18

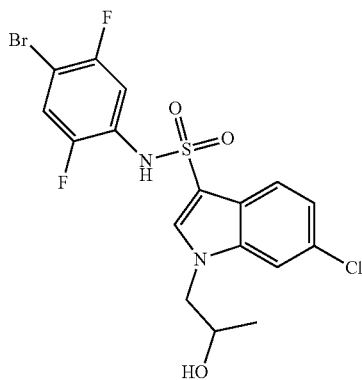 [SMILES: CC(O)Cn1cc(S(=O)(=O)Nc2cc(F)c(Br)cc2F)c2ccc(Cl)cc21]

Neutral LCMS Method 2 (ES+): 479/481 (M+H)+, 95% purity.

¹H NMR (600 MHz, DMSO-d$_6$) δ 10.49 (s, 1H), 8.02 (s, 1H), 7.77 (d, J=8.7 Hz, 2H), 7.58 (dd, J=9.7, 6.3 Hz, 1H), 7.27 (dd, J=9.9, 6.8 Hz, 1H), 7.23 (dd, J=8.5, 1.9 Hz, 1H), 4.88 (d, J=4.9 Hz, 1H), 4.19 (dd, J=14.1, 4.0 Hz, 2H), 4.05 (dd, J=14.2, 7.1 Hz, 1H), 0.97 (d, J=6.2 Hz, 3H).

N-(4-bromo-2,5-difluorophenyl)-6-chloro-1-(3-fluoro-2-hydroxypropyl)indole-3-sulfonamide I-19

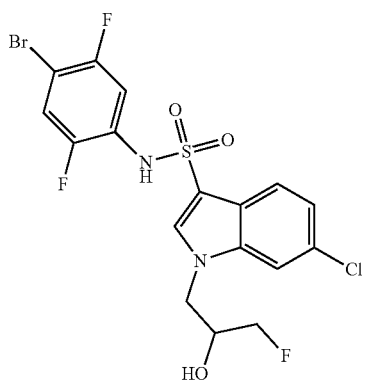 [SMILES: O=S(=O)(Nc1cc(F)c(Br)cc1F)c1cn(CC(O)CF)c2cc(Cl)ccc12]

Neutral LCMS Method 2 (ES+): 497/499 (M+H)+, 96% purity.

¹H NMR (600 MHz, DMSO-d$_6$) δ 10.51 (s, 1H), 8.03 (s, 1H), 7.78 (d, J=8.8 Hz, 2H), 7.59 (dd, J=9.6, 6.3 Hz, 1H), 7.31-7.22 (m, 2H), 5.44 (d, J=5.6 Hz, 1H), 4.39-4.32 (m, 2H), 4.32-4.27 (m, 1H), 4.20 (ddd, J=22.5, 12.0, 6.6 Hz, 2H).

81

N-(4-bromo-2,5-difluorophenyl)-6-chloro-1-(3,3,3-trifluoro-2-hydroxypropyl)indole-3-sulfonamide I-20

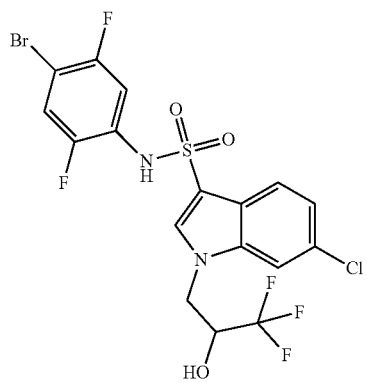 [SMILES: O=S(=O)(Nc1cc(F)c(Br)cc1F)c1cn(CC(O)C(F)(F)F)c2cc(Cl)ccc12]

Neutral LCMS Method 2 (ES+): 533 (M+H)+, 94% purity.
¹H NMR (600 MHz, DMSO-d₆) δ 10.54 (s, 1H), 8.12 (s, 1H), 7.82-7.75 (m, 2H), 7.59 (dd, J=9.6, 6.4 Hz, 1H), 7.28 (d, J=2.0 Hz, 2H), 6.60 (d, J=6.3 Hz, 1H), 4.54 (d, J=10.9 Hz, 1H), 4.43-4.35 (m, 2H).

6-chloro-N-[4-(difluoromethoxy)-2,5-difluorophenyl]-1-(2-hydroxyethyl)indole-3-sulfonamide I-21

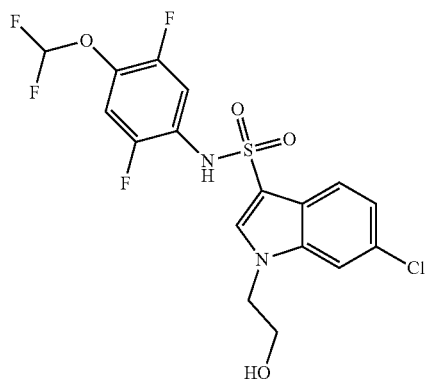 [SMILES: O=S(=O)(Nc1cc(F)c(OC(F)F)cc1F)c1cn(CCO)c2cc(Cl)ccc12]

Neutral LCMS Method 2 (ES+): 453 (M+H)+, 97% purity.
¹H NMR (600 MHz, DMSO-d₆) δ 10.33 (s, 1H), 8.01 (s, 1H), 7.76 (d, J=1.8 Hz, 1H), 7.71 (d, J=8.6 Hz, 1H), 7.31-7.26 (m, 2H), 7.22 (dd, J=8.6, 1.8 Hz, 1H), 7.08 (d, J=72.9 Hz, 1H), 4.88 (t, J=5.2 Hz, 1H), 4.26 (t, J=5.2 Hz, 2H), 3.66 (q, J=5.2 Hz, 2H).

82

6-chloro-N-[4-(difluoromethoxy)-2,5-difluorophenyl]-1-methylindole-3-sulfonamide I-22

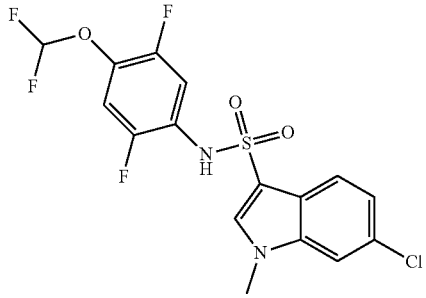 [SMILES: Cn1cc(S(=O)(=O)Nc2cc(F)c(OC(F)F)cc2F)c2ccc(Cl)cc21]

Neutral LCMS Method 2 (ES+): 423 (M+H)+, 95% purity.
¹H NMR (600 MHz, DMSO-d₆) δ 10.35 (s, 1H), 8.05 (s, 1H), 7.74-7.69 (m, 2H), 7.33-7.28 (m, 2H), 7.24 (dd, J=8.5, 1.9 Hz, 1H), 7.09 (d, J=73.0 Hz, 1H), 3.80 (s, 3H).

6-chloro-N-[4-(difluoromethoxy)-2,5-difluorophenyl]-1-ethylindole-3-sulfonamide I-23

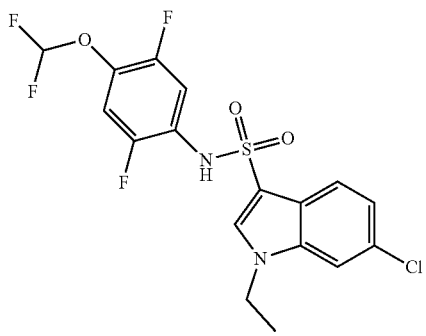 [SMILES: CCn1cc(S(=O)(=O)Nc2cc(F)c(OC(F)F)cc2F)c2ccc(Cl)cc21]

Neutral LCMS Method 2 (ES+): 437 (M+H)+, 95% purity.
¹H NMR (600 MHz, DMSO-d₆) δ 10.29 (s, 1H), 8.08 (s, 1H), 7.78 (d, J=1.8 Hz, 1H), 7.72 (d, J=8.7 Hz, 1H), 7.31-7.24 (m, 2H), 7.23 (dd, J=8.6, 1.8 Hz, 1H), 7.08 (d, J=72.8 Hz, 1H), 4.24 (q, J=7.2 Hz, 2H), 1.29 (d, J=7.2 Hz, 3H).

6-chloro-N-[4-(difluoromethoxy)-2,5-difluorophenyl]-1-(2-fluoroethyl)indole-3-sulfonamide I-24

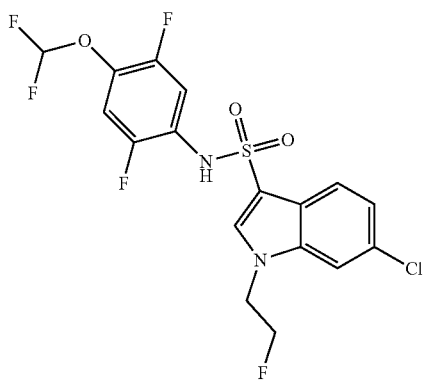 [SMILES: O=S(=O)(Nc1cc(F)c(OC(F)F)cc1F)c1cn(CCF)c2cc(Cl)ccc12]

83

Neutral LCMS Method 2 (ES⁺): 455 (M+H)⁺, 97% purity.
¹H NMR (600 MHz, DMSO-$d_6$) δ 10.34 (s, 1H), 8.05 (s, 1H), 7.81 (d, J=1.8 Hz, 1H), 7.73 (d, J=8.6 Hz, 1H), 7.29-7.23 (m, 3H), 7.07 (d, J=72.9 Hz, 1H), 4.62-4.73 (m, 2H), 4.53-4.62 (m, 2H).

6-chloro-N-[4-(difluoromethoxy)-2,5-difluorophenyl]-1-propylindole-3-sulfonamide I-25

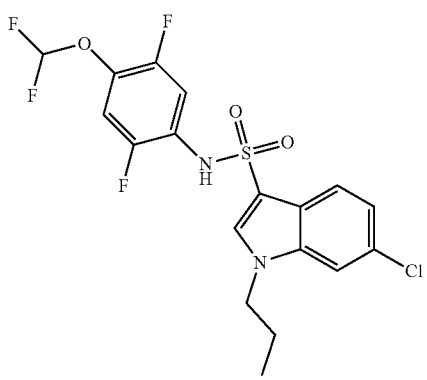 [SMILES: CCCn1cc(S(=O)(=O)Nc2cc(F)c(OC(F)F)cc2F)c2ccc(Cl)cc21]

Neutral LCMS Method 2 (ES⁺): 451 (M+H)+. 99% purity.
¹H NMR (600 MHz, DMSO-$d_6$) δ 10.30 (s, 1H), 8.05 (s, 1H), 7.78 (d, J=1.8 Hz, 1H), 7.73 (d, J=8.7 Hz, 1H), 7.27 (ddd, J=10.5, 7.3, 3.2 Hz, 2H), 7.23 (dd, J=8.6, 1.8 Hz, 1H), 7.07 (d, J=72.8 Hz, 1H), 4.17 (t, J=6.8 Hz, 2H), 1.68 (h, J=7.2 Hz, 2H), 0.66 (t, J=7.3 Hz, 3H).

6-chloro-N-[4-(difluoromethoxy)-2,5-difluorophenyl]-1-(2-methoxyethyl)indole-3-sulfonamide I-26

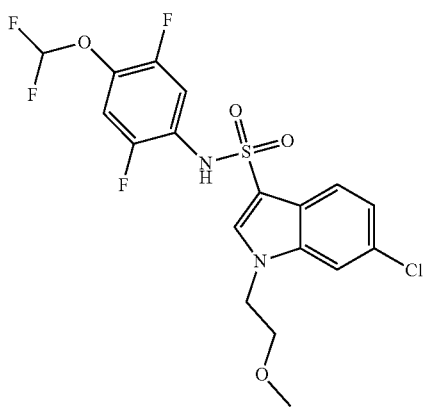 [SMILES: COCCn1cc(S(=O)(=O)Nc2cc(F)c(OC(F)F)cc2F)c2ccc(Cl)cc21]

Neutral LCMS Method 2 (ES⁺): 467 (M+H)⁺, 97% purity.
¹H NMR (600 MHz, DMSO-$d_6$) δ 10.35 (s, 1H), 7.99 (s, 1H), 7.79 (s, 1H), 7.74 (d, J=8.6 Hz, 1H), 7.31-7.22 (m, 3H), 7.08 (d, J=72.9 Hz, 1H), 4.38 (t, J=5.1 Hz, 2H), 3.58 (t, J=5.0 Hz, 2H), 3.12 (s, 3H).

84

6-chloro-N-[4-(difluoromethoxy)-2,5-difluorophenyl]-1-(2,3-dihydroxypropyl)indole-3-sulfonamide I-27

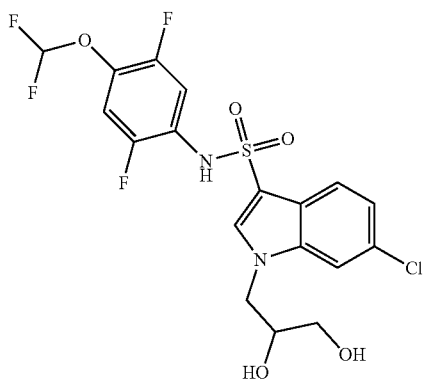 [SMILES: O=S(=O)(Nc1cc(F)c(OC(F)F)cc1F)c1cn(CC(O)CO)c2cc(Cl)ccc12]

Neutral LCMS Method 2 (ES⁺): 483 (M+H)⁺, 98% purity.
¹H NMR (600 MHz, DMSO-$d_6$) δ 10.33 (s, 1H), 7.94 (s, 1H), 7.75-7.69 (m, 2H), 7.32-7.25 (m, 2H), 7.22 (d, J=8.5 Hz, 1H), 7.08 (d, J=72.9 Hz, 1H), 5.01 (d, J=5.3 Hz, 1H), 4.79 (t, J=5.6 Hz, 1H), 4.31-4.09 (m, 2H), 3.72 (s, 1H), 3.18 (dt, J=10.6, 6.2 Hz, 2H).

N-(4-bromo-2,5-difluorophenyl)-6-chloro-1-(2,3-dihydroxypropyl)indole-3-sulfonamide I-28

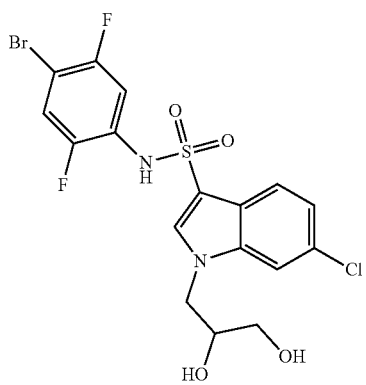 [SMILES: O=S(=O)(Nc1cc(F)c(Br)cc1F)c1cn(CC(O)CO)c2cc(Cl)ccc12]

Neutral LCMS Method 2 (ES⁺): 495/497 (M+H)⁺, 98% purity.
¹H NMR (600 MHz, DMSO-$d_6$) δ 10.48 (s, 1H), 8.00 (s, 1H), 7.77 (d, J=8.6 Hz, 1H), 7.72 (d, J=1.8 Hz, 1H), 7.59 (dd, J=9.6, 6.4 Hz, 1H), 7.31-7.21 (m, 2H), 5.00 (d, J=5.2 Hz, 1H), 4.32 (dd, J=14.3, 3.5 Hz, 1H), 4.11 (dd, J=14.4, 7.3 Hz, 1H), 3.38-3.35 (m, 2H), 3.26-3.15 (m, 2H).

85

N-(4-bromo-2,5-difluorophenyl)-6-chloro-1-(2,3-dihydroxypropyl)pyrrolo[2,3-b]pyridine-3-sulfonamide I-29

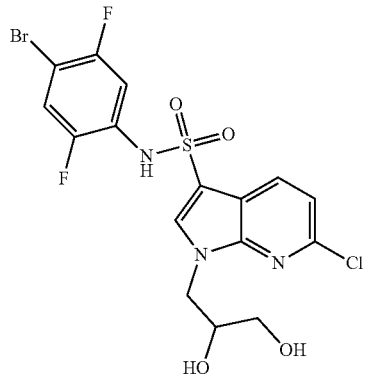

Neutral LCMS Method 2 (ES⁺): 496/498 (M+H)⁺, 99% purity.

$^1$H NMR (600 MHz, DMSO-d$_6$) δ 10.55 (s, 1H), 8.22-8.12 (m, 2H), 7.63-7.56 (m, 1H), 7.39 (dd, J=8.3, 1.1 Hz, 1H), 7.29 (ddd, J=9.8, 6.8, 1.1 Hz, 1H), 5.01-4.95 (m, 1H), 4.76 (t, J=5.5 Hz, 1H), 4.40 (dd, J=13.9, 3.8 Hz, 1H), 4.16-3.77 (m, 2H), 3.34 (d, J=1.2 Hz, 2H).

N-(4-bromo-2,5-difluorophenyl)-6-chloro-1-(2-hydroxyethyl)pyrrolo[2,3-b]pyridine-3-sulfonamide I-30

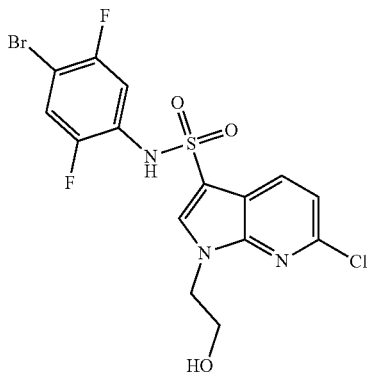 [SMILES: O=S(=O)(Nc1cc(F)c(Br)cc1F)c1cn(CCO)c2nc(Cl)ccc12]

Neutral LCMS Method 2 (ES⁺): 466/468 (M+H)⁺, 98% purity.

$^1$H NMR (600 MHz, DMSO-d$_6$) δ 10.67-10.33 (m, 1H), 8.22 (s, 1H), 8.19 (d, J=8.3 Hz, 1H), 7.62 (dd, J=9.6, 6.4 Hz, 1H), 7.40 (d, J=8.3 Hz, 1H), 7.30 (dd, J=9.7, 6.8 Hz, 1H), 4.92-4.86 (m, 1H), 4.31-4.25 (m, 2H), 3.74-3.69 (m, 2H).

86

6-chloro-N-(6-chloro-5-fluoro-2-methoxypyridin-3-yl)-1-methylindole-3-sulfonamide I-31

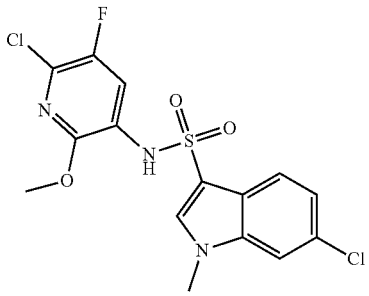 [SMILES: COc1nc(Cl)c(F)cc1NS(=O)(=O)c1cn(C)c2cc(Cl)ccc12]

Neutral LCMS Method 2 (ES⁺): 404 (M+H)⁺, 96% purity.
$^1$H NMR (600 MHz, DMSO-d$_6$) δ 10.14 (s, 1H), 8.11 (s, 1H), 7.82 (d, J=8.6 Hz, 1H), 7.72-7.68 (m, 2H), 7.26 (dd, J=8.6, 1.9 Hz, 1H), 3.80 (s, 3H), 3.54 (s, 3H).

6-chloro-N-(6-chloro-5-fluoro-2-methoxypyridin-3-yl)-1-(2,2-difluoroethyl)indole-3-sulfonamide I-32

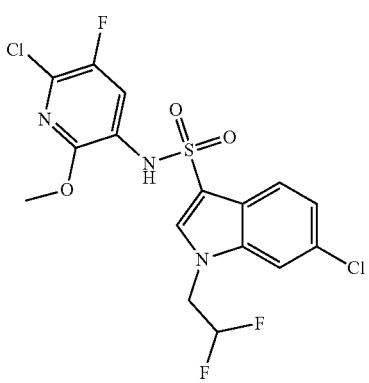 [SMILES: COc1nc(Cl)c(F)cc1NS(=O)(=O)c1cn(CC(F)F)c2cc(Cl)ccc12]

Neutral LCMS Method 2 (ES⁺): 454 (M+H)⁺, 99% purity.
$^1$H NMR (600 MHz, DMSO-d$_6$) δ 10.17 (s, 1H), 8.05 (s, 1H), 7.87-7.78 (m, 2H), 7.68 (d, J=9.0 Hz, 1H), 7.29 (dd, J=8.6, 1.8 Hz, 1H), 6.37 (tt, J=54.6, 3.2 Hz, 1H), 4.78 (td, J=15.8, 3.2 Hz, 2H), 3.46 (d, J=0.6 Hz, 3H).

6-chloro-N-(6-chloro-5-fluoro-2-methoxypyridin-3-yl)-1-(3-fluoro-2-hydroxypropyl)indole-3-sulfonamide I-33

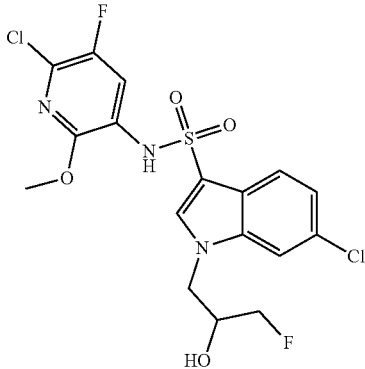 [SMILES: COc1nc(Cl)c(F)cc1NS(=O)(=O)c1cn(CC(O)CF)c2cc(Cl)ccc12]

Neutral LCMS Method 2 (ES+): 466 (M+H)+, 95% purity.

¹H NMR (600 MHz, DMSO-d₆) δ 10.14 (s, 1H), 8.04 (s, 1H), 7.79 (dd, J=15.4, 5.1 Hz, 2H), 7.66 (d, J=9.3 Hz, 1H), 7.25 (dd, J=8.5, 1.7 Hz, 1H), 5.42 (d, J=5.6 Hz, 1H), 4.41-4.29 (m, 2H), 4.29-4.14 (m, 2H), 3.55 (s, 3H), 3.35 (s, 1H).

6-chloro-N-(6-chloro-5-fluoro-2-methoxypyridin-3-yl)-1-(2,3-dihydroxypropyl)indole-3-sulfonamide I-34

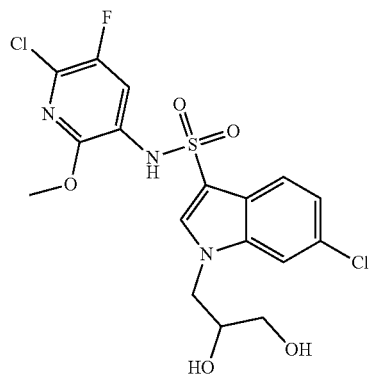 [SMILES: COc1nc(Cl)c(F)cc1NS(=O)(=O)c1cn(CC(O)CO)c2cc(Cl)ccc12]

Neutral LCMS Method 2 (ES+): 464 (M+H)+, 99% purity.

¹H NMR (600 MHz, DMSO-d₆) δ 10.11 (s, 1H), 8.02 (s, 1H), 7.82-7.78 (m, 1H), 7.72 (d, J=1.6 Hz, 1H), 7.67 (d, J=9.1 Hz, 1H), 7.24 (dd, J=8.5, 1.9 Hz, 1H), 4.98 (d, J=5.3 Hz, 1H), 4.78 (dd, J=6.0, 5.1 Hz, 1H), 4.35-4.07 (m, 2H), 3.55 (s, 3H), 3.38-3.31 (m, 2H), 3.23-3.16 (m, 1H).

6-chloro-N-[6-(difluoromethoxy)-5-fluoro-2-methoxypyridin-3-yl]-1-(2-hydroxyethyl)pyrrolo[2,3-b]pyridine-3-sulfonamide I-35

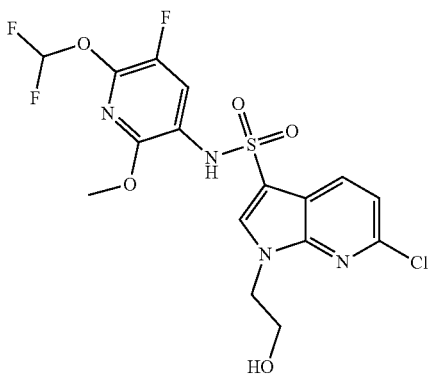 [SMILES: COc1nc(OC(F)F)c(F)cc1NS(=O)(=O)c1cn(CCO)c2nc(Cl)ccc12]

Neutral LCMS Method 2 (ES+): 467 (M+H)+, 96% purity.

¹H NMR (600 MHz, DMSO-d₆) δ 9.94 (s, 1H), 8.16-8.14 (m, 1H), 8.09 (s, 1H), 7.75-7.72 (m, 1H), 7.51 (d, J=72.1 Hz, 1H), 7.38 (d, J=8.3 Hz, 1H), 4.90 (t, J=5.3 Hz, 1H), 4.27 (t, J=5.5 Hz, 2H), 3.71 (q, J=5.5 Hz, 2H), 3.37 (s, 3H).

E.5. Synthesis of 1-(2-azidoethyl)-N-(4-bromo-2,5-difluorophenyl)-6-chloroindole-3-sulfonamide I-36

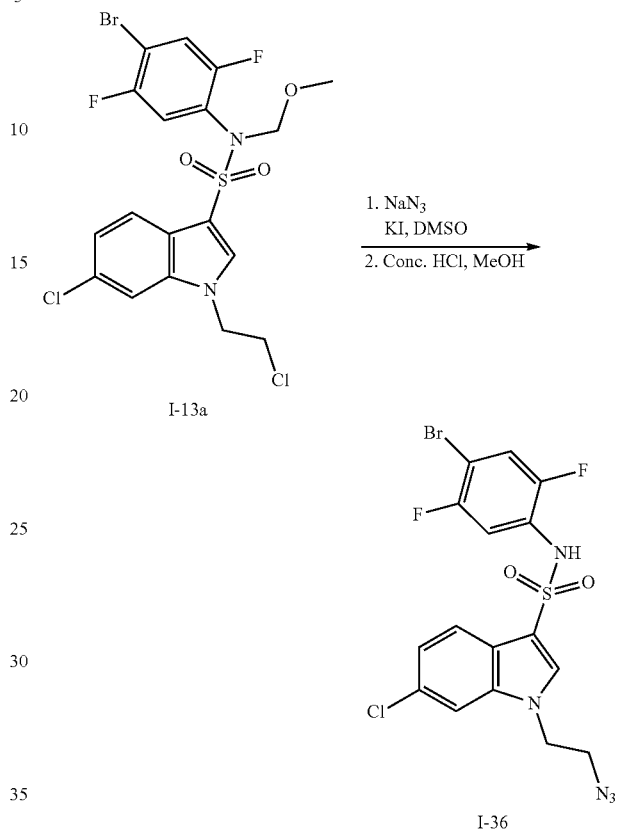

A solution of N-(4-bromo-2,5-difluorophenyl)-6-chloro-1-(2-chloroethyl)-N-(methoxymethyl)-1H-indole-3-sulfonamide I-13a (200 mg, 0.38 mmol) in 5 mL of dry dimethyl sulfoxide was treated with potassium iodide (75 mg, 0.45 mmol) and sodium azide (30 mg, 0.45 mmol) and heated for 16 h at 80° C. The mixture was poured into ice-water and the precipitate was filtered under reduced pressure affording 1-(2-azidoethyl)-N-(4-bromo-2,5-difluorophenyl)-6-chloro-N-(methoxymethyl)-1H-indole-3-sulfonamide, which was characterized only by TLC (one clear spot for the product) and directly used for the next step. The intermediate thus obtained was dissolved in methanol (15 mL), treated with conc. HCl (5 equiv) and stirred for 16 h. The solvents were removed under reduced pressure and the residue was treated with ethyl acetate (50 mL) and a saturated solution of sodium hydrogen carbonate (50 mL). The organic layer was separated and the aqueous phase was extracted with ethyl acetate (2×50 mL). The combined organic layers were washed with brine, dried over MgSO₄, filtered, and concentrated under vacuum to afford 140 mg of 1-(2-azidoethyl)-N-(4-bromo-2,5-difluorophenyl)-6-chloroindole-3-sulfonamide I-36 as a colorless solid.

Yield: 75% over two steps.

Neutral LCMS Method 2 (ES+): 490/492 (M+H)+, 96% purity.

¹H NMR (600 MHz, DMSO-d₆) δ 10.52 (s, 1H), 8.13 (s, 1H), 7.85 (d, J=1.9 Hz, 1H), 7.81 (d, J=8.6 Hz, 1H), 7.57 (dd, J=9.7, 6.4 Hz, 1H), 7.30-7.24 (m, 2H), 4.42 (t, J=5.6 Hz, 2H), 3.74-3.66 (m, 2H).

FURTHER EXAMPLES

Additional compounds can be prepared following the routes described herein. By these methods, examples can be prepared using a variety of indoles or azaindoles as starting materials. For example, instead of 6-chloroindol and 6-chloro-1H-pyrrolo[2,3-b]pyridine used for the synthesis of the specific examples described above, corresponding starting compounds can be used having other residues in R6 position. Non-limiting examples of such starting materials are 6-(difluoromethyl)-1H-pyrrolo[2,3-b]pyridine, 6-(trifluoromethyl)-1H-pyrrolo[2,3-b]pyridine, 6-bromo-pyrrolo[2,3-b]pyridine, 6-(difluoromethoxy)-1H-indole, 6-bromo-1H-indole, 6-cyclopropyl-1H-indole or 1H-indole-6-carbonitrile, which are further described in WO 2018/122232 and WO 2019/243303.

In one embodiment, additional examples can be synthesized as described in the general methods by (i) first introducing a protecting group P1 to compounds of formula XIII-P2 and then removing group P2 to give compounds of structure XIII-P1 according to the general scheme:

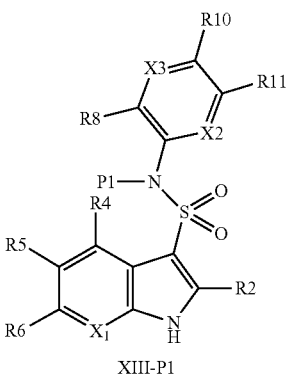

and as further exemplified herein, and subsequently (ii) alkylating compounds of Formula XIII-P1 with a hydroxyethyl halide (such as hydroxyethyl iodide) wherein P1 is a protecting group such as a methoxymethyl (like it was exemplified for 1-9, 1-21, 1-30, 1-35) according to the equation:

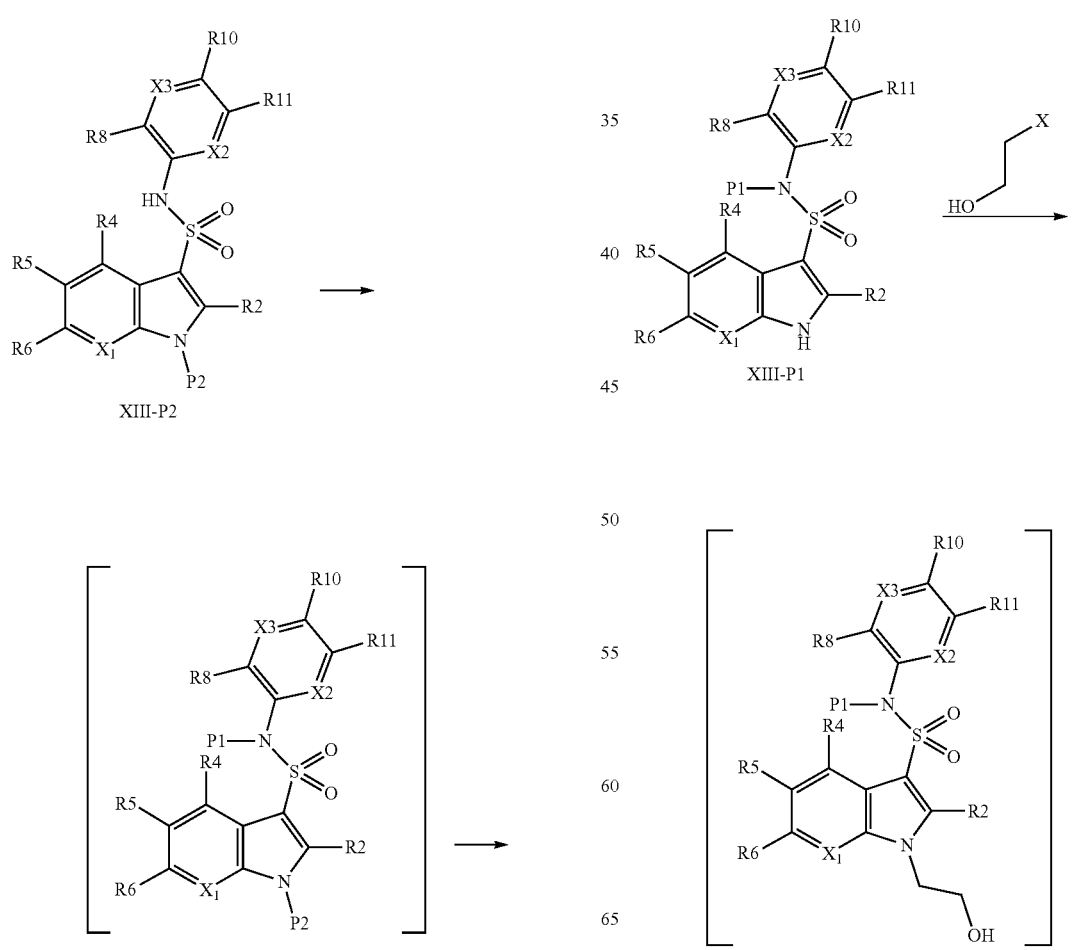

-continued

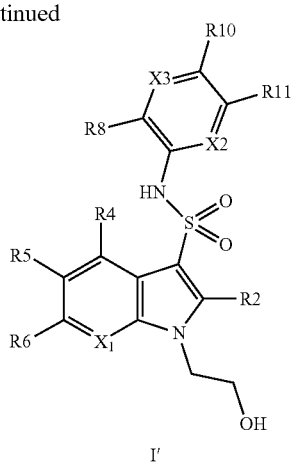

wherein R2, R4, R5, R6, R8, R10, R11, X1, X2 and X3 are as described herein.

Suitable alternative compounds XIII-P2 for use in this method, and their precursors and manufacturing routes are described e.g. in WO 2018-122232 and WO 2019/243303.

The inventors of the present invention expect the resulting compounds to have good GPR17 modulation activity as described for the other compounds herein.

Examples were tested and activities in $Ca^{2+}$ and cAMP assays are reported in the Table 3 further below.

B. Biology/Pharmacology

B-I. Cell Cultures

GPR17 Recombinant Cell Line:

Flp-In T-REx CHO cells stably expressing human GPR17 receptor (CHO hGPR17) from Evi Kostenis' lab (Bonn University, Germany) were cultured at 37° C. in a humidified atmosphere of 5% $CO_2$. Cells were grown in DMEM with Nutrient Mixture F-12 supplemented with hygromycin B (500 µg/ml) and blasticidin (30 µg/ml). Expression from the Flp-In locus was induced by treatment with doxycycline (1 µg/ml) for 16-20 h prior assays.

Primary Oligodendrocytes:

Primary oligodendrocyte progenitor cells (OPCs) were isolated from the forebrains of Wistar rat pups at postnatal day 0 to 2. Cerebra were mechanically dissociated with a syringe and two different hollow needles (first 1.2×40 and then 0.60×30). Clump-free cell suspension was filtered through a 70-µm cell strainer and plated into poly-D-lysine-coated 75-cm² culture flasks in DMEM supplemented with 10% (v/v) heat-inactivated fetal calf serum, penicillin (100 units/ml), and streptomycin (0.1 mg/ml) with medium exchanged every second day. After 8 to 11 days at 37° C. in a humidified atmosphere of 5% $CO_2$, mixed cultures were shaken at 240 rpm for 14-24 h to detach OPCs from astrocytes and microglia. To further enrich for OPCs, the suspension was plated onto uncoated Petri dishes for 45 min. Then, OPCs were seeded into poly-L-ornithine-coated plates and maintained at 37° C. in a humidified atmosphere of 5% $CO_2$ in proliferating Neurobasal medium supplemented with 2% (v/v) B27, 2 mM GlutaMAX, 100 units/ml penicillin, 0.1 mg/ml streptomycin, 10 ng/ml PDGF-AA, and 10 ng/ml basic FGF changing the medium every second day.

B-II: Functional In Vitro GPR17 Assays

B-II-A: Calcium Mobilization Functional Assay

GPR17 is a G-protein coupled receptor. GPR17 activation triggers Gq-type G-protein signaling resulting in endoplasmic reticulum calcium ($Ca^{2+}$) stores release in cytosol which can be measured using Calcium 5 dye, a fluorescent indicator dye of cytosolic $Ca^{2+}$ levels. The compounds of the present invention were assessed either in the $Ca^{2+}$ assay or in the GPR17 cAMP assay, described further below. Some representative examples were measured in both activity tests as indicated in Table 3, below.

Description of $Ca^{2+}$ Assay:

CHO hGPR17 were defrosted and seeded at a density of 20,000 cells per well into black 384-well plates with clear bottom. Cells were incubated overnight at 37° C. in a humidified atmosphere of 5% $CO_2$. Sixteen to twenty hours after seeding, CHO hGPR17 were loaded for 60 min with Calcium 5 dye, a cytosolic $Ca^{2+}$ indicator fluorescent dye, according to manufacturer's instructions. Fluorescent signal relative to cytosolic $Ca^{2+}$ concentration was recorded over time at room temperature in FLIPR Tetra reader. Cells were first incubated for 30 minutes at room temperature in HBSS Hepes buffer pH 7.4 containing increasing concentrations of test compounds (typically $10^{-11}$M to $10^{-6}$M). Then, 50 nM MDL29,951, a GPR17 agonist, was added to the cells. Inhibitory effects of varying concentrations test compounds were measured and resulting $pIC_{50}$s were determined. All incubations were performed in duplicate and results were compared to a concentration response curve of GPR17 agonist and antagonist reference compounds. Analysis and curve fitting were performed in ActivityBase XE using XLfit 4-parameter logistic equation $y=A+((B-A)/(1+((C/x)^D)))$ where A, B, C and D stand for minimum y, maximum y, $IC_{50}$ and slope, respectively.

Results of $Ca^{2+}$ Assay:

When tested in $Ca^{2+}$ mobilization assay, compounds of the Examples typically exhibit values of $pIC_{50}$ greater than or equal to 6.5; more preferably greater than or equal to 7.5, and even more preferably greater than or equal to 8.5. The activities of the Example compounds tested are depicted in the table 3 in Section B-IIB below. The activity ranges A, B and C refer to $pIC_{50}$ values in the $Ca^{2+}$ assay as follows: "A": $pIC_{50}$ 6.5≤x<7.5, "B": $pIC_{50}$ 7.5≤x<8.5, "C": 8.5≤$pIC_{50}$ B-IIB. cAMP Accumulation Functional Assay GPR17 activation can also recruit Gi-type G-protein signaling, resulting in a decrease of intracellular cyclic adenosine monophosphate (cAMP). Intracellular cAMP changes can be measured using the HTRF cAMP dynamic assay kit from CisBio (Codolet, France). Using homogenous time-resolved fluorescence technology (HTRF), the assay is based on competition between native cAMP produced by cells and cAMP labelled with the dye d2. The tracer binding was determined by an anti-cAMP antibody labeled with cryptate.

Description of cAMP Assay

CHO hGPR17 were detached with PBS containing EDTA and dispatched in black 384-well plates with 5,000 cells per well. Cells were first incubated for 30 minutes at room temperature in HBSS Hepes (pH 7.4) containing vehicle or varying concentrations of test GPR17 antagonist/inverse agonist compounds. Then, a dose response curve of MDL29, 951 GPR17 agonist (typically from $10^{-5}$M to $10^{-10}$M) was added on vehicle and on each test GPR17 antagonist/inverse agonist compound concentration in a final volume of 20 µL HBSS Hepes buffer (pH 7.4) containing 1% DMSO, 5 µM forskolin and 0.1 mM IBMX. After 60 minutes incubation at room temperature, the reaction is terminated and the cells lysed by adding the d2 detection reagent and the cryptate reagent in 10 µL lysis buffer each according to manufacturer's instructions. After 60 minutes incubation, changes in cAMP concentrations are measured according to manufacturer's instructions using an Envision plate reader with laser excitation. All incubations were performed in duplicate. Data was analyzed using GraphPad Prism software using the 4-parameter logistic equation to measure MDL29,951 $pEC_{50}$s in absence and presence of GPR17 antagonist/inverse agonist test compounds. Dose ratio (DR) were plotted against antagonist concentrations and Schild analysis provided estimated affinity $pA_2$ of GPR17 antagonist/inverse agonist test compounds.

Results of cAMP Assay:

When tested in cAMP assay, compounds of the Examples typically exhibit values of $pA_2$ greater than or equal to 6.5; preferably greater than or equal to 7.5; more preferably greater than or equal to 8.5. The activities of the Example compounds tested are depicted in the table below. The activity ranges A, B and C refer to $pA_2$ values in the cAMP assay as follows: "A": $pA_2$ 6.5≤x<7.5, "B": $pA_2$ 7.5≤x<8.5, "C": 8.5≤$pA_2$.

The following table 3 shows the $pIC_{50}$ and $pA_2$ values of the Example compounds tested in the $Ca_{2+}$ and the cAMP assay. Blanks in the $pA_2$ or the $Ca^{2+}$ assay columns indicate that the respective compound was not yet tested in the respective assay, or that the result was not yet available.

TABLE 3

| Ex No | $Ca^{2+}$ assay $pIC_{50}$ | cAMP assay $pA_2$ |
|---|---|---|
| I-1 | A | |
| I-2 | A | |
| I-3 | | B |
| I-4 | | B |
| I-5 | | A |
| I-6 | | A |
| I-7 | | B |
| I-8 | | A |
| I-9 | | A |
| I-10 | | B |
| I-11 | | C |
| I-12 | | B |
| I-13 | | A |
| I-14 | | A |
| I-15 | | A |
| I-16 | | B |
| I-17 | | A |
| I-18 | | C |
| I-19 | | B |
| I-20 | | B |
| I-21 | | B |
| I-22 | | B |
| I-23 | | A |
| I-24 | | B |
| I-25 | | A |
| I-26 | | A |
| I-27 | | C |
| I-28 | | B |
| I-29 | | B |
| I-30 | | B |
| I-31 | | B |
| I-32 | | B |
| I-33 | | C |
| I-34 | | B |
| I-35 | | C |
| I-36 | | A |

B-IIC: Oligodendrocyte Maturation/Myelination Assays

The effects of negative modulators of GPR17 on primary oligodendrocytes maturation/myelination can be assessed in vitro by immunoassays using antibodies directed against Myelin Basic Protein (MBP), as marker for mature oligodendrocytes.

Description of MBP Western Blot/Oligodendrocyte/Myelination Assay

After 3-4 days in proliferation medium, rat primary OPCs were seeded at 25,000 cells per $cm^2$ in 12-well tissue culture plates and switched to growth factor-free Neurobasal medium to induce spontaneous in vitro differentiation and GPR17 protein expression. For terminal differentiation and quantification analyses of protein expression, after 24-48 h the growth factor-free medium was supplemented with 0.20 ng/mL triiodothyronine (T3) and 10 ng/mL ciliary neurotrophic factor together with 1 µM GPR17 antagonist/inverse agonists test compounds or vehicle for additional 3 days. Following compound treatment, cells were washed twice with ice-cold PBS and lysed in ice-cold lysis buffer (25 mM Tris, pH 7.4, 150 mM NaCl, 1 mM EDTA, 1% Triton X-100, 1% IGEPAL) supplemented with protease inhibitor mixture. Lysates were rotated 20 min at 4° C. and centrifuged at 15,000×g at 4° C. for 10 min. Protein concentration was determined using the Pierce BCA Protein Assay according to manufacturer's instructions. 7.5-15 µg of protein were separated by 10% SDS-polyacrylamide gel electrophoresis and transferred to nitrocellulose membrane by electroblotting. After washing, membranes were blocked with Roti-Block for 1 h at room temperature and incubated overnight at 4° C. in Roti-Block with MBP antibody (1:5000, LifeSpan Biosciences). Membranes were washed 3 times with PBS containing 0.1% Tween and then incubated for 1 h at room temperature with a horseradish peroxidase-conjugated goat anti-mouse IgG antibody in Roti-Block. The immunoreactive proteins were visualized by chemiluminescence using Amersham Biosciences ECL Prime Western blotting detection reagent and quantified by densitometry using Gelscan software. To normalize for equal loading and protein transfer, membranes were reprobed with an antibody against β-actin (1:2500, BioLegend; secondary antibody goat anti-rabbit IgG antibody HRP (ABIN)). Changes in MBP expression level in the presence of test compounds were compared to MBP expression in control conditions.

Description of MBP Fiber Plates/Oligodendrocyte Maturation/Myelination Assay

OPCs were seeded at 16,000-22,000 cells per $cm^2$ in Mimetix Aligned 96-well fiber plates (Electrospining company). After 2 days in proliferation medium and 2 days in growth factor-free Neurobasal medium to induce spontaneous in vitro differentiation and GPR17 protein expression, vehicle or 1 µM antagonist/inverse agonist test compounds were added in terminal differentiation medium supplemented with 0.20 ng/mL triiodothyronine and 10 ng/mL ciliary neurotrophic factor for 6 days, changing the medium after 3 days. Then cells were fixed in 4% paraformaldehyde, followed by PBS washes, permeabilization in 0.1% TritonX-100 in PBS and blocking with 10% goat serum and 1% bovine serum albumin in phosphate-buffered saline. MBP antibody was diluted in blocking buffer (1:2000) and incubated for 1 h at 37° C. Cells were washed in PBS again and incubated 1 h with Cy2-conjugated secondary antibodies against mouse IgG (Millipore, 1:500). After PBS washes, cells were stained with 0.2 µg/mL DAPI, washed again and mounted with Mowiol. Fluorescent images were taken by using a Zeiss AxioObserver.Z1 microscope with ApoTome Imaging System and a Plan-Apochromat 20×/0.8 objective, with an eGFP filter (excitation 470/40 nm; emission 525/50 nm) and DAPI filter (excitation 365 nm; emission 445/50 nm). At least 15 random areas for control (terminal differentiation medium with 0.1% DMSO) and for test compounds were imaged using the same settings processed with Zeiss ZEN2.3 software. Changes in number myelinated fibers was reported by group of fiber lengths (0 to 40 μm, 41 to 60 μm, 61 to 80, 81 to 100, 101 to 120 and >120 μm)) in the absence or presence of GPR17 negative modulator.

The invention claimed is:

1. A compound having the formula I formula I wherein
X1 is N or =C(R7)-,
X2 is N or =C(R12)-,
X3 is N or =C(R9)-,
R1 is selected from $C_{1-6}$ alkyl, $C_{3-5}$cycloalkyl, and $C_{3-5}$heterocycloalkyl, each of which is optionally substituted with one or more substituents selected from halogen, hydroxy, oxo, azido, cyano and $C_{1-3}$alkoxy, wherein said ($C_{1-3}$)alkoxy can be unsubstituted or substituted with one or two groups selected from halogen, oxo, hydroxy and carboxy,
R2 is hydrogen or fluoro,
R4 is hydrogen or fluoro,
R5 is hydrogen or halogen,
R6 is selected from halogen, cyano, cyclopropyl, $C_{1-3}$ alkyl and $C_{1-3}$ alkyloxy, wherein any alkyl or alkyloxy can be optionally substituted by one or more fluorine atoms,
R7 is selected from hydrogen, halogen, $C_{1-2}$alkyl, fluoro $C_{1-2}$ alkyl, $C_{1-2}$ alkoxy, fluoro $C_{1-2}$ alkoxy, cyclopropyl and cyclopropyloxy,
R8 is selected from hydrogen, fluoro and methoxy,
R9 is hydrogen or fluoro,
R10 is selected from halogen, cyano, cyanomethyl, cyclopropyl and $C_{1-3}$ alkyloxy, which is optionally substituted with one or more substituents selected from halogen, $C_{1-3}$ alkyloxy and fluoro($C_{1-3}$)alkyloxy,
R11 is selected from hydrogen, fluoro and methoxy, and
R12 is hydrogen or fluoro,
or a pharmaceutically acceptable salt, solvate, isotope or cocrystal thereof.

2. A compound according to claim 1, wherein X2 and X3 are not both nitrogen at the same time.

3. A compound according to claim 1, wherein R1 is $C_{1-3}$ alkyl, which is optionally substituted with one to four substituents selected from hydroxy, fluoro, fluoromethoxy, fluoroethoxy, hydroxymethoxy and hydroxyethoxy.

4. A compound according to claim 1, wherein R1 is selected from methyl, hydroxymethyl, hydroxyethyl, hydroxypropyl, fluoromethyl, fluoroethyl, fluoropropyl, fluorohydroxyethyl, fluorohydroxypropyl, and hydroxy($C_{1-2}$)alkoxy($C_{1-2}$)alkyl.

5. A compound according to claim 1, wherein R10 is selected from chloro, bromo, fluoromethoxy, fluoroethoxy, fluoromethoxyethoxy, fluoroethoxymethoxy and fluoroethoxyethoxy.

6. A compound according to claim 1, wherein R6 is selected from fluoro, chloro, bromo, cyano, methyl, methoxy, fluoromethyl, fluoromethoxy, cyclopropyl, and isopropyl.

7. A compound according to claim 1 having Formula Ia,

Formula Ia wherein
R1 is $C_{1-3}$ alkyl which is unsubstituted or substituted with one or more substituents which are independently selected from fluoro, hydroxy and $C_{1-2}$ alkoxy, wherein the $C_{1-2}$ alkoxy can be unsubstituted or substituted by one or more substituents selected from carboxy, fluoro and hydroxy,
R2, R4 and R5 are all hydrogen,
R6 is selected from halogen, methyl, cyclopropyl, cyano, fluoromethoxy and fluoromethyl,
R7 is hydrogen or fluoro,
R8 is selected from fluoro and methoxy and
R10 is selected from halogen and $C_{1-2}$ alkyloxy, which is optionally substituted with one to three substituents selected from fluoro, methoxy and fluoromethoxy,
or a pharmaceutically acceptable salt, solvate, isotope or cocrystal thereof.

8. A compound according to claim 1, having formula Ib

Formula Ib wherein

R1 is $C_{1-3}$ alkyl which is unsubstituted or substituted with one or more substituents which are independently selected from fluoro, hydroxy and $C_{1-2}$ alkoxy, wherein the C1-2 alkoxy can be unsubstituted or substituted by one or more substituents selected from carboxy, fluoro and hydroxy, R2, R4 and R5 are all hydrogen, R6 is selected from halogen, methyl, cyclopropyl, cyano, $C_{1-3}$ alkyl and $C_{1-3}$ alkyloxy, wherein any alkyl or alkyloxy can be optionally substituted by one or more fluorine atoms R7 is selected from hydrogen, fluoro, chloro, fluoromethyl, and fluoromethoxy, and R10 is selected from halogen and $C_{1-3}$ alkyloxy, which is optionally substituted with one to three substituents selected from halogen, $C_{1-2}$ alkyloxy and fluoro($C_{1-2}$) alkyloxy, or a pharmaceutically acceptable salt, solvate, isotope or cocrystal thereof.

9. A compound according to claim 1, having formula Ic

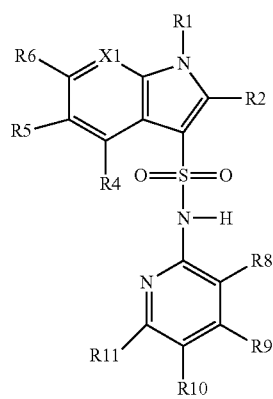

Formula Ic wherein

R1 is $C_{1-3}$ alkyl which is unsubstituted or substituted with one or more substituents which are independently selected from fluoro, hydroxy and $C_{1-2}$ alkoxy, wherein the $C_{1-2}$ alkoxy can be unsubstituted or substituted by one or more substituents selected from carboxy, fluoro and hydroxy, R2, R4 and R5 are all hydrogen, R6 is selected from halogen, methyl, cyclopropyl, cyano, fluoromethoxy, R7 is hydrogen, and R10 is selected from halogen and $C_{1-2}$ alkyloxy, which is optionally substituted with one to three substituents selected from fluoro, methoxy and fluoromethoxy, or a pharmaceutically acceptable salt, solvate, isotope or cocrystal thereof.

10. A compound according to claim 1, having formula III

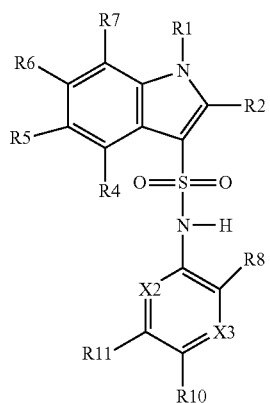

Formula III wherein

X2 is N or =C(R12)-,

X3 is N or =C(R9)-,

R1 is $C_{1-3}$ alkyl which is unsubstituted or substituted with one or more substituents which are independently selected from fluoro, hydroxy and $C_{1-2}$ alkoxy, wherein the $C_{1-2}$ alkoxy can be unsubstituted or substituted by one or more substituents selected from carboxy, fluoro and hydroxy, R2, R4 and R5 are all hydrogen, R6 is selected from halogen, methyl, cyclopropyl, cyano, fluoromethoxy and fluoromethyl, R7 is hydrogen, fluoro or chloro, and, R10 is selected from halogen and C1-2 alkyloxy, which is optionally substituted with one to three substituents selected from fluoro, methoxy and fluoromethoxy, or a pharmaceutically acceptable salt, solvate, isotope or cocrystal thereof, wherein X2 and X3 are not both nitrogen at the same time.

11. A compound according to claim 1 wherein the compound has Formula IIIa, IIIb or IIIc,

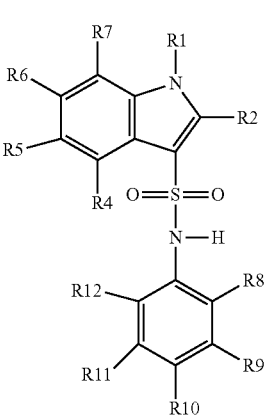

Formula IIIa

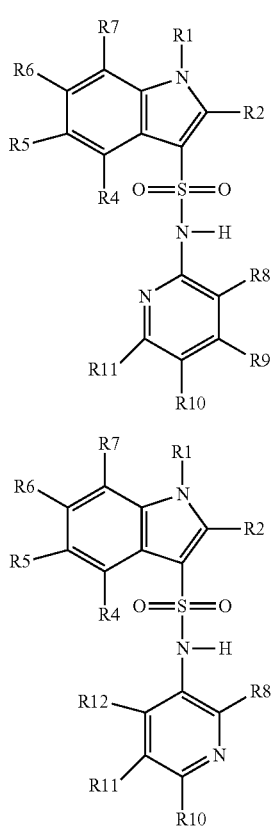

Formula IIIb

Formula IIIc wherein
R1 is C$_{1-3}$ alkyl which is unsubstituted or substituted with one or more substituents which are independently selected from fluoro, hydroxy and C$_{1-2}$ alkoxy, wherein the C$_{1-2}$ alkoxy can be unsubstituted or substituted by one or more substituents selected from carboxy, fluoro and hydroxy,
R2, R4 and R5 are all hydrogen,
R6 is selected from halogen, methyl, cyclopropyl, cyano, fluoromethoxy and fluoromethyl,
R7 is hydrogen,
R8 is selected from fluoro and methoxy,
R9 is hydrogen,
R10 is selected from fluoro, chloro, bromo, fluoromethoxy and fluoroethoxy, and
R11 is selected fluoro and methoxy,
or a pharmaceutically acceptable salt, solvate, isotope or cocrystal thereof.

12. A compound according to claim 1 wherein
R1 is selected from C$_{1-3}$ alkyl and (C$_{1-2}$)alkoxy(C$_{1-2}$)alkyl, each of which is optionally substituted with one to four substituents selected from hydroxy and fluoro,
R2, R4, R5, R7, if present, R9 and R12, if present, are all hydrogen,
R6 is selected from fluoro, chloro, bromo, fluoromethoxy and fluoromethyl,
R8 is selected from fluoro and methoxy,
R10 is selected from halogen and fluro(C$_{1-3}$)alkoxy,
R11 is fluoro or methoxy,
or a pharmaceutically acceptable salt, solvate, isotope or cocrystal thereof.

13. A compound according to claim 1, wherein R6 is selected from chloro and bromo.

14. A compound according to claim 1, which is selected from the group consisting of
N-(4-bromo-2,5-difluorophenyl)-6-chloro-1-(2-fluoro-3-hydroxypropyl) pyrrolo [2,3-b]pyridine-3-sulfonamide,
N-(4-bromo-2,5-difluorophenyl)-6-chloro-1-(2-fluoro-3-hydroxypropyl) indole-3-sulfonamide,
6-chloro-N-(6-chloro-5-fluoro-2-methoxypyridin-3-yl)-1-(3-fluoro-2-hydroxypropyl) indole-3-sulfonamide,
N-(4-bromo-2,5-difluorophenyl)-6-chloro-1-(3,3,3-trifluoro-2-hydroxypropyl) indole-3-sulfonamide,
6-chloro-N-(6-chloro-5-fluoro-2-methoxypyridin-3-yl)-1-(2,2-difluoroethyl) indole-3-sulfonamide,
6-chloro-N-(6-chloro-5-fluoro-2-methoxypyridin-3-yl)-1-(2,3-dihydroxypropyl) indole-3-sulfonamide,
6-chloro-N-(6-chloro-5-fluoro-2-methoxypyridin-3-yl)-1-methylindole-3-sulfonamide,
N-(4-bromo-2,5-difluorophenyl)-6-chloro-1-(3-fluoro-2-hydroxypropyl) indole-3-sulfonamide,
6-chloro-N-[4-(difluoromethoxy)-2,5-difluorophenyl]-1-(2,3-dihydroxypropyl) indole-3-sulfonamide,
N-(4-bromo-2,5-difluorophenyl)-6-chloro-1-(2-hydroxypropyl) indole-3-sulfonamide,
N-(4-bromo-2,5-difluorophenyl)-6-chloro-1-methylpyrrolo [2,3-b]pyridine-3-sulfonamide,
6-chloro-N-[4-(difluoromethoxy)-2,5-difluorophenyl]-1-methylpyrrolo [2,3-b]pyridine-3-sulfonamide,
N-(4-bromo-2,5-difluorophenyl)-6-chloro-1-(2,3-dihydroxypropyl) pyrrolo [2,3-b]pyridine-3-sulfonamide,
N-(4-bromo-2,5-difluorophenyl)-6-chloro-1-(2-hydroxyethyl) pyrrolo [2,3-b]pyridine-3-sulfonamide,
N-(4-bromo-2,5-difluorophenyl)-6-chloro-1-[2-(2-hydroxyethoxy) ethyl]indole-3-sulfonamide,
6-chloro-N-[6-(difluoromethoxy)-5-fluoro-2-methoxypyridin-3-yl]-1-(2-hydroxyethyl) pyrrolo [2,3-b]pyridine-3-sulfonamide,
6-chloro-N-[4-(difluoromethoxy)-2,5-difluorophenyl]-1-(2-fluoroethyl) indole-3-sulfonamide,
N-(4-bromo-2,5-difluorophenyl)-6-chloro-1-(2,3-dihydroxypropyl) indole-3-sulfonamide,
6-chloro-N-[4-(difluoromethoxy)-2,5-difluorophenyl]-1-methylindole-3-sulfonamide,
6-chloro-N-[4-(difluoromethoxy)-2,5-difluorophenyl]-1-(2-hydroxyethyl) indole-3-sulfonamide,
N-(4-bromo-2,5-difluorophenyl)-6-chloro-1-methylindole-3-sulfonamide,
and
N-(4-bromo-2,5-difluorophenyl)-6-chloro-1-(2-hydroxyethyl) indole-3-sulfonamide.

15. A pharmaceutical composition comprising a compound according to claim 1 and at least one pharmaceutically acceptable carrier.

16. A method of treating a demyelination disorder comprising administering a compound according to claim 1 to a subject in need thereof.

17. A method according to claim 16, wherein the demyelination disorder is multiple sclerosis.

18. A compound having formula II

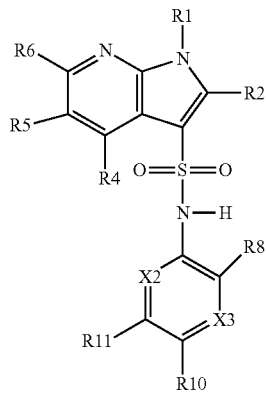
Formula II wherein X2 is

N or =C(R12)-

X3 is N or =C(R9)-

R1 is $C_{1-3}$ alkyl which is unsubstituted or substituted with one or more substituents which are independently selected from fluoro, hydroxy, carboxy and $C_{1-2}$ alkoxy, wherein the $C_{1-2}$ alkoxy can be unsubstituted or substituted by one or more substituents selected from carboxy, fluoro and hydroxy, R2, R4 and R5 are all hydrogen, R6 is selected from halogen, methyl, cyclopropyl, cyano, fluoromethoxy and fluoromethyl, R8 is selected from hydrogen, fluoro and methoxy, R9 is hydrogen or fluoro, R10 is selected from halogen and C1-2 alkyloxy, which is optionally substituted with one to three substituents selected from fluoro, methoxy and fluoromethoxy, R11 is selected from hydrogen, fluoro and methoxy, R12 is hydrogen or fluoro, wherein X2 and X3 are not both nitrogen at the same time, or a pharmaceutically acceptable salt, solvate, isotope or cocrystal thereof.

19. A compound according to claim 18, wherein the compound has Formula IIa, IIb or IIc,

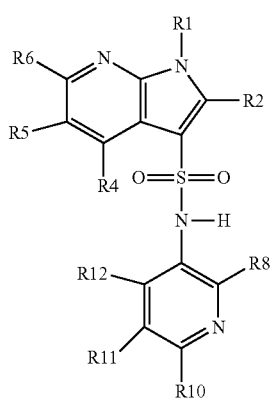
Formula IIa

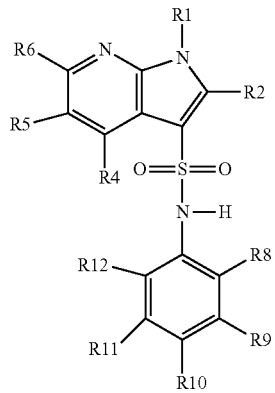
Formula IIb

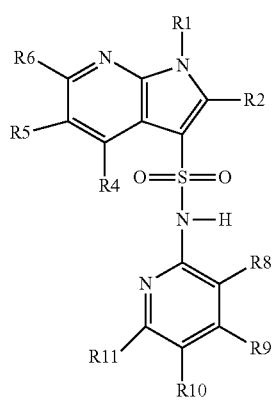
Formula IIc wherein

R8 is selected from fluoro and methoxy,

R9 is hydrogen,

R11 is selected from fluoro and methoxy, and

R12 is hydrogen, or a pharmaceutically acceptable salt, solvate, isotope or cocrystal thereof.

20. A compound according to claim 18, wherein the compound has Formula IIa, IIb or IIc,

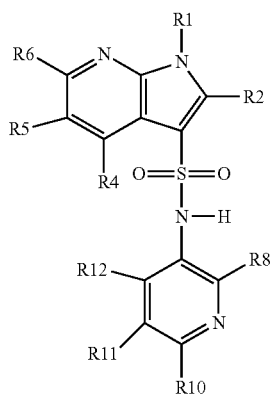
Formula IIa

103

-continued

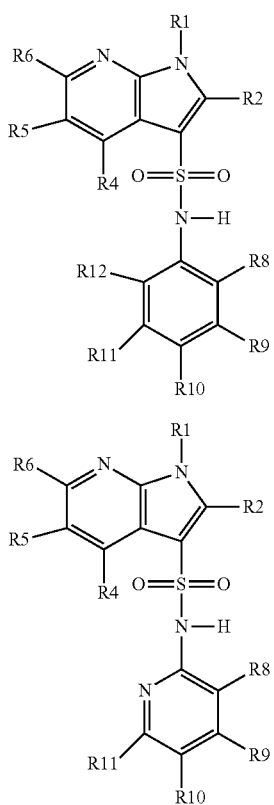

Formula IIb

Formula IIc wherein
R6 is selected from chloro and fluoromethyl,
or a pharmaceutically acceptable salt, solvate, isotope or cocrystal thereof.

21. A compound having the formula

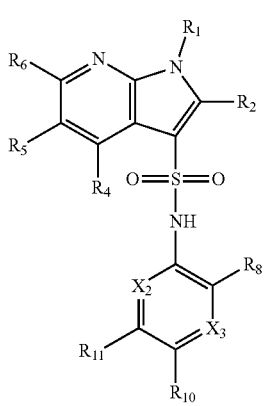

wherein
X2 is N or =C(R12)-,
X3 is N or =C(R9)-,
R1 is selected from $C_{1-6}$ alkyl, $C_{3-5}$cycloalkyl, and $C_{3-5}$heterocycloalkyl, each of which is optionally substituted with one or more substituents selected from halogen, hydroxy, oxo, azido, cyano, carboxy and $C_{1-3}$alkoxy, wherein said $(C_{1-3})$alkoxy can be unsubstituted or substituted with one or two groups selected from halogen, oxo, hydroxy and carboxy,

104

R2 is hydrogen or fluoro,
R4 is hydrogen or fluoro,
R5 is hydrogen or halogen,
R6 is selected from halogen, cyano, cyclopropyl, $C_{1-3}$ alkyl and $C_{1-3}$ alkyloxy, wherein any alkyl or alkyloxy can be optionally substituted by one or more fluorine atoms,
R7 is selected from hydrogen, halogen, $C_{1-2}$alkyl, fluoro $C_{1-2}$ alkyl, $C_{1-2}$ alkoxy, fluoro $C_{1-2}$ alkoxy, cyclopropyl and cyclopropyloxy,
R8 is selected from hydrogen, fluoro and methoxy,
R9 is hydrogen or fluoro,
R10 is selected from halogen, cyano, cyanomethyl, cyclopropyl and $C_{1-3}$ alkyloxy, which is optionally substituted with one or more substituents selected from halogen, $C_{1-3}$ alkyloxy and fluoro($C_{1-3}$)alkyloxy,
R11 is selected from hydrogen, fluoro and methoxy, and
R12 is hydrogen or fluoro,
or a pharmaceutically acceptable salt, solvate, isotope or cocrystal thereof.

22. A method of treating multiple sclerosis by modulating GPR17 receptor activity, comprising administering a therapeutically effective amount of a compound of formula I to a patient in need of such treatment, wherein formula I is formula I

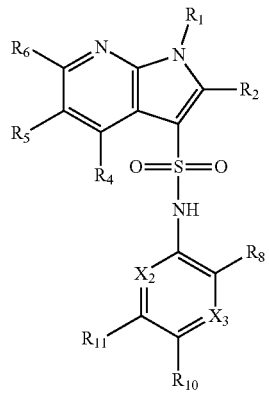

wherein
X1 is N or =C(R7)-,
X2 is N or =C(R12)-,
X3 is N or =C(R9)-,
R1 is selected from $C_{1-6}$ alkyl, $C_{3-5}$cycloalkyl, and $C_{3-5}$heterocycloalkyl, each of which is optionally substituted with one or more substituents selected from halogen, hydroxy, oxo, azido, cyano, carboxy and $C_{1-3}$alkoxy, wherein said $(C_{1-3})$alkoxy can be unsubstituted or substituted with one or two groups selected from halogen, oxo, hydroxy and carboxy,
R2 is hydrogen or fluoro,
R4 is hydrogen or fluoro,
R5 is hydrogen or halogen,
R6 is selected from halogen, cyano, cyclopropyl, $C_{1-3}$ alkyl and $C_{1-3}$ alkyloxy, wherein any alkyl or alkyloxy can be optionally substituted by one or more fluorine atoms,
R7 is selected from hydrogen, halogen, $C_{1-2}$alkyl, fluoro $C_{1-2}$ alkyl, $C_{1-2}$ alkoxy, fluoro $C_{1-2}$ alkoxy, cyclopropyl and cyclopropyloxy,
R8 is selected from hydrogen, fluoro and methoxy,
R9 is hydrogen or fluoro, R10 is selected from halogen, cyano, cyanomethyl, cyclopropyl and $C_{1-3}$ alkyloxy, which is optionally substituted with one or more substituents selected from halogen, $C_{1-3}$ alkyloxy and fluoro($C_{1-3}$)alkyloxy, R11 is selected from hydrogen, fluoro and methoxy, R12 is hydrogen or fluoro, or a pharmaceutically acceptable salt, solvate, isotope or cocrystal thereof.

23. A method according to claim 22 wherein the compound is 2-[3-[(4-bromo-2,5-difluorophenyl) sulfamoyl]-6-chloroindol-1-yl]acetic acid.

* * * * *